United States Patent
Kim et al.

(10) Patent No.: US 12,358,876 B2
(45) Date of Patent: Jul. 15, 2025

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Hyunjung Kim, Suwon-si (KR); Miyoung Chae, Suwon-si (KR); Eunsuk Kwon, Suwon-si (KR); Sangmo Kim, Hwaseong-si (KR); Soonok Jeon, Seoul (KR); Yeonsook Chung, Seoul (KR); Dalho Huh, Suwon-si (KR); Youngseok Park, Yongin-si (KR); Youngmok Son, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 33 days.

(21) Appl. No.: 18/045,345

(22) Filed: Oct. 10, 2022

(65) Prior Publication Data
US 2023/0118804 A1   Apr. 20, 2023

Related U.S. Application Data

(62) Division of application No. 15/054,758, filed on Feb. 26, 2016, now abandoned, and a division of
(Continued)

(30) Foreign Application Priority Data

Oct. 5, 2015 (KR) ........................ 10-2015-0139991

(51) Int. Cl.
*C07D 209/88* (2006.01)
*C07D 409/10* (2006.01)
(Continued)

(52) U.S. Cl.
CPC ......... *C07D 209/88* (2013.01); *C07D 409/10* (2013.01); *C09K 11/025* (2013.01);
(Continued)

(58) Field of Classification Search
None
See application file for complete search history.

(56) References Cited

U.S. PATENT DOCUMENTS

| | | |
|---|---|---|
| 2005/0175858 A1 | 8/2005 | Jung et al. |
| 2009/0030202 A1 | 1/2009 | Iwakuma et al. |
| | (Continued) | |

FOREIGN PATENT DOCUMENTS

| | | |
|---|---|---|
| JP | 200471380 | 3/2004 |
| JP | 2011211174 A | 10/2011 |
| | (Continued) | |

OTHER PUBLICATIONS

English Translation of Office Action issued May 3, 2022, in corresponding KR Patent Application No. 10-2015-0139991, 5 pp.
(Continued)

*Primary Examiner* — Eli S Mekhlin
(74) *Attorney, Agent, or Firm* — CANTOR COLBURN LLP

(57) ABSTRACT

A condensed cyclic compound represented by Formula 1:

Formula 1

(Continued)

wherein in Formula 1, $Ar_1$ and $R_1$ to $R_8$ are the same as described in the specification.

13 Claims, 1 Drawing Sheet

Related U.S. Application Data application No. 16/206,331, filed on Nov. 30, 2018, now Pat. No. 11,508,914.

(51) Int. Cl.

| | | |
|---|---|---|
| *C09K 11/02* | (2006.01) | |
| *C09K 11/06* | (2006.01) | |
| *H10K 50/11* | (2023.01) | |
| *H10K 85/30* | (2023.01) | |
| *H10K 85/60* | (2023.01) | |
| *H10K 101/10* | (2023.01) | |
| *H10K 101/30* | (2023.01) | |
| *H10K 101/40* | (2023.01) | |

(52) U.S. Cl.
CPC ............ *C09K 11/06* (2013.01); *H10K 85/361* (2023.02); *H10K 85/6572* (2023.02); *H10K 85/6574* (2023.02); *H10K 85/6576* (2023.02); *C09K 2211/1007* (2013.01); *C09K 2211/1022* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H10K 50/11* (2023.02); *H10K 85/322* (2023.02); *H10K 85/342* (2023.02); *H10K 85/346* (2023.02); *H10K 85/631* (2023.02); *H10K 85/636* (2023.02); *H10K 2101/10* (2023.02); *H10K 2101/30* (2023.02); *H10K 2101/40* (2023.02)

(56) References Cited

U.S. PATENT DOCUMENTS

| | | |
|---|---|---|
| 2012/0097932 A1 | 4/2012 | Kim et al. |
| 2012/0193613 A1 | 8/2012 | Kadoma et al. |
| 2013/0001541 A1 | 1/2013 | Hayashi |
| 2013/0011952 A1 | 1/2013 | Hayashi et al. |
| 2014/0175395 A1 | 6/2014 | Kim et al. |
| 2014/0203257 A1 | 7/2014 | Hwang et al. |
| 2014/0374720 A1 | 12/2014 | Kato et al. |
| 2015/0090974 A1 | 4/2015 | Kim et al. |
| 2015/0105564 A1 | 4/2015 | Adachi et al. |
| 2015/0318489 A1* | 11/2015 | Oshiyama ............ H10K 85/615 257/40 |
| 2017/0362241 A1 | 12/2017 | Nishimae et al. |

FOREIGN PATENT DOCUMENTS

| | | | |
|---|---|---|---|
| KR | 1020050040960 | | 5/2005 |
| KR | 1020110088427 | | 8/2011 |
| KR | 1020120094838 | A | 8/2012 |
| KR | 1020130016267 | | 2/2013 |
| KR | 101344787 | B1 | 12/2013 |
| KR | 1020140080205 | | 6/2014 |
| KR | 1020150005583 | | 1/2015 |
| WO | 2004074399 | | 9/2004 |
| WO | 2011111860 | A1 | 9/2011 |
| WO | 2011126224 | A1 | 10/2011 |
| WO | WO-2014061991 | A1 * | 4/2014 ........... C07D 209/86 |
| WO | 2014092014 | | 6/2014 |

OTHER PUBLICATIONS

Office Action issued May 3, 2022, in corresponding KR Patent Application No. 10-2015-0139991, 6 pp.

\* cited by examiner

10

| 19 |
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application is a divisional of U.S. patent application Ser. No. 16/206,331, filed on Nov. 30, 2018, which is a divisional of U.S. patent application Ser. No. 15/054,758, filed on Feb. 26, 2016 in the United States Patent and Trademark Office, which claims priority to Korean Patent Application No. 10-2015-0139991, filed on Oct. 5, 2015, in the Korean Intellectual Property Office, and all the benefits accruing therefrom under 35 U.S.C. § 119, the contents of which are incorporated herein in their entireties by reference.

BACKGROUND

1. Field

The present disclosure relates to a condensed cyclic compound and an organic light-emitting device including the same.

2. Description of the Related Art

Organic light emitting devices (OLEDs) are self-emission devices that have wide viewing angles, high contrast ratios, and short response times. In addition, the OLEDs exhibit excellent luminance, driving voltage and response speed characteristics, and produce full-color images.

A typical organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers such as the holes and the electrons are recombined in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

Provided are a condensed cyclic compound and an organic light-emitting device including the same.

Additional aspects will be set forth in part in the description which follows and, in part, will be apparent from the description, or may be learned by practice of the presented exemplary embodiments.

According to an exemplary embodiment, a condensed cyclic compound represented by Formula 1 is provided:

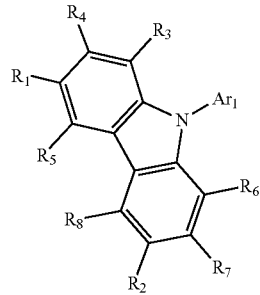

Formula 1 wherein in Formula 1, $Ar_1$ is selected from groups represented by Formulae 2A to 2C:

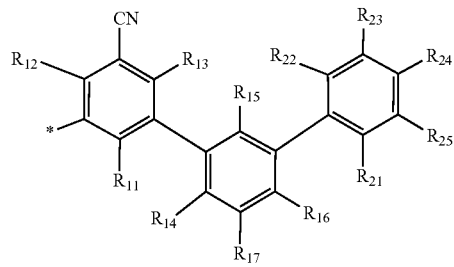

Formula 2A

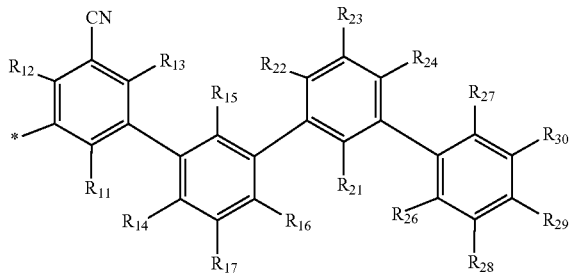

Formula 2B

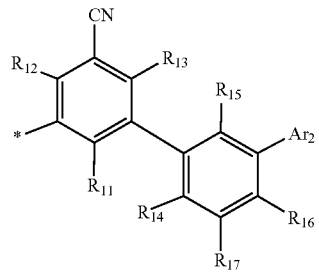

Formula 2C wherein $R_{13}$ and $R_{15}$ in Formulae 2A to 2C are optionally connected to each other through *—O—*', *—S—*', *—C($R_{31}$)($R_{32}$)—*', or *—Si($R_{31}$)($R_{32}$)—*' to form a 5-membered ring, wherein $R_{11}$ and $R_{14}$ in Formulae 2A to 2C are optionally connected to each other through *—O—*', *—S—*', *—C($R_{33}$)($R_{34}$)—*', or *—Si($R_{33}$)($R_{34}$)—*' t form a 5-membered ring, wherein $R_{15}$ and $R_{22}$ in Formulae 2A and 2B are optionally connected to each other through *—O—*', *—S—*', *—C($R_{35}$)($R_{36}$)—*', or *—Si($R_{35}$)($R_{36}$)—*' to form a 5-membered ring, wherein $R_{16}$ and $R_{21}$ in Formulae 2A and 2B are optionally connected to each other through *—O—*', *—S—*', *—C($R_{37}$)($R_{38}$)—*', or *—Si($R_{37}$)($R_{38}$)—*' to form a 5-membered ring, wherein $R_{24}$ and $R_{27}$ in Formula 2B are optionally connected to each other through *—O—*', *—S—*', *—C($R_{39}$)($R_{40}$)—*', or *—Si($R_{39}$)($R_{40}$)—*' to form a 5-membered ring, wherein $R_{21}$ and $R_{26}$ in Formula 2B are optionally connected to each other through *—O—*', *—S—*', *—C($R_{41}$)($R_{42}$)—*', or *—Si($R_{41}$)($R_{42}$)—*' to form a 5-membered ring, wherein $R_1$ to $R_8$, $R_{11}$ to $R_{17}$, $R_{21}$ to $R_{30}$, and $R_{31}$ to $R_{42}$ in Formulae 1 and 2A to 2C are each independently selected from:

hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

a $C_1$-$C_{20}$ alkyl group and $C_1$-$C_{20}$ alkoxy group, each substituted with at least one selected from deuterium and a cyano group; and a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

wherein $Ar_2$ in Formula 2C is selected from a dibenzofuranyl group, a dibenzothiophenyl group, and a dibenzosilolyl group; and a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;

wherein * indicates a binding site to an adjacent atom.

In various embodiments, an organic light-emitting device includes:

a first electrode;

a second electrode; and an organic layer disposed between the first electrode and the second electrode, wherein the organic layer includes an emission layer and at least one condensed cyclic compound represented by Formula 1.

BRIEF DESCRIPTION OF THE DRAWING

These and/or other aspects will become apparent and more readily appreciated from the following description of the exemplary embodiments, taken in conjunction with the FIGURE, which is a schematic cross-sectional view of an organic light-emitting device according to an exemplary embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

According to an exemplary embodiment, a condensed cyclic compound represented by Formula 1 is provided:

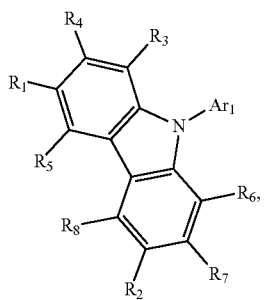

Formula 1 wherein $Ar_1$ in Formula 1 is selected from groups represented by Formulae 2A to 2C:

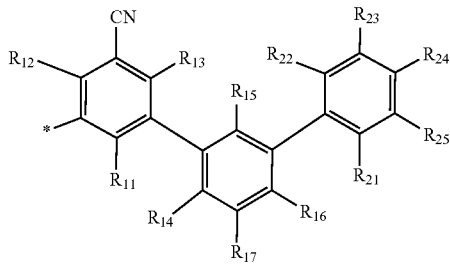

Formula 2A

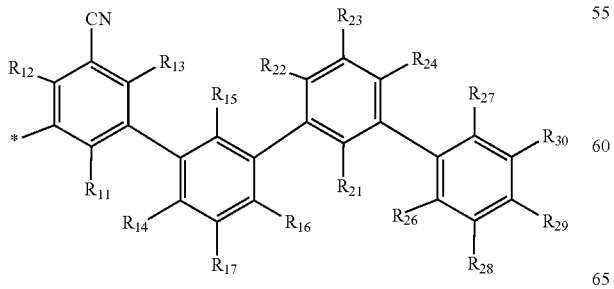

Formula 2B

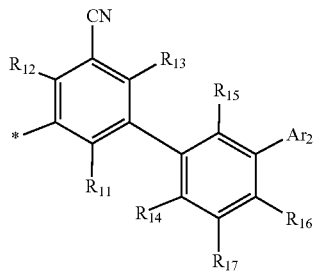

Formula 2C wherein $R_{13}$ and $R_{15}$ in Formulae 2A to 2C are optionally connected to each other through *—O—*', *—S—*', *—C($R_{31}$)($R_{32}$)—*', or *—Si($R_{31}$)($R_{32}$)—*' to form a 5-membered ring, wherein $R_{11}$ and $R_{14}$ in Formulae 2A to 2C are optionally connected to each other through *—O—*', *—S—*', *—C($R_{33}$)($R_{34}$)—*', or *—Si($R_{33}$)($R_{34}$)—*' to form a 5-membered ring, wherein $R_{15}$ and $R_{22}$ in Formulae 2A and 2B are optionally connected to each other through *—O—*', *—S—*', *—C($R_{35}$)($R_{36}$)—*', or *—Si($R_{35}$)($R_{36}$)—*' to form a 5-membered ring, wherein $R_{16}$ and $R_{21}$ in Formulae 2A and 2B are optionally connected to each other through *—O—*', *—S—*', *—C($R_{37}$)($R_{38}$)—*', or *—Si($R_{37}$)($R_{38}$)—*' to form a 5-membered ring, wherein $R_{24}$ and $R_{27}$ in Formula 2B are optionally connected to each other through *—O—*', *—S—*, *—C($R_{39}$)($R_{40}$)—*', or *—Si($R_{39}$)($R_{40}$)—*' to form a 5-membered ring, wherein $R_{21}$ and $R_{26}$ in Formula 2B are optionally connected to each other through *—O—*', *—S—*, *—C($R_{41}$)($R_{42}$)—*', or *—Si($R_{41}$)($R_{42}$)—*' to form a 5-membered ring.

According to an exemplary embodiment, $Ar_1$ in Formula 1 may be selected from groups represented by Formulae 2A-1 to 2A-4:

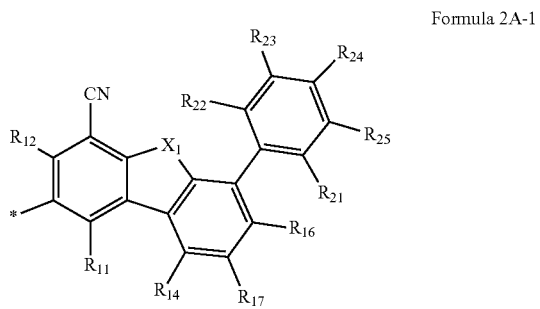

Formula 2A-1

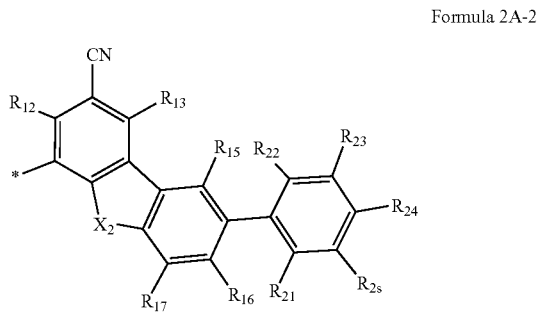

Formula 2A-2

Formula 2A-3
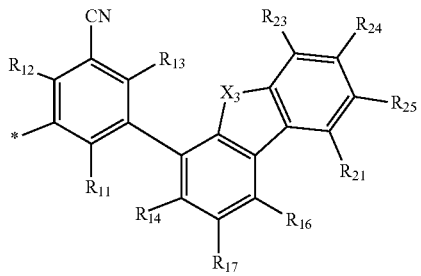

Formula 2A-4
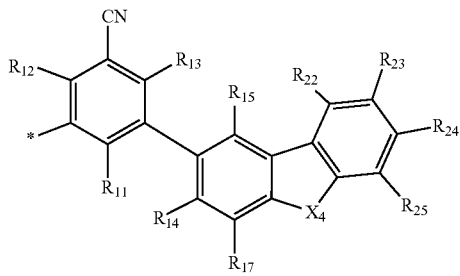

wherein in Formulae 2A-1 to 2A-4,
$X_1$ is O, S, $C(R_{31})(R_{32})$, or $Si(R_{31})(R_{32})$,
$X_2$ is O, S, $C(R_{33})(R_{34})$, or $Si(R_{33})(R_{34})$,
$X_3$ is O, S, $C(R_{35})(R_{36})$, or $Si(R_{35})(R_{36})$,
$X_4$ is O, S, $C(R_{37})(R_{38})$, or $Si(R_{37})(R_{38})$,
descriptions for $R_{11}$ to $R_{17}$, $R_{21}$ to $R_{25}$, and $R_{31}$ to $R_{38}$ are the same as described herein,
* indicates a binding site to an adjacent atom.

In various embodiments, $Ar_1$ in Formula 1 may be selected from groups represented by Formulae 2B-1 to 2B-6:

Formula 2B-1
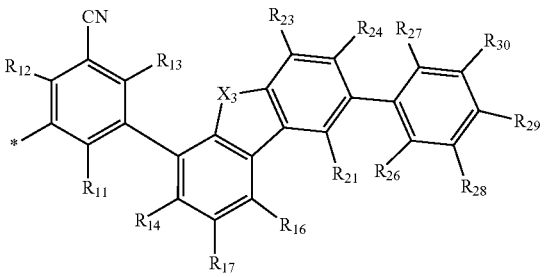

Formula 2B-2
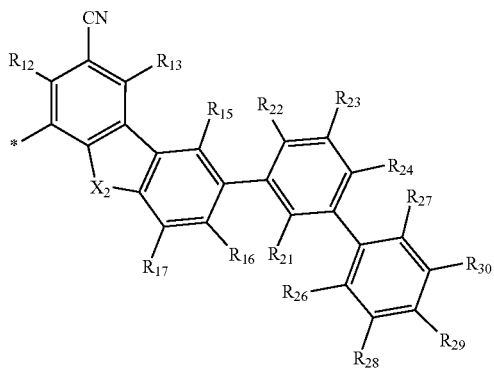

Formula 2B-3
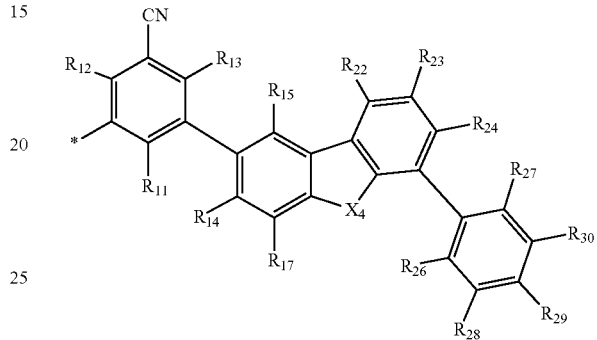

Formula 2B-4
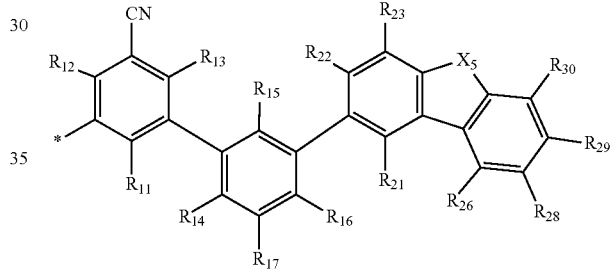

Formula 2B-5
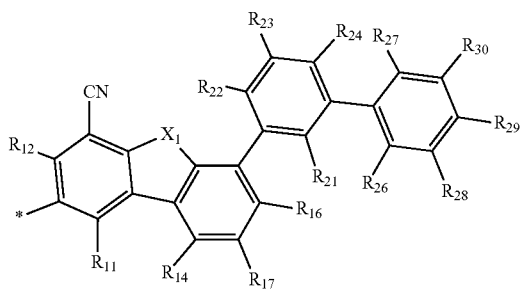

Formula 2B-6
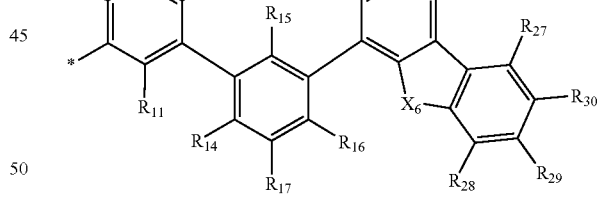

wherein in Formulae 2B3-1 to 2B3-6,
$X_1$ is O, S, $C(R_{31})(R_{32})$, or $Si(R_{31})(R_{32})$,
$X_2$ is O, S, $C(R_{33})(R_{34})$, or $Si(R_{33})(R_{34})$,
$X_3$ is O, S, $C(R_{35})(R_{36})$, or $Si(R_{35})(R_{36})$,
$X_4$ is O, S, $C(R_{37})(R_{38})$, or $Si(R_{37})(R_{38})$,
$X_5$ is O, S, $C(R_{39})(R_{40})$, or $Si(R_{39})(R_{40})$,
$X_6$ is O, S, $C(R_{41})(R_{42})$, or $Si(R_{41})(R_{42})$,
the descriptions for $R_{11}$ to $R_{17}$, $R_{21}$ to $R_{30}$, and $R_{31}$ to $R_{42}$ are the same as described herein,
* indicates a binding site to an adjacent atom.

According to some embodiments, $Ar_1$ in Formula 1 may be selected from groups represented by Formulae 2A to 2C, wherein $R_{13}$ and $R_{15}$, $R_{11}$ and $R_{14}$, $R_{15}$ and $R_{22}$, $R_{16}$ and $R_{21}$, $R_{24}$ and $R_{27}$, and $R_{21}$ and $R_{26}$ in Formulae 2A to 2C may not be connected to each other.

$R_1$ to $R_8$, $R_{11}$ to $R_{17}$, $R_{21}$ to $R_{30}$, and $R_{31}$ to $R_{42}$ in Formulae 1 and 2A to 2C may each independently be selected from

- hydrogen, deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;
- a $C_1$-$C_{20}$ alkyl group and a $C_1$-$C_{20}$ alkoxy group, each substituted with at least one selected from deuterium and a cyano group; and
- a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group;
- $Ar_2$ in Formula 2A may be selected from
- a dibenzofuranyl group, a dibenzothiophenyl group, and a dibenzosilolyl group; and
- a dibenzofuranyl group, a dibenzothiophenyl group, and a dibenzosilolyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, a fluorenyl group, a pyridinyl group, a pyrimidinyl group, a pyrazinyl group, a pyridazinyl group, a triazinyl group, a dibenzofuranyl group, a dibenzothiophenyl group, and a dibenzosilolyl group,
- * indicates a binding site to an adjacent atom.

For example, $R_1$ to $R_8$, $R_{11}$ to $R_{17}$, $R_{21}$ to $R_{30}$, and $R_{31}$ to $R_{42}$ in Formulae 1 and 2A to 2C may each independently be selected from

- hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group;
- a $C_1$-$C_{20}$ alkyl group substituted with at least one selected from deuterium and a cyano group; and
- a phenyl group, a biphenyl group, a terphenyl group, a fluorenyl group, a dibenzofuranyl group, a dibenzothiophenyl group, and a dibenzosilolyl group, each substituted with at least one selected from deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group, but they are not limited thereto.

As another example, $R_1$ to $R_8$, $R_{11}$ to $R_{17}$, $R_{21}$ to $R_{30}$, and $R_{31}$ to $R_{42}$ in Formulae 1 and 2A to 2C may each independently be selected from hydrogen, deuterium, a cyano group, a $C_1$-$C_{20}$ alkyl group, a phenyl group, a biphenyl group, a terphenyl group, a fluorenyl group, a dibenzofuranyl group, a dibenzothiophenyl group, and a dibenzosilolyl group.

According to an exemplary embodiment, $R_1$ to $R_8$, $R_{11}$ to $R_{17}$, $R_{21}$ to $R_{30}$, and $R_{31}$ to $R_{42}$ in Formulae 1 and 2A to 2C may each independently be selected from hydrogen, deuterium, and a cyano group; and a phenyl group, a biphenyl group, and a terphenyl group, each substituted with at least one selected from deuterium, a cyano group, and a phenyl group.

In various embodiments, $R_1$ to $R_8$, $R_{11}$ to $R_{17}$, $R_{21}$ to $R_{30}$, and $R_{31}$ to $R_{42}$ in Formulae 1 and 2A to 2C may each independently be selected from hydrogen, deuterium, a cyano group, and groups represented by Formulae 4-1 to 4-29, but they are not limited thereto:

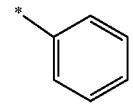

Formula 4-1

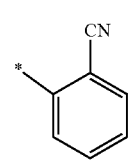

Formula 4-2

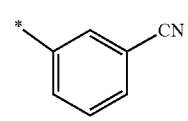

Formula 4-3

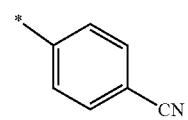

Formula 4-4

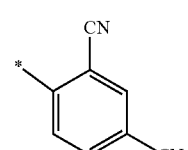

Formula 4-5

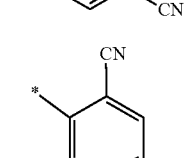

Formula 4-6

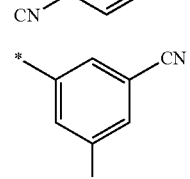

Formula 4-7

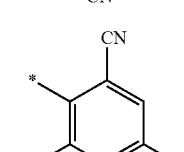

Formula 4-8

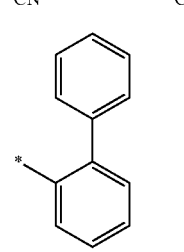

Formula 4-9

Formula 4-10
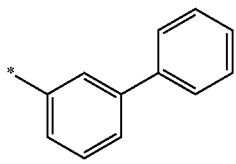
Formula 4-11
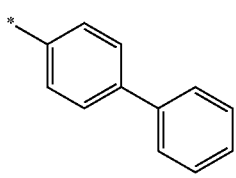
Formula 4-12
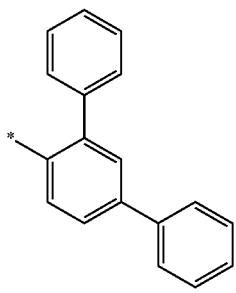
Formula 4-13
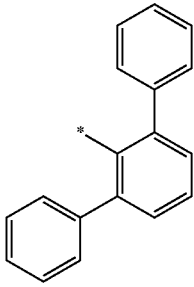
Formula 4-14
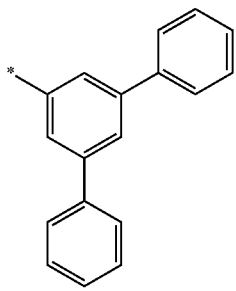
Formula 4-15
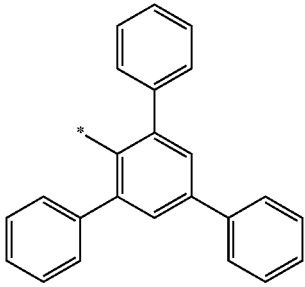
Formula 4-16
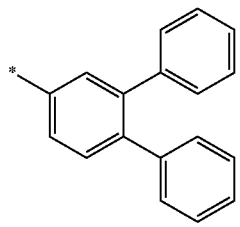
Formula 4-17
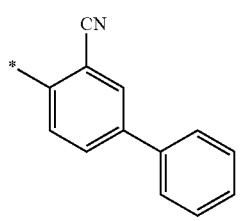
Formula 4-18
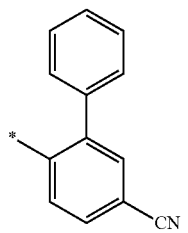
Formula 4-19
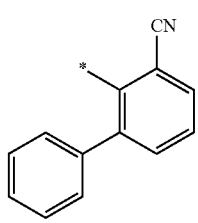
Formula 4-20
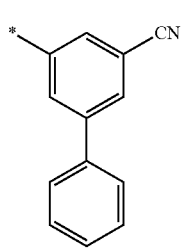
Formula 4-21
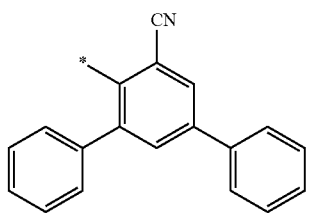

-continued

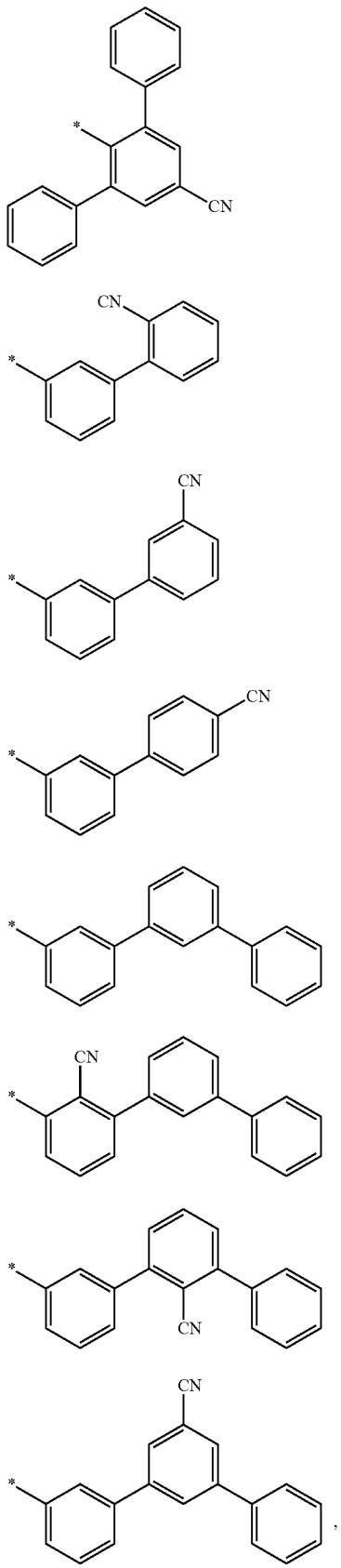

Formula 4-22

Formula 4-23

Formula 4-24

Formula 4-25

Formula 4-26

Formula 4-27

Formula 4-28

Formula 4-29 wherein in Formulae 4-1 to 4-29, * indicates a binding site to an adjacent atom.

According to an exemplary embodiment, at least one of $R_1$ and $R_2$ in Formula 1 may be a cyano group.

In various embodiments, $R_1$ in Formula 1 may be a cyano group, and $R_2$ to $R_8$ in Formula 1 may each independently be selected from hydrogen, deuterium, and a cyano group; and a phenyl group, a biphenyl group, and a terphenyl group, each substituted with at least one selected from deuterium, a cyano group, and a phenyl group.

According to some embodiments, $R_1$ and $R_2$ in Formula 1 may be a cyano group, $R_3$ to $R_8$ in Formula 1 may each independently be selected from hydrogen, deuterium, and a cyano group; and a phenyl group, a biphenyl group, and a terphenyl group, each substituted with at least one selected from deuterium, a cyano group, and a phenyl group.

According to some embodiments, $R_{11}$ to $R_{17}$ and $R_{21}$ to $R_{25}$ in Formula 2A may all be hydrogen, or at least one of $R_{23}$, $R_{25}$, and $R_{15}$ to $R_{17}$ in Formula 2A may each independently be selected from deuterium and a cyano group; and a phenyl group, a biphenyl group, and a terphenyl group, each substituted with at least one selected from deuterium, a cyano group, and a phenyl group; or $R_{11}$ to $R_{17}$, $R_{21}$ to $R_{24}$, and $R_{26}$ to $R_{30}$ in Formula 2B may all be hydrogen, or at least one of $R_{15}$, $R_{17}$, $R_{21}$, $R_{23}$, $R_{28}$, and $R_{30}$ in Formula 2B may each independently be selected from deuterium and a cyano group; and a phenyl group, a biphenyl group, and a terphenyl group, each substituted with at least one selected from deuterium, a cyano group, and a phenyl group, or $R_{17}$ in Formula 2C may be a cyano group, a phenyl group, a biphenyl group or a terphenyl group, but they are not limited thereto.

According to some embodiments, $R_{11}$ to $R_{17}$ and $R_{21}$ to $R_{25}$ of Formula 2A may all be hydrogen, or at least one of $R_{23}$, $R_{25}$, and $R_{15}$ to $R_{17}$ in Formula 2A may each independently be selected from a cyano group and groups represented by Formulae 4-1 to 4-29, or $R_{11}$ to $R_{17}$, $R_{21}$ to $R_{24}$, and $R_{26}$ to $R_{30}$ in Formula 2B may all be hydrogen, or at least one of $R_{15}$, $R_{17}$, $R_{21}$, $R_{23}$, $R_{28}$, and $R_{30}$ in Formula 2B may each independently be selected from a cyano group and groups represented by Formulae 4-1 to 4-29, or $R_{17}$ in Formula 2C may be a cyano group, a phenyl group, a biphenyl group or a terphenyl group, but they are not limited thereto.

According to some embodiments, at least one of $R_{23}$, $R_{25}$, and $R_{15}$ to $R_{17}$ in Formula 2A may each independently be selected from a cyano group and groups represented by Formulae 4-1 to 4-29, and the other substituents in Formula 2A may all be hydrogen or deuterium, or at least one of $R_{15}$, $R_{17}$, $R_{21}$, $R_{23}$, $R_{28}$ and $R_{30}$ in Formula 2B may each independently be selected from a cyano group and groups represented by Formulae 4-1 to 4-29, and the other substituents in Formula 2B may all be hydrogen or deuterium, but they are not limited thereto.

In various embodiments, i) at least one of $R_{17}$ and $R_{25}$ in Formula 2A-1, ii) at least one of $R_{17}$ and $R_{25}$ in Formula 2A-2, iii) $R_{17}$ in Formula 2A-3, and
iv) $R_{17}$ in Formula 2A-4 may each independently be selected from
deuterium and a cyano group; and
a phenyl group, a biphenyl group, and a terphenyl group, each substituted with at least one selected from deuterium, a cyano group, and a phenyl group.

In various embodiments,
i) at least one of $R_{17}$ and $R_{25}$ in Formula 2A-1,
ii) at least one of $R_{17}$ and $R_{25}$ in Formula 2A-2,
iii) $R_{17}$ in Formula 2A-3, and
iv) $R_{17}$ in Formula 2A-4 may each independently be selected from a cyano group and groups represented by Formulae 4-1 to 4-29. Alternatively, $R_{11}$ to $R_{17}$ and $R_{21}$ to $R_{25}$ in Formulae 2A-1 to 2A-4 may all be hydrogen.

In various embodiments,
i) $R_{17}$ in Formula 2B-1,
ii) $R_{17}$ in Formula 2B-2,
iii) one of $R_{17}$ and $R_{28}$ in Formula 2B-3,
iv) one of $R_{17}$ and $R_{28}$ in Formula 2B-4,
v) one of $R_{23}$, $R_{28}$, and $R_{30}$ in Formula 2B-5, and
vi) one of $R_{23}$, $R_{28}$, and $R_{30}$ in Formula 2B-6 may each independently be selected from
deuterium and a cyano group; and
a phenyl group, a biphenyl group, and a terphenyl group, each substituted with at least one selected from deuterium, a cyano group, and a phenyl group.

In various embodiments,
i) $R_{17}$ in Formula 2B-1,
ii) $R_{17}$ in Formula 2B-2,
iii) one of $R_{17}$ and $R_{28}$ in Formula 2B-3,
iv) one of $R_{17}$ and $R_{28}$ in Formula 2B-4,
v) one of $R_{23}$, $R_{28}$, and $R_{30}$ in Formula 2B-5, and
vi) one of $R_{23}$, $R_{28}$, and $R_{30}$ in Formula 2B-6 may each independently be selected from a cyano group and groups represented by Formulae 4-1 to 4-29, but are not limited thereto. Alternatively, each of $R_{11}$ to $R_{17}$, $R_{21}$ to $R_{24}$, and $R_{26}$ to $R_{30}$ in Formulae 2B-1 to 2B-6 may simultaneously be hydrogen.

The number of cyano groups in each of Formulae 2A to 2C may be 1, 2, 3, or 4, for example, 2 or 3.

The number of cyano groups in Formula 1 may be 2, 3, or 4, or 2 or 3.

A difference between a triplet ($T_1$) energy level and a singlet ($S_1$) energy level of the condensed cyclic compound represented by Formula 1 may be in a range of 0.1 electron Volts (eV) to 0.6 eV. Accordingly, an electronic device (for example, an organic light-emitting device) including the condensed cyclic compound represented by Formula 1 may have an increased stability. Thus, the electronic device (for example, the organic light-emitting device) may have high efficiency and a long lifespan. In addition, the condensed cyclic compound represented by Formula 1 may be used as a thermally activated delayed fluorescence (TADF) emitter.

The triplet ($T_1$) energy level of the condensed cyclic compound represented by Formula 1 may be 2.9 eV to 3.1 eV. Accordingly, the condensed cyclic compound may be appropriately used as a host for emitting blue light of a high color purity.

According to an exemplary embodiment, the condensed cyclic compound represented by Formula 1 may be selected from Compounds 1 to 116 below:

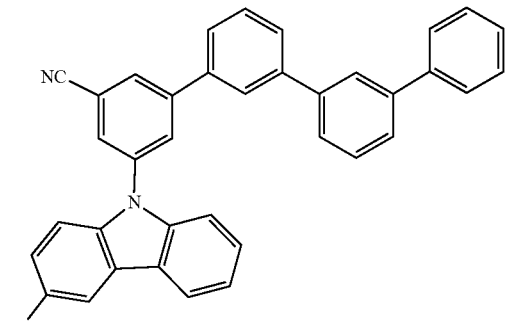

1

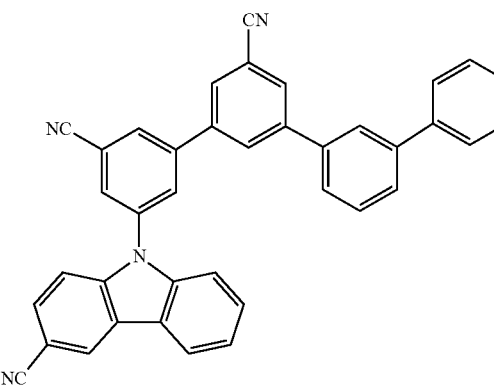

2

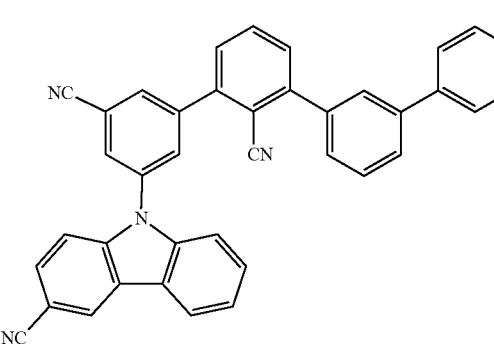

3

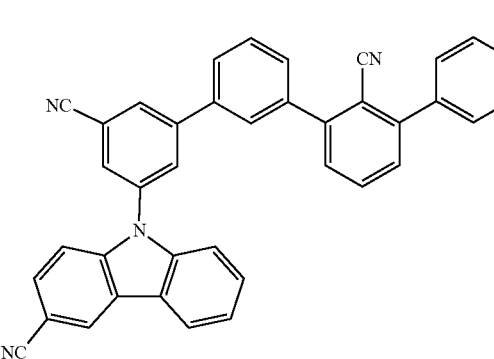

4

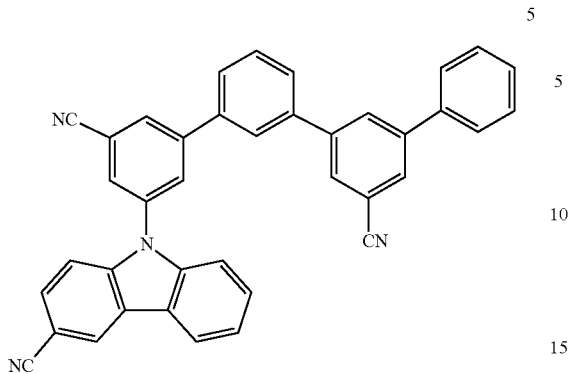
5
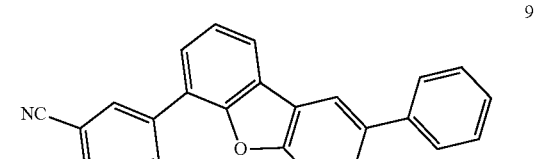
9
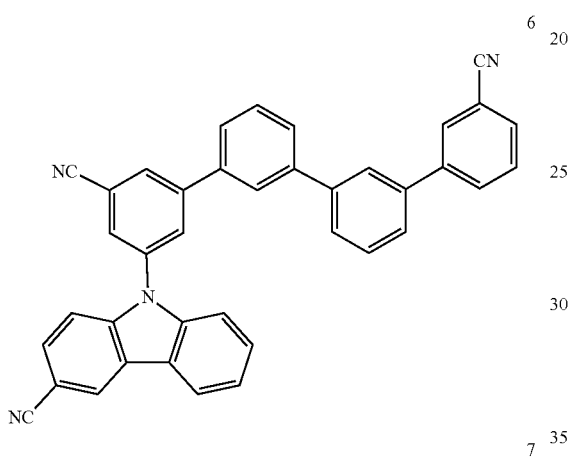
6
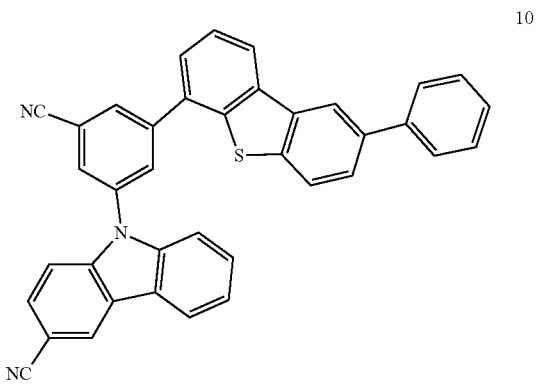
10
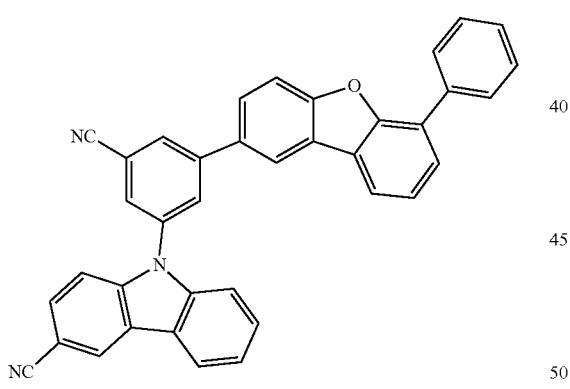
7
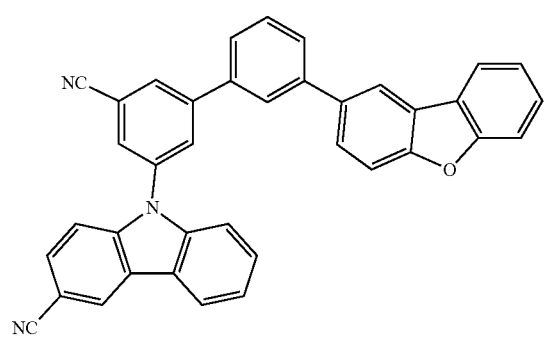
11
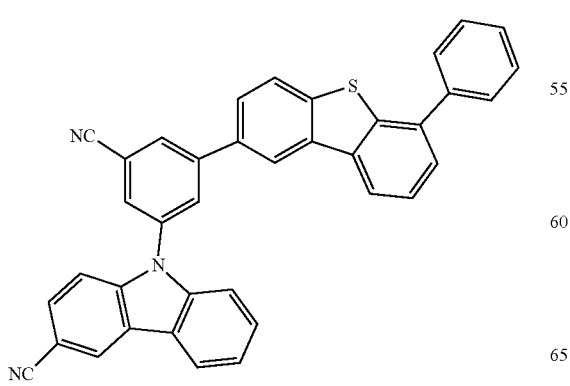
8
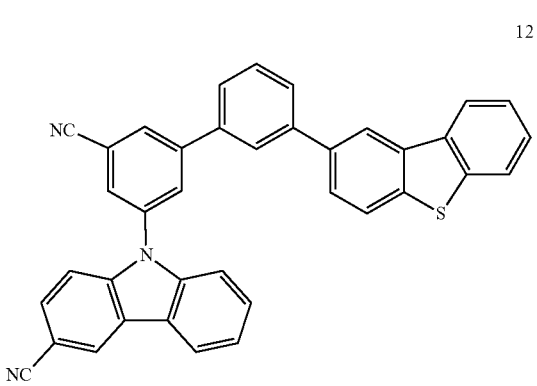
12

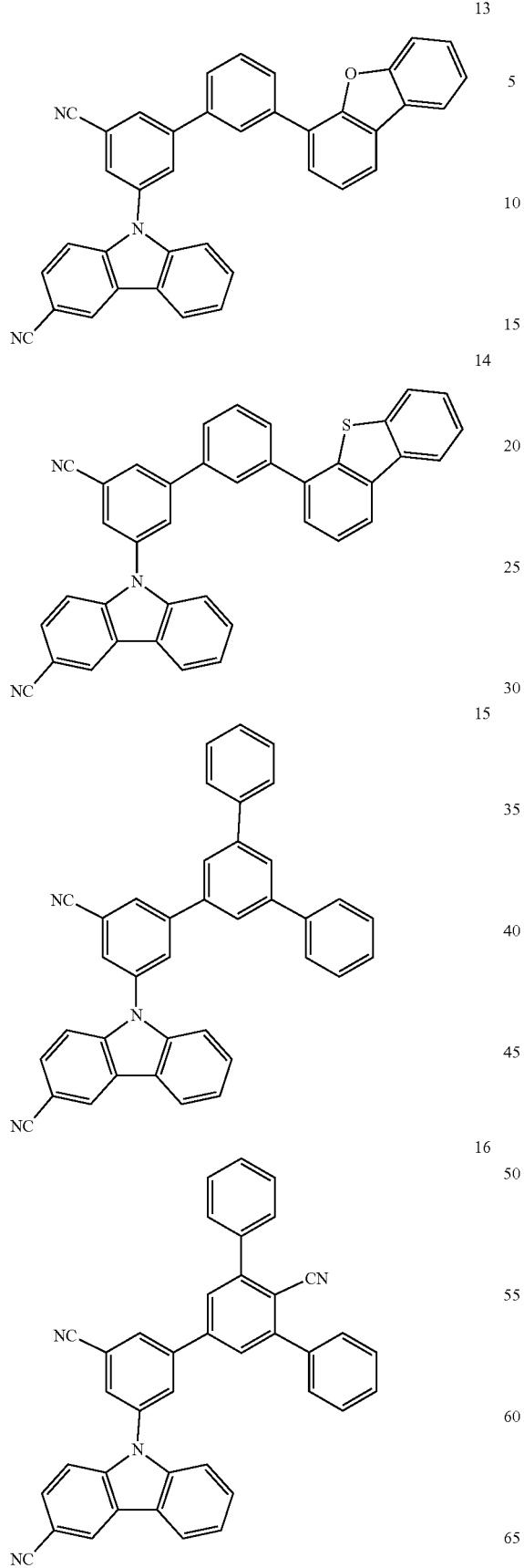
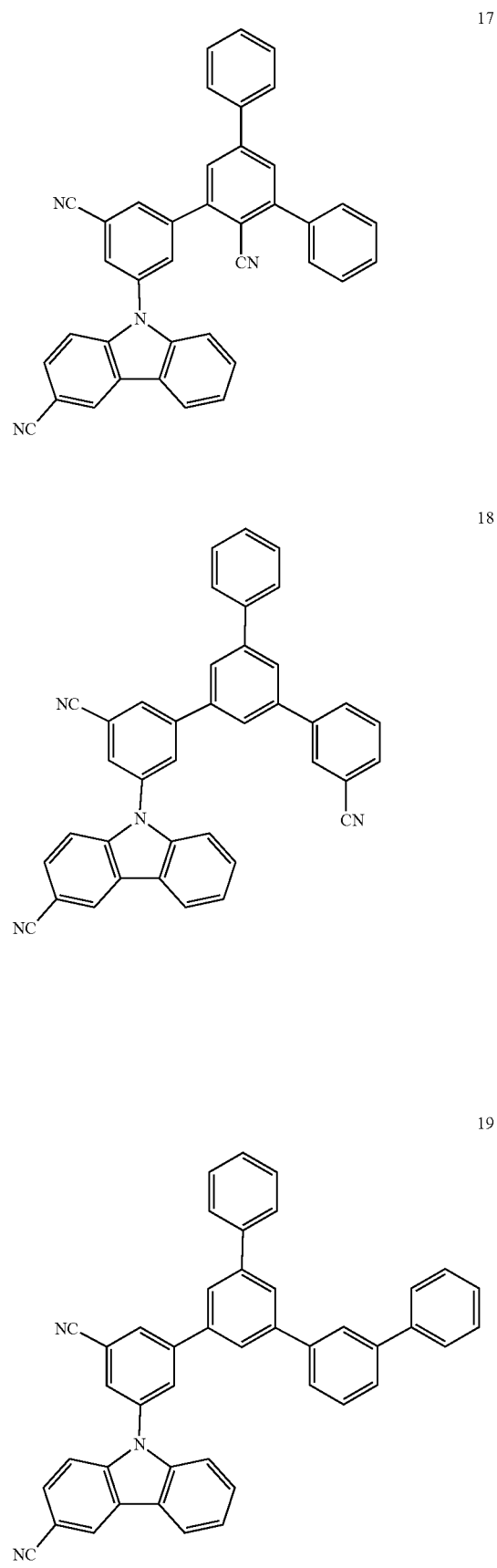

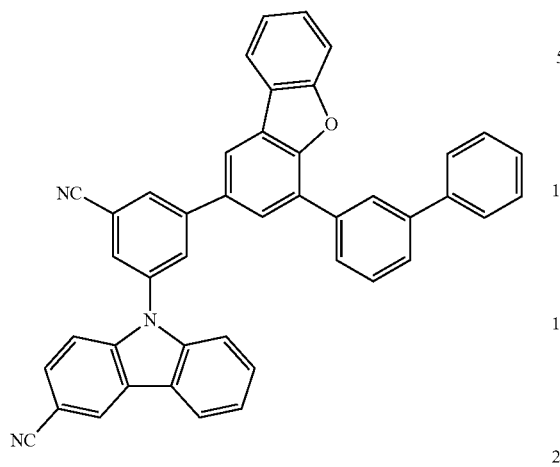
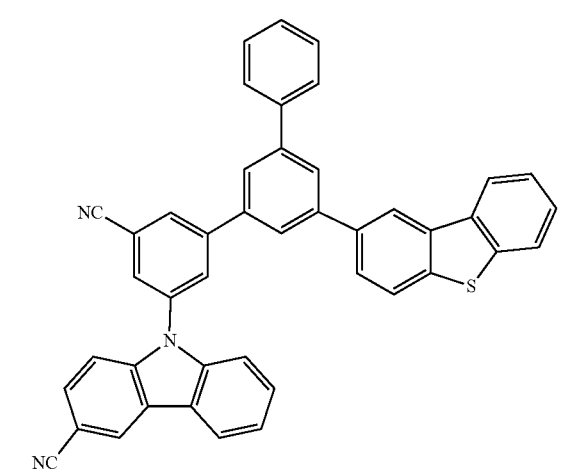
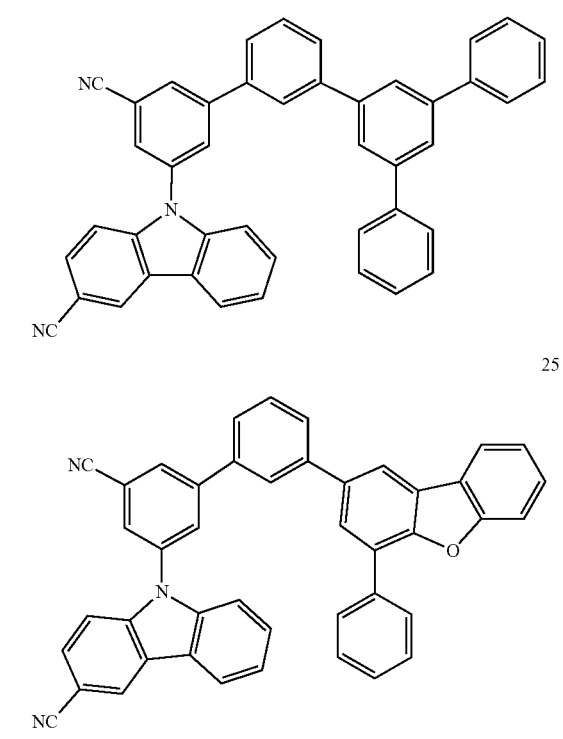
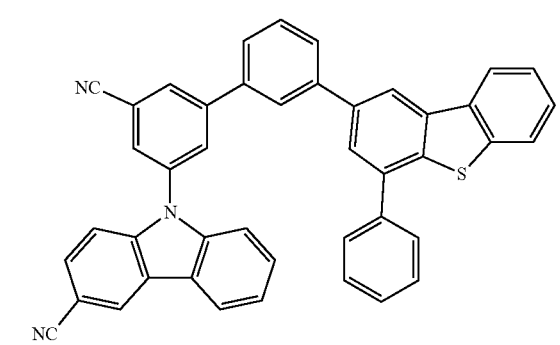

27
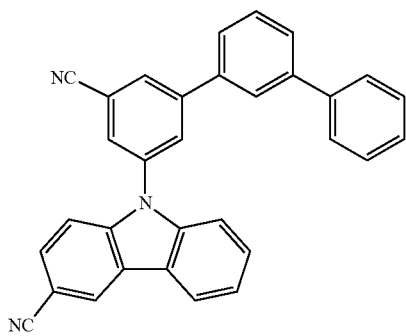
28
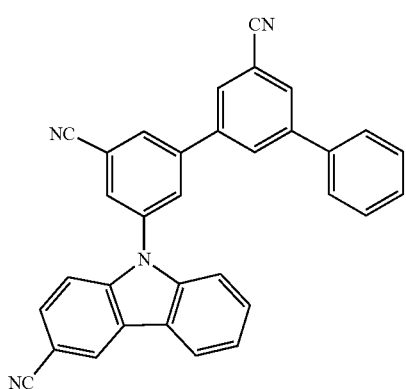
29
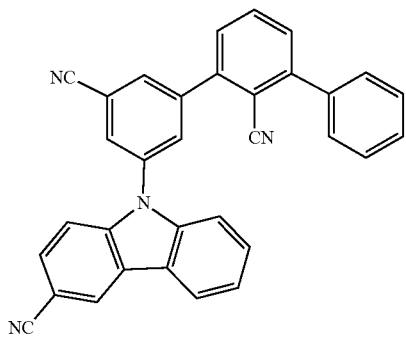
30
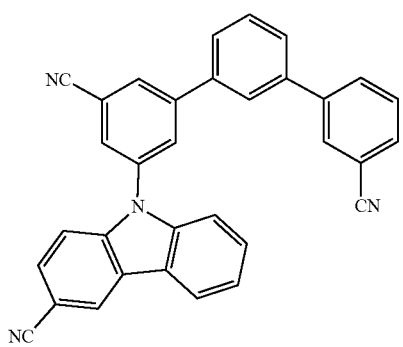
31
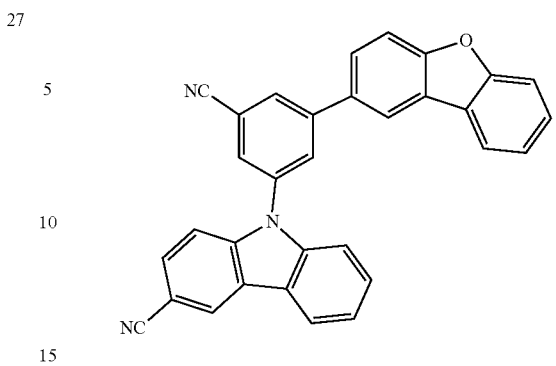
32
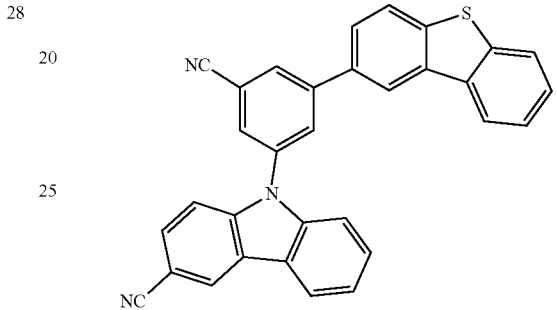
33
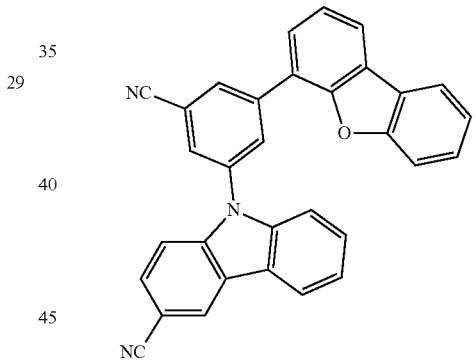
34
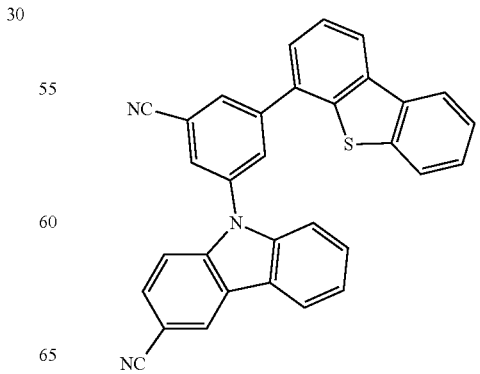

35
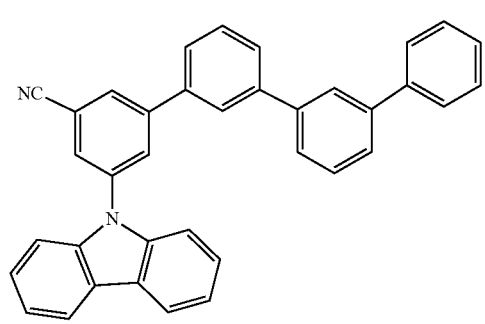
36
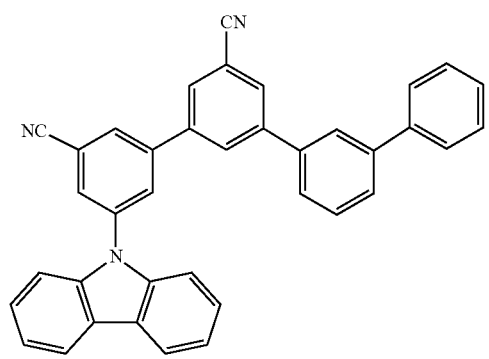
37
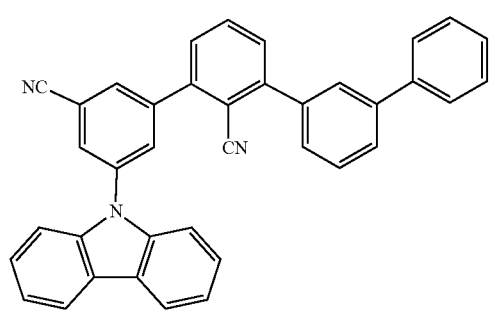
38
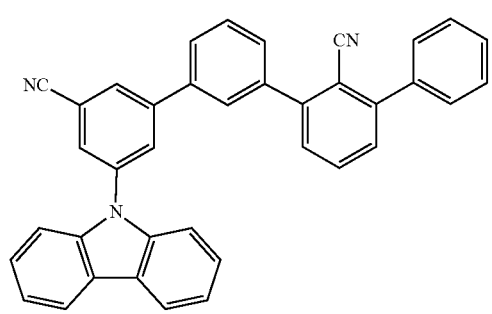
39
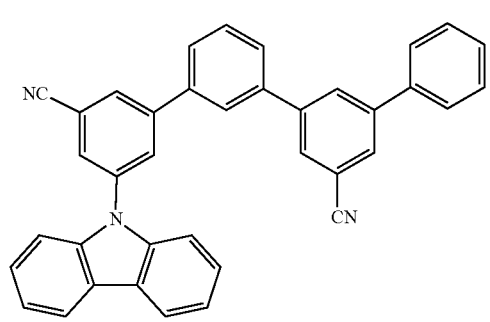
40
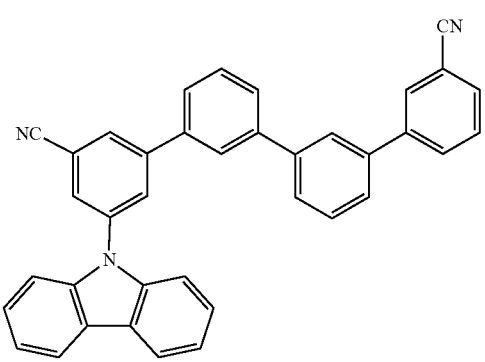
41
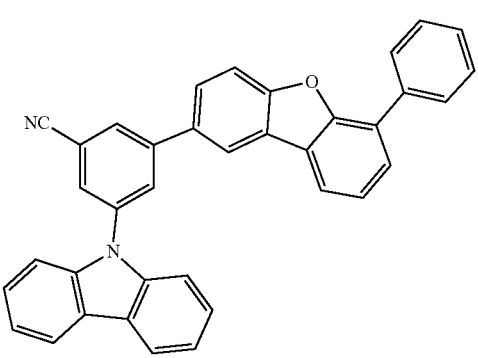
42
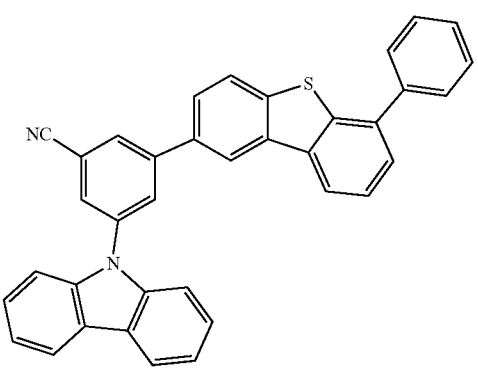
43
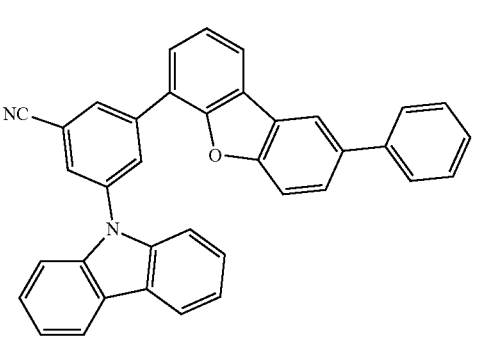

44
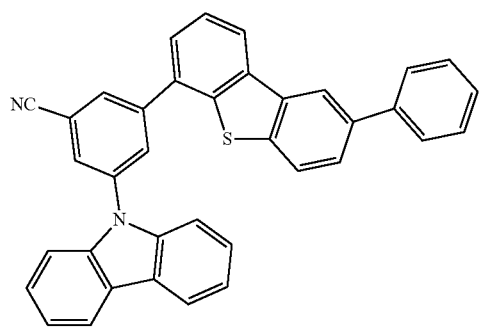
45
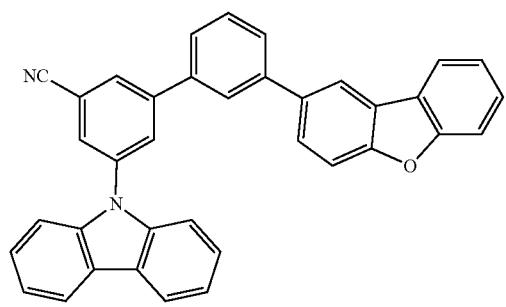
46
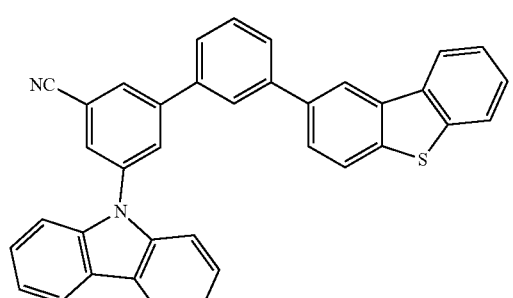
47
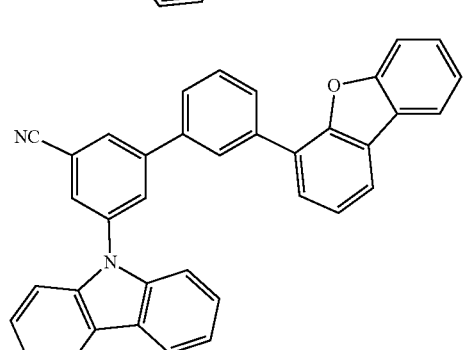
48
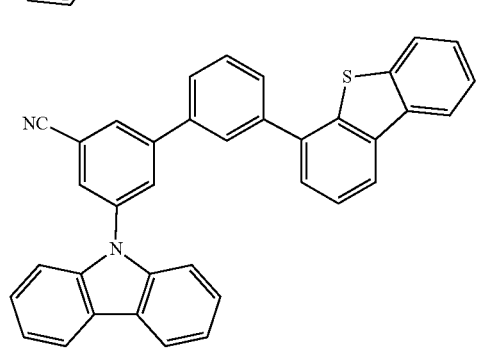
49
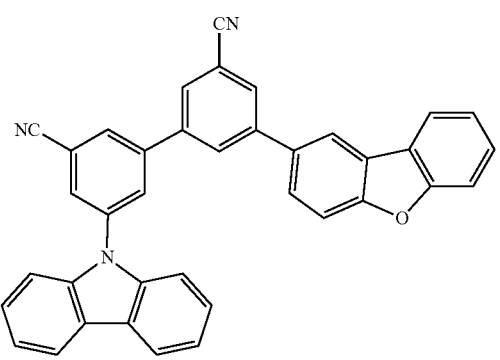
50
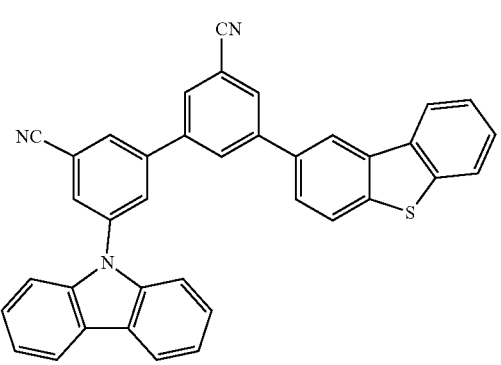
51
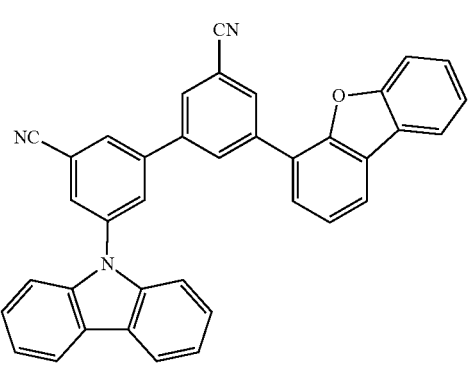
52
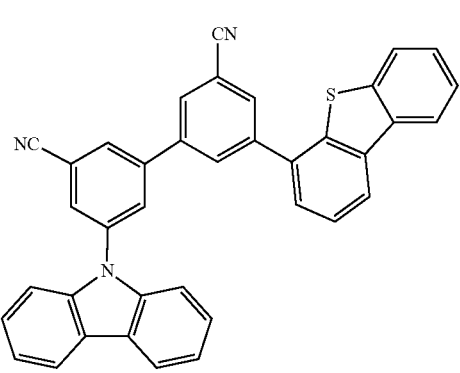

53
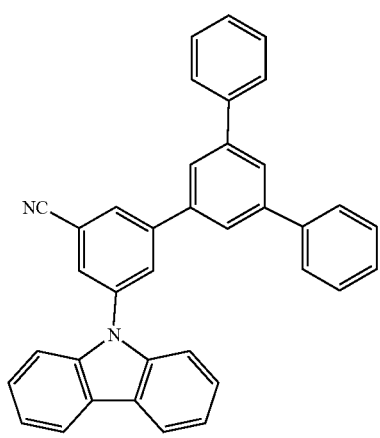
54
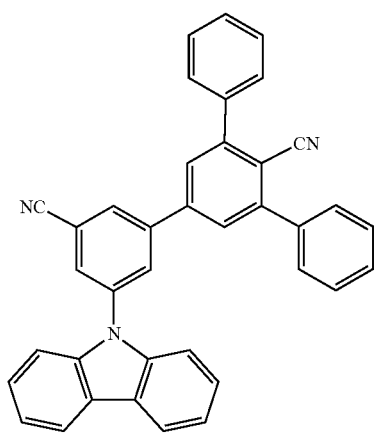
55
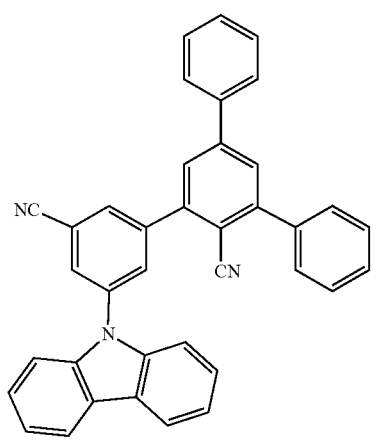
56
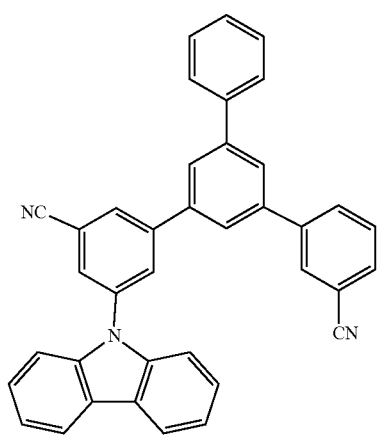
57
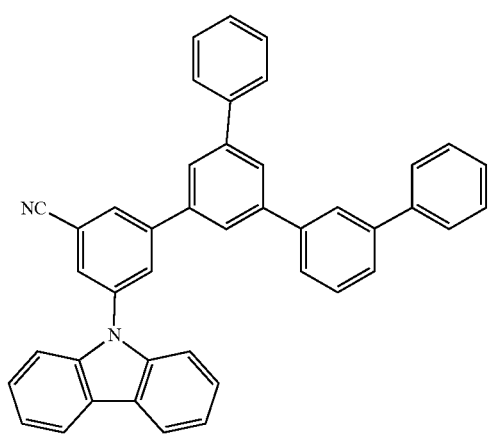
58
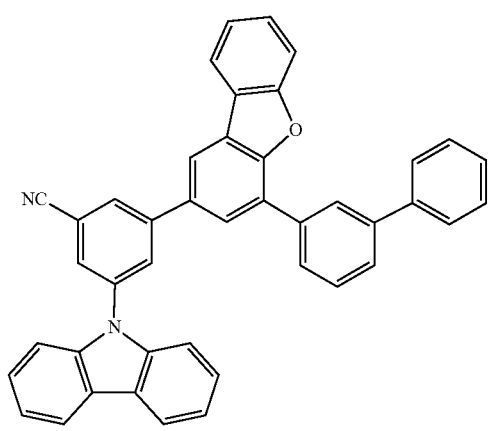

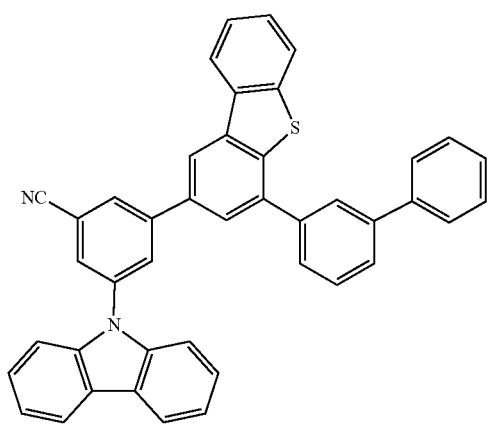
59
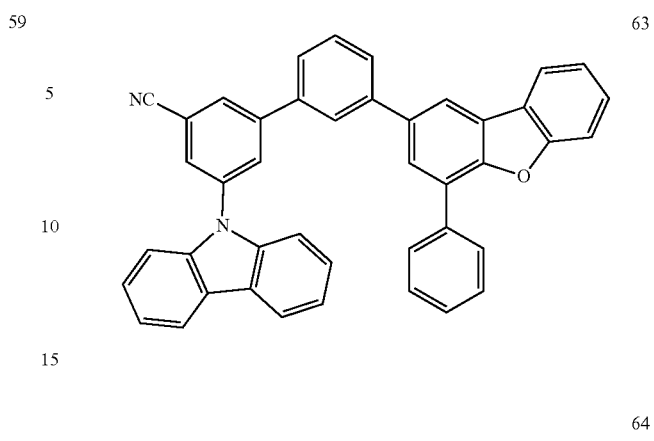
63
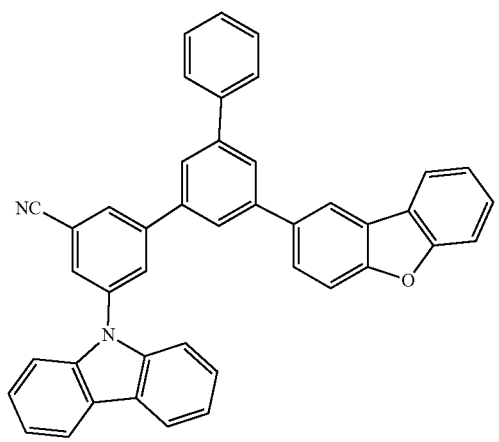
60
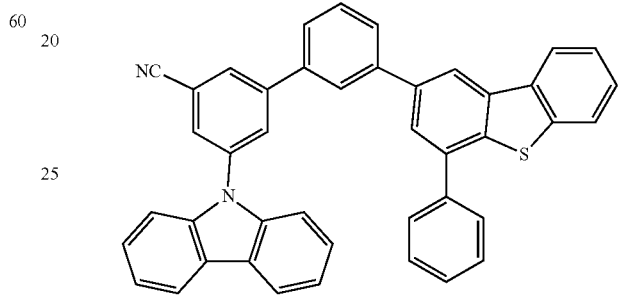
64
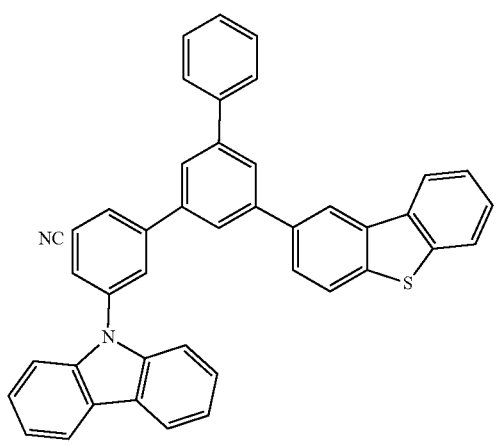
61
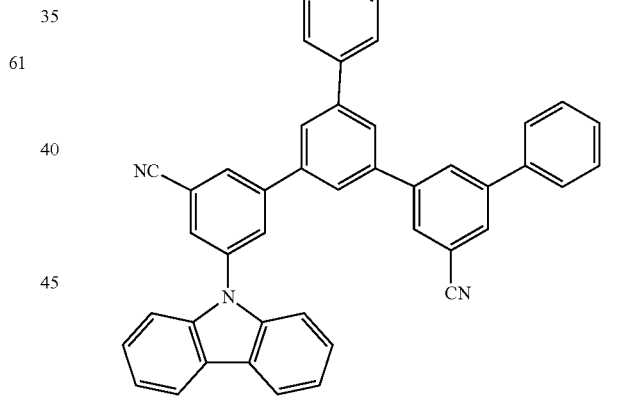
65
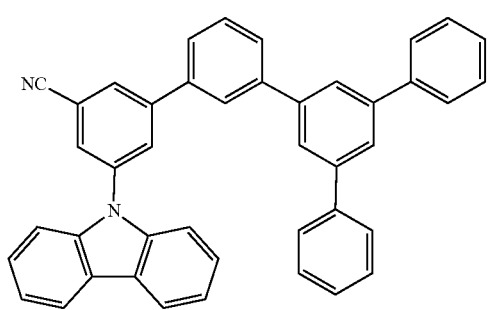
62
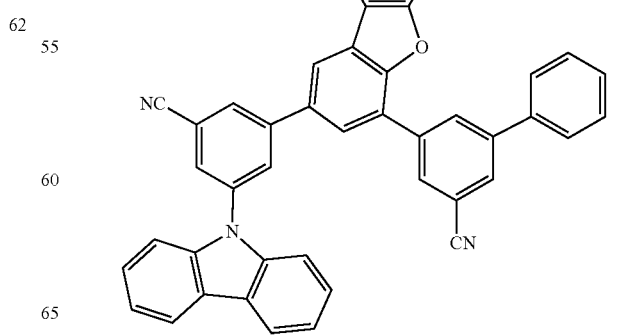
66

67
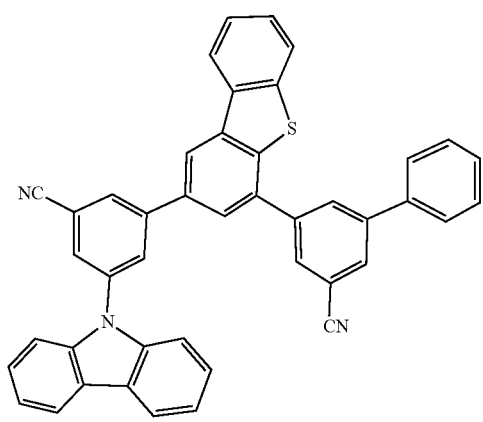
68
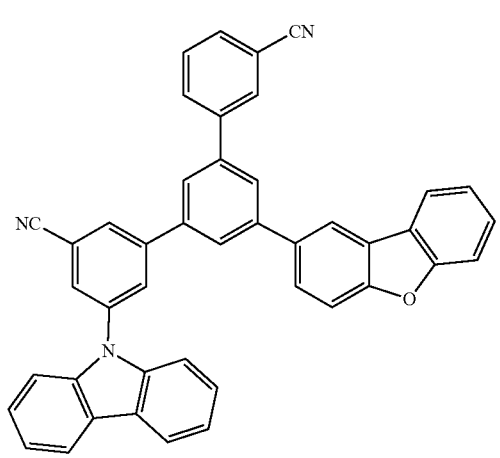
69
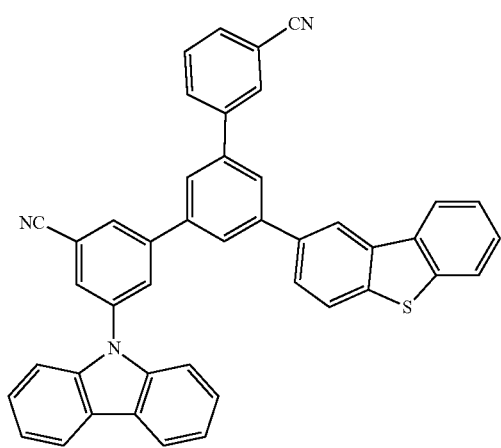
70
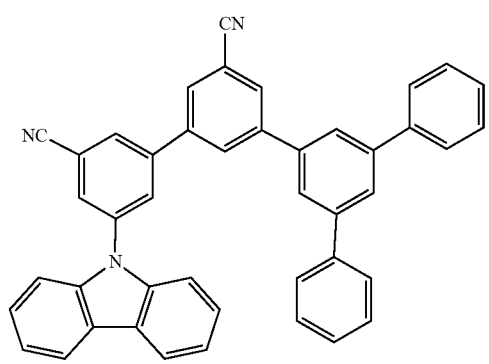
71
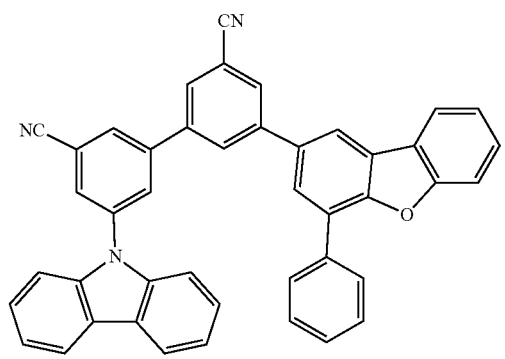
72
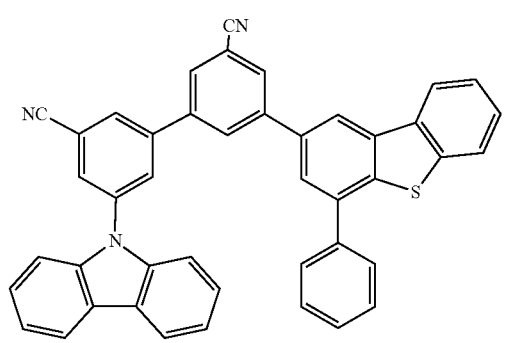
73
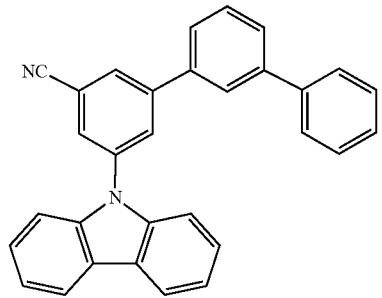

74
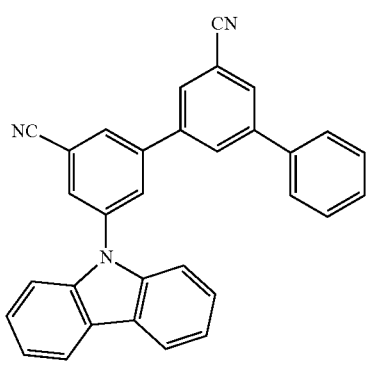
75
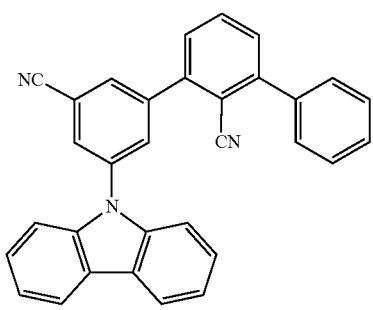
76
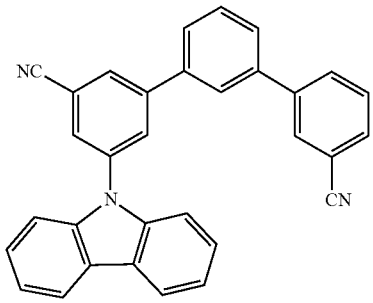
77
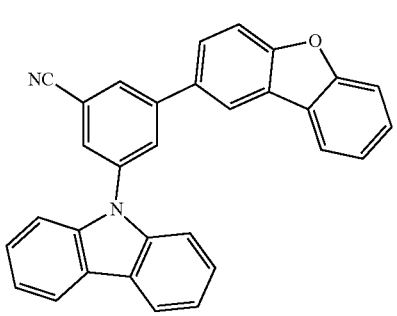
78
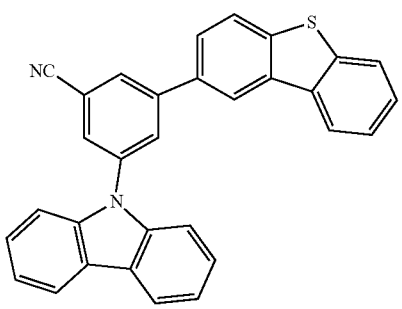
79
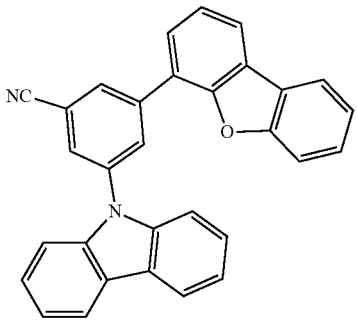
80
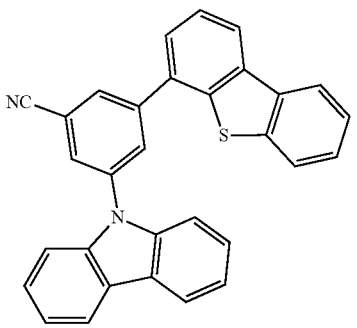
81
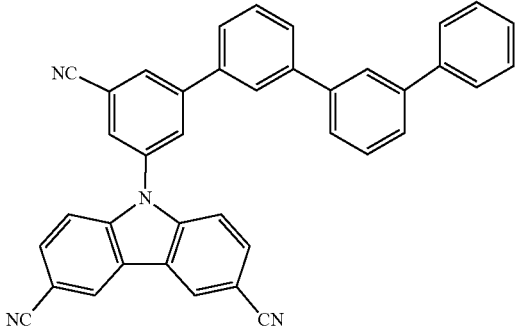
82
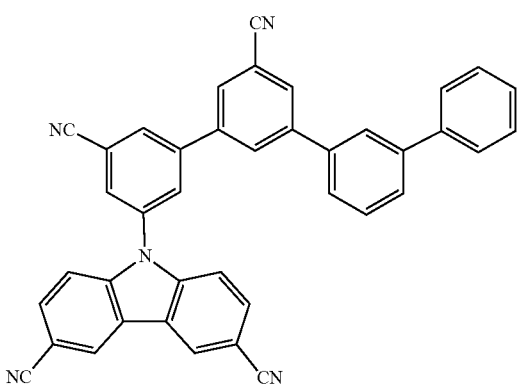

-continued
83
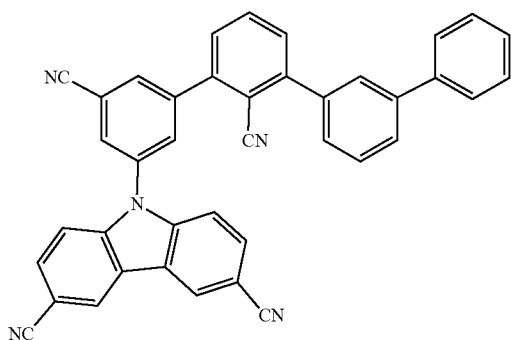
84
85
86
-continued
87
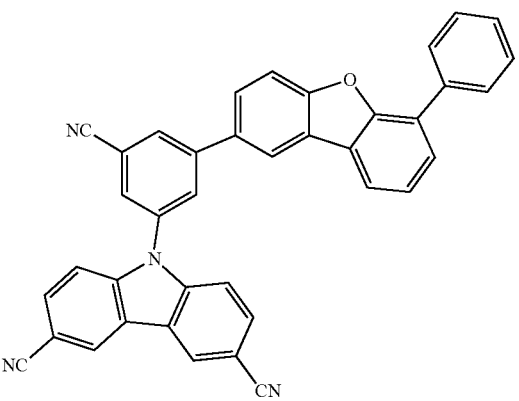
88
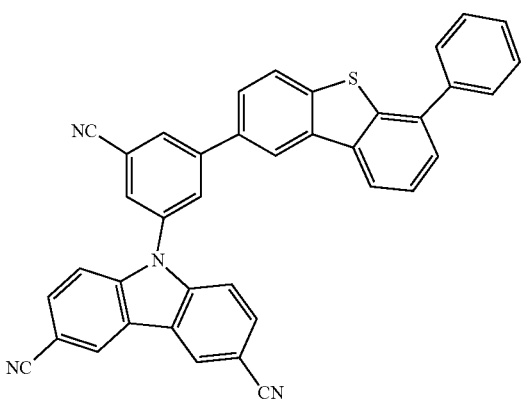
89
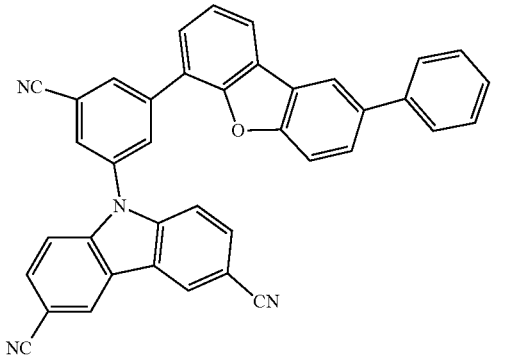
90
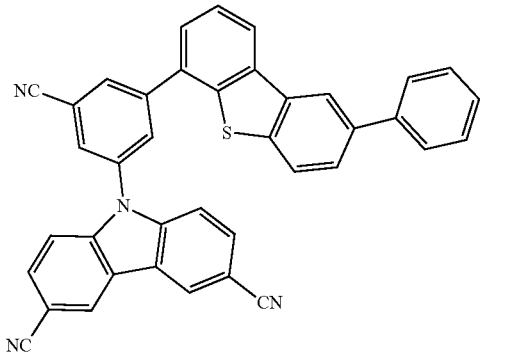

91
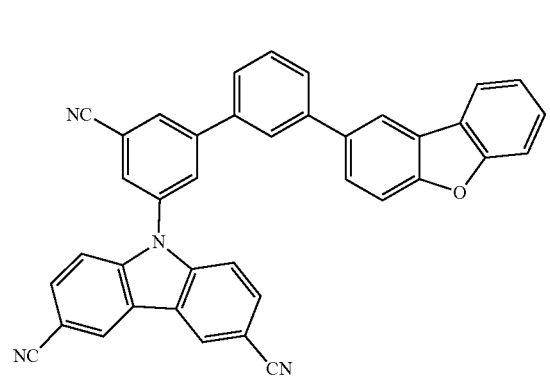
92
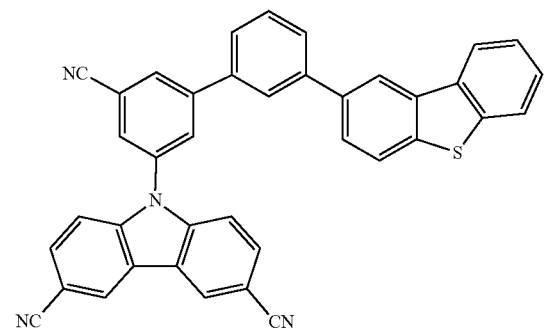
93
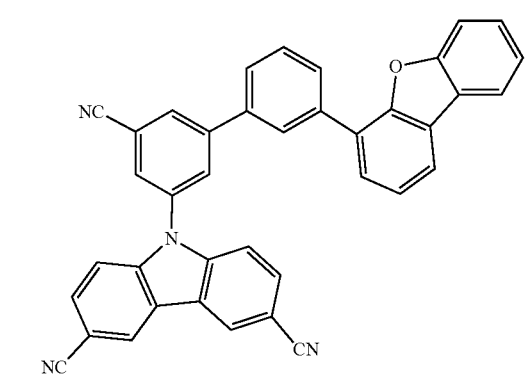
94
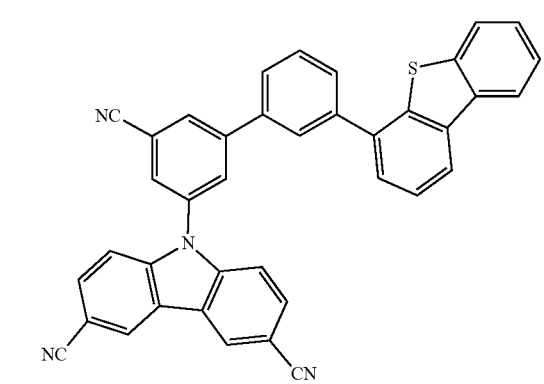
95
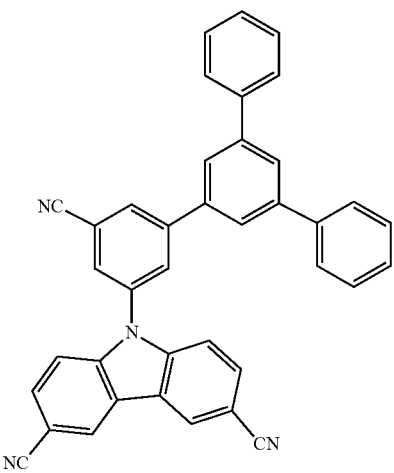
96
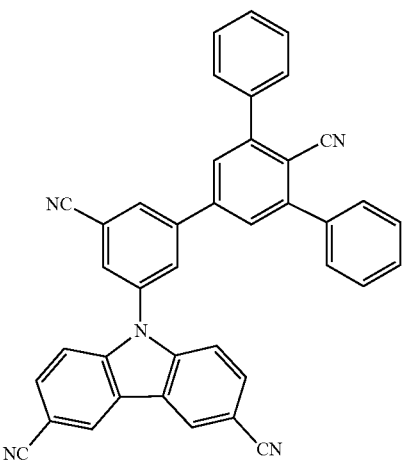
97
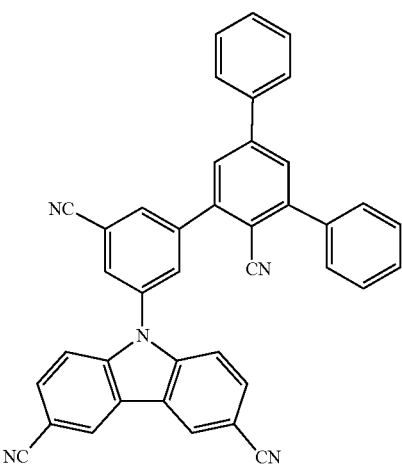

98
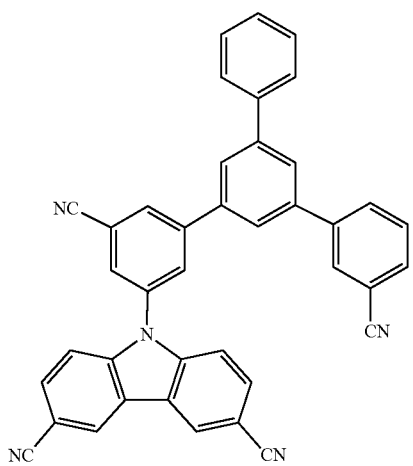
99
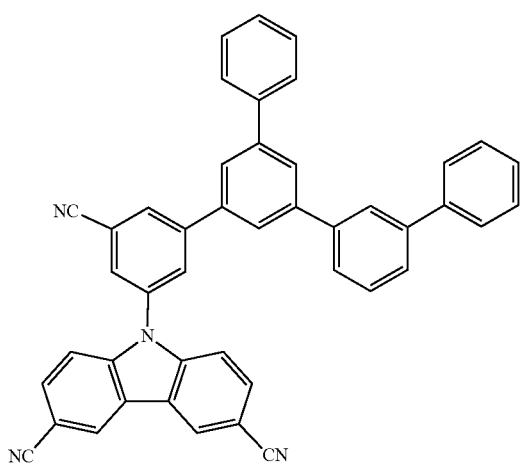
100
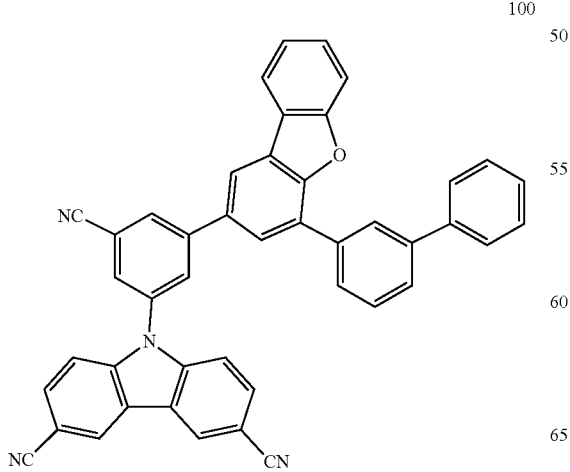
101
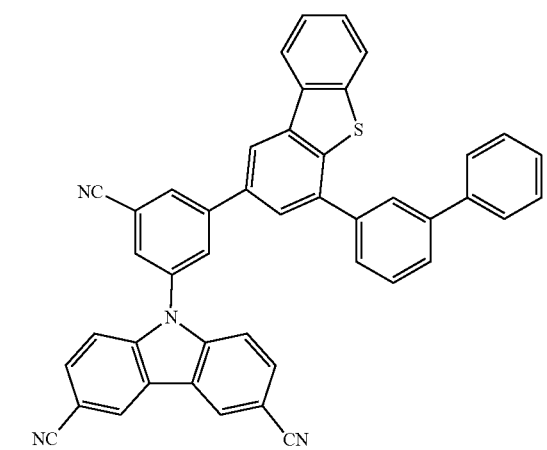
102
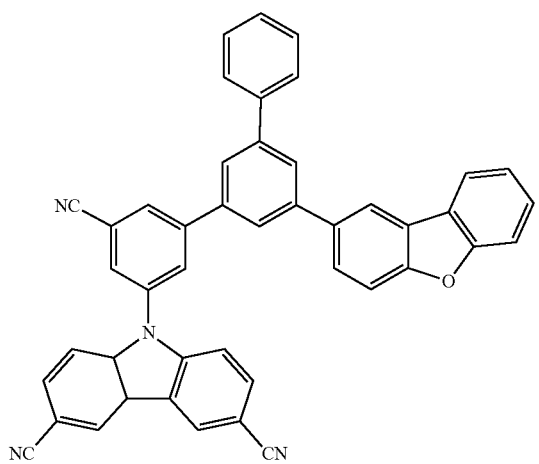
103
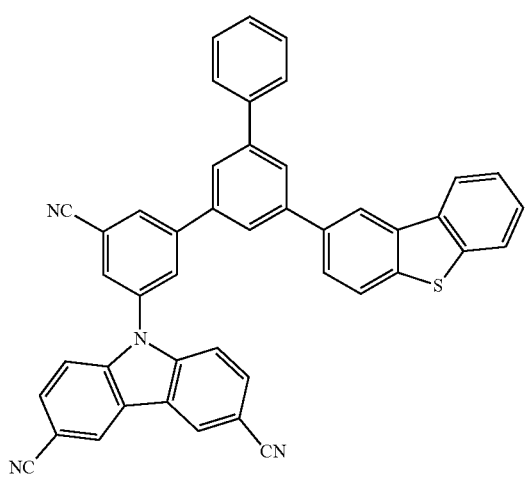

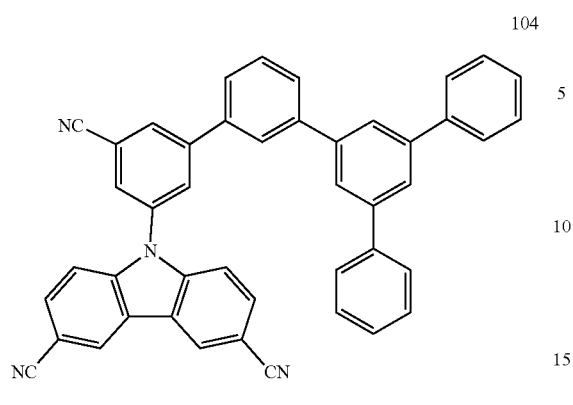
104
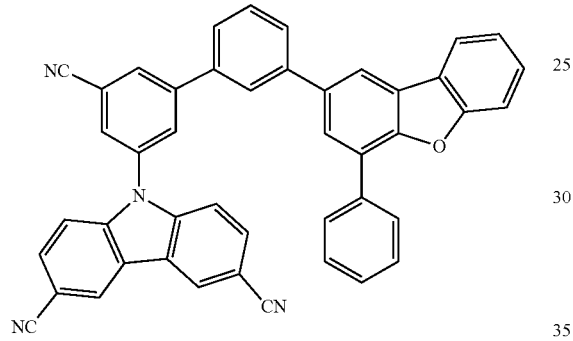
105
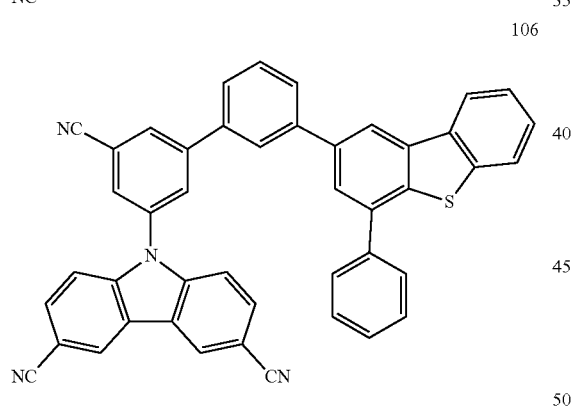
106
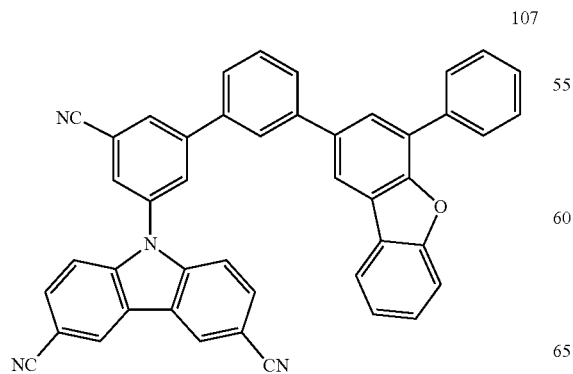
107
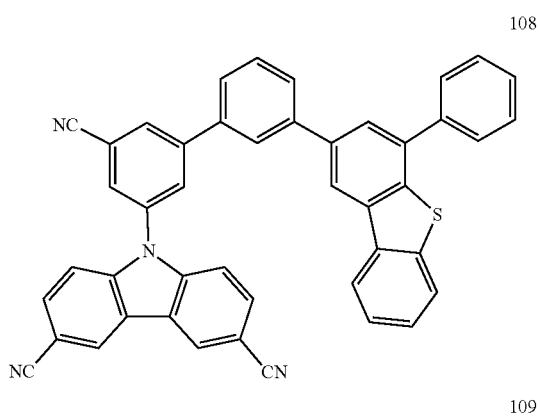
108
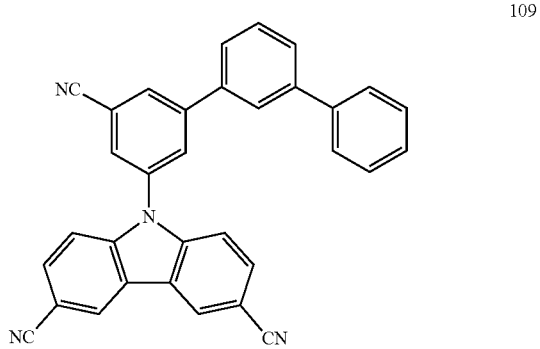
109
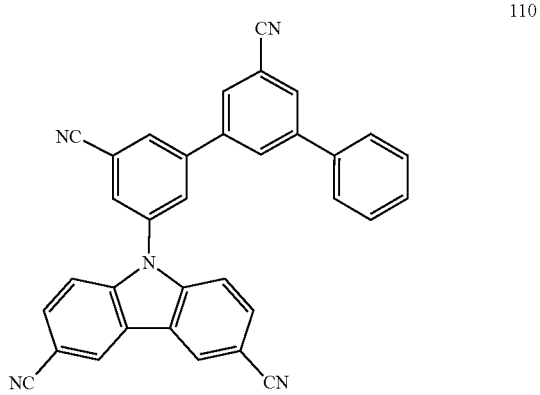
110
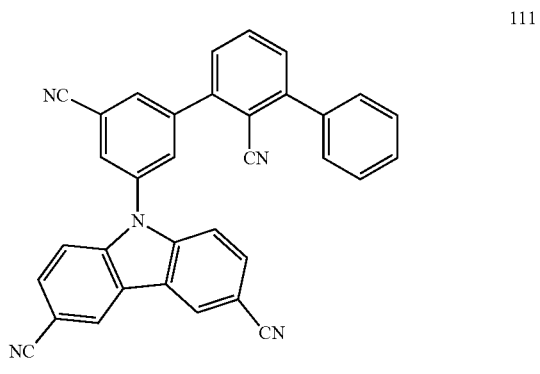
111

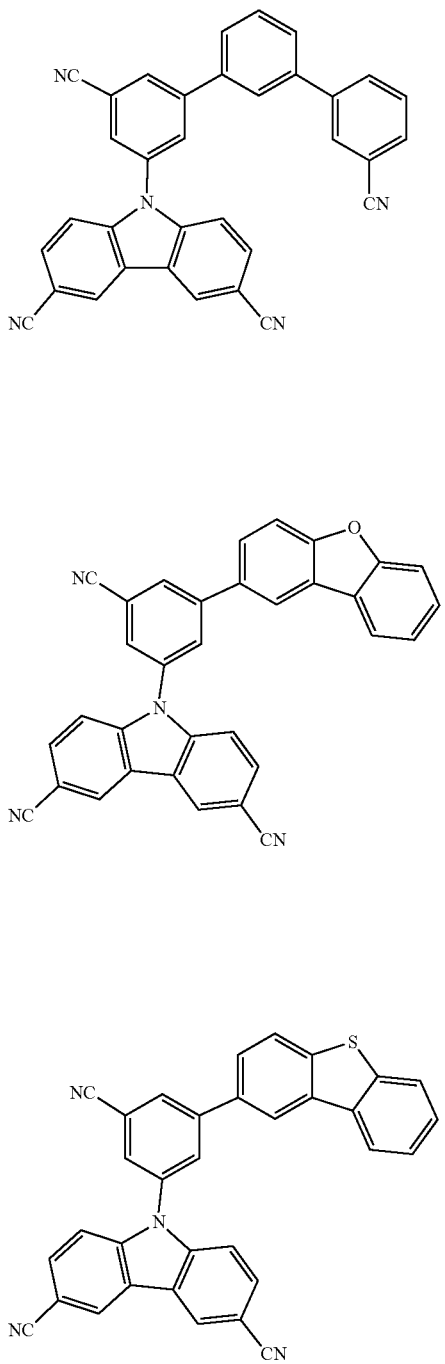

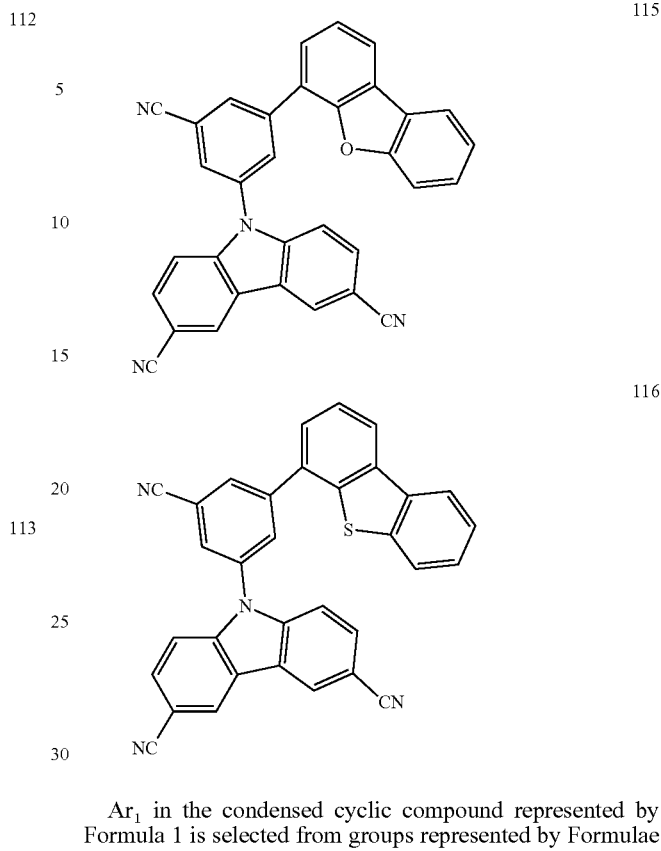

Ar₁ in the condensed cyclic compound represented by Formula 1 is selected from groups represented by Formulae 2A to 2C, and Formulae 2A to 2C include at least one cyano group. Furthermore, Formulae 2A to 2C include two or more phenylene groups or derivatives thereof, linked to each other in meta-position. Accordingly, the condensed cyclic compound represented by Formula 1 may have a relatively high triplet ($T_1$) energy level, and a relatively low energy band gap between a highest occupied molecular orbital (HOMO) and a lowest unoccupied molecular orbital (LUMO) to thereby contribute to easy transportation of holes and electrons. Also, by introducing at least one cyano group to Formulae 2A to 20, the condensed cyclic compound may maintain a high triplet ($T_1$) and have excellent heat resistance with respect to molecular weight. Accordingly, an electronic device including the condensed cyclic compound, for example, an organic light-emitting device including the condensed cyclic compound may have a high efficiency and a long lifespan.

A HOMO energy level, a LUMO energy level, a triplet ($T_1$) energy level, and a singlet ($S_1$) energy level, and a difference between $T_1$ and $S_1$ of Compounds 1 to 16 and Compound B were evaluated by using a Density Functional Theory (DFT) method of a Gaussian program structure-optimized at the level of B3LYP/6-31 G(d,p). Results thereof are shown in Table 1:

TABLE 1

| Compound No. | HOMO (eV) | LU MO (eV) | $T_1$ (eV) | $S_1$ (eV) | $S_1 - T_1$ |
|---|---|---|---|---|---|
| 1 | −5.648 | −1.811 | 2.992 | 3.243 | 0.251 |
| 2 | −5.777 | −2.335 | 2.975 | 3.108 | 0.133 |
| 3 | −6.175 | −2.232 | 3.001 | 3.361 | 0.360 |
| 4 | −6.067 | −1.958 | 3.037 | 3.507 | 0.470 |
| 5 | −6.068 | −1.958 | 3.012 | 3.508 | 0.496 |
| 6 | −6.065 | −1.948 | 3.001 | 3.516 | 0.515 |
| 7 | −6.071 | −1.966 | 3.036 | 3.505 | 0.469 |

TABLE 1-continued

| Compound No. | HOMO (eV) | LUMO (eV) | $T_1$ (eV) | $S_1$ (eV) | $S_1 - T_1$ |
|---|---|---|---|---|---|
| 8 | −6.068 | −1.938 | 3.043 | 3.526 | 0.483 |
| 9 | −5.989 | −1.94 | 3.014 | 3.515 | 0.501 |
| 10 | −6.064 | −1.98 | 2.991 | 3.485 | 0.494 |
| 11 | −6.041 | −1.918 | 2.958 | 3.526 | 0.568 |
| 12 | −6.055 | −1.958 | 2.916 | 3.499 | 0.583 |
| 13 | −6.071 | −1.966 | 3.036 | 3.505 | 0.469 |
| 14 | −5.989 | −1.94 | 3.014 | 3.515 | 0.501 |
| 15 | −6.059 | −1.967 | 2.9 | 3.494 | 0.594 |
| 16 | −5.998 | −1.977 | 3.001 | 3.501 | 0.500 |
| B | −5.652 | −2.065 | 2.839 | 3.187 | 0.348 |

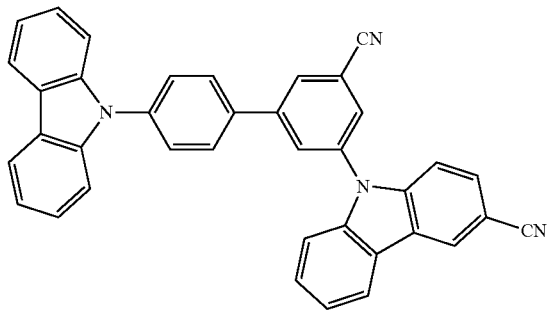

B

Referring to Table 1, as Compounds 1 to 16 have a higher $T_1$ energy level than Compound B including phenylene groups linked in para-position, one can see that Compounds 1 to 16 are suitable for a material to be used in an electronic device, for example, in an organic light-emitting device (e.g., as a host in an emission layer).

A method of synthesizing the condensed cyclic compound represented by Formula 1 may be understood by one of ordinary skill in the art by referring to Synthesis Examples described below.

Therefore, the condensed cyclic compound represented by Formula 1 may be appropriate to be used in an organic layer of an organic light-emitting device, for example as a host in an emission layer of the organic layer or as an emitter (for example, a TADF emitter). Thus, according to another aspect, provided is an organic light-emitting device that may include:
a first electrode;
a second electrode; and
an organic layer that is disposed between the first electrode and the second electrode,
wherein the organic layer includes an emission layer and at least one condensed cyclic compound represented by Formula 1.

Since the organic light-emitting device has an organic layer including the condensed cyclic compound represented by Formula 1, the organic light-emitting device may have a low driving voltage, high efficiency, high luminance, high quantum emission efficiency, and long lifespan.

The condensed cyclic compound represented by Formula 1 may be included between a pair of electrodes of the organic light-emitting device. In some embodiments, the condensed cyclic compound may be included in at least one selected from the emission layer, a hole transport region (for example, including a hole injection layer, a hole transport layer, an electron blocking layer, or any combination thereof) disposed between the first electrode and the emission layer, and an electron transport region (for example, including a hole blocking layer, an electron transport layer, an electron injection layer, or any combination thereof) disposed between the emission layer and the second electrode.

For example, the condensed cyclic compound represented by Formula 1 may be included in the emission layer. Here, the condensed cyclic compound included in the emission layer may serve as a host, and the emission layer may further include a dopant (a fluorescent dopant or a phosphorescent dopant). The emission layer may be a green emission layer that emits green light or a blue emission layer that emits blue light. According to an exemplary embodiment, the condensed cyclic compound represented by Formula 1 may be included in the emission layer, and the emission layer may further include a phosphorescent dopant, and the emission layer may emit blue light.

Alternatively, the condensed cyclic compound represented by Formula 1 may be included in the emission layer, and the condensed cyclic compound may be a TADF emitter. Here, the emission layer may include only the condensed cyclic compound represented by Formula 1 or may further include a host and/or a dopant in addition to the condensed cyclic compound represented by Formula 1.

As used herein, the expression the "(organic layer) includes at least one condensed cyclic compound" may be construed as meaning the "(organic layer) may include one condensed cyclic compound within the scope in Formula 1 or two or more different condensed cyclic compounds within the scope of Formula 1".

For example, the organic layer may include only Compound 1 as the condensed cyclic compound. In this regard, Compound 1 may be included in the emission layer of the organic light-emitting device. Alternatively, the organic layer may include Compound 1 and Compound 2 as the condensed cyclic compounds. In this regard, Compound 1 and Compound 2 may be included in the same layer (for example, both Compound 1 and Compound 2 may be included in the emission layer) or may be respectively included in different layers.

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:
  i) a hole transport region disposed between the first electrode and the emission layer, wherein the hole transport region includes a hole injection layer, a hole-transport layer, an electron blocking layer, or any combination thereof; and ii) an electron transport region disposed between the emission layer and the second electrode, wherein the electron transport region includes a hole blocking layer, an electron transport layer, an electron injection layer, or any combination thereof.

As used herein, the term the "organic layer" refers to a single and/or a plurality of layers disposed between the first electrode and the second electrode in an organic light-emitting device. The "organic layer" may include not only organic compounds but also organometallic complexes including metals.

The FIGURE is a schematic view of an organic light-emitting device 10 according to an exemplary embodiment. Hereinafter, a structure and a method of manufacturing the organic light-emitting device according to an exemplary embodiment will be described with reference to the FIGURE. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as a glass substrate or a transparent plastic substrate, each having excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function to facilitate hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag) may be used as the material for the first electrode 11.

The first electrode 11 may have a single layer structure or a multi-layer structure including two or more layers. For example, the first electrode 11 may have a triple-layer structure of ITO/Ag/ITO, but it is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer (HIL) may be formed on the first electrode 11 by using various methods such as vacuum-deposition, spin coating, casting, and Langmuir-Blodgett (LB) method.

When a hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, though the conditions may vary depending on a compound that is used as a hole injection material and a structure and thermal properties of a desired hole injection layer, but it is not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but is not limited thereto.

The conditions for forming a hole transport layer and an electron blocking layer may be understood based on the description of the conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

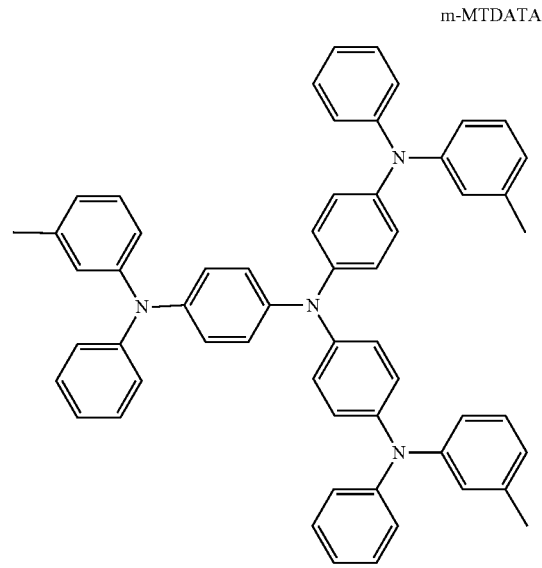

m-MTDATA

TDATA
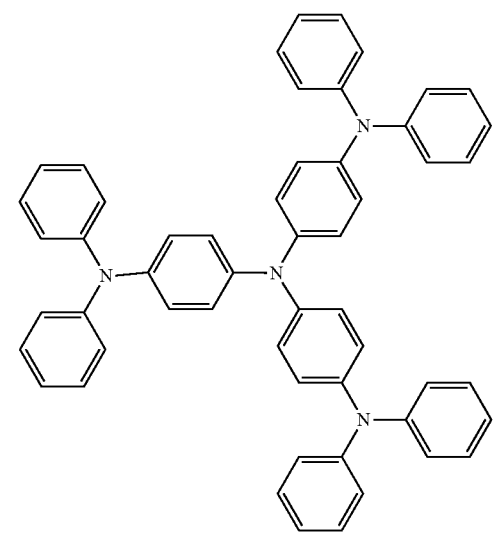
2-TNATA
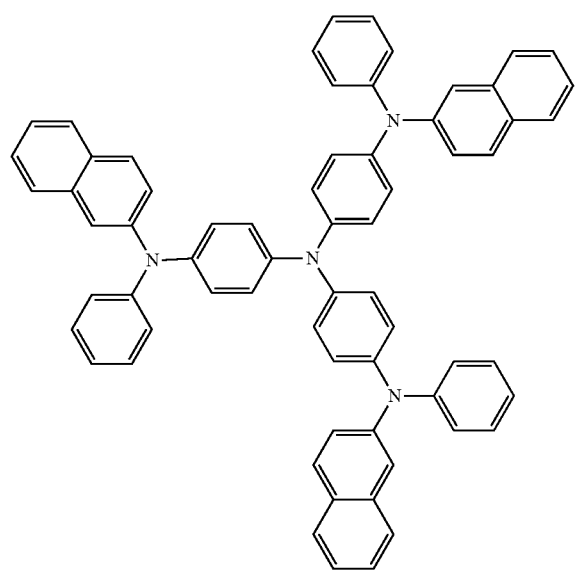
NPB
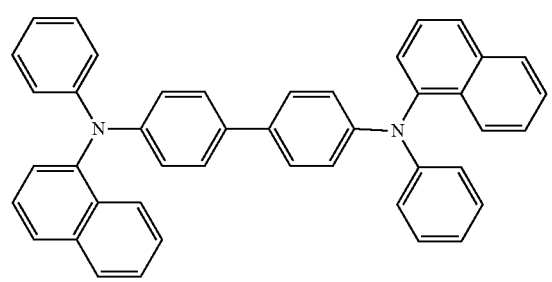
B-NPB
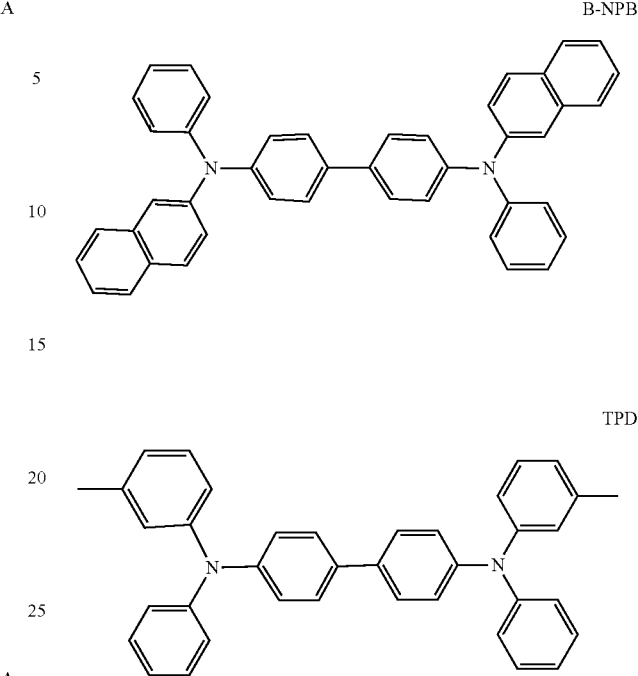
TPD
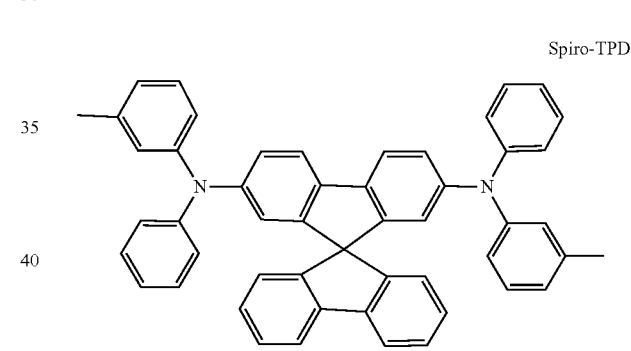
Spiro-TPD
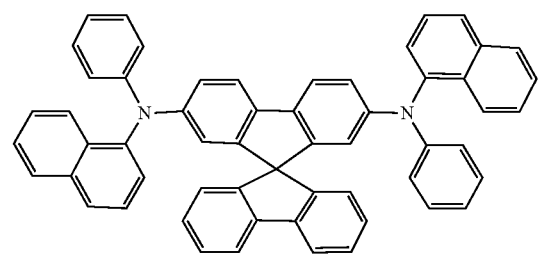
Spiro-NPB
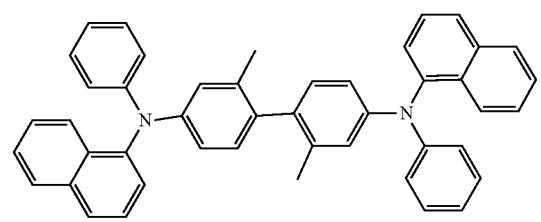
methylated NPB -continued

TAPC

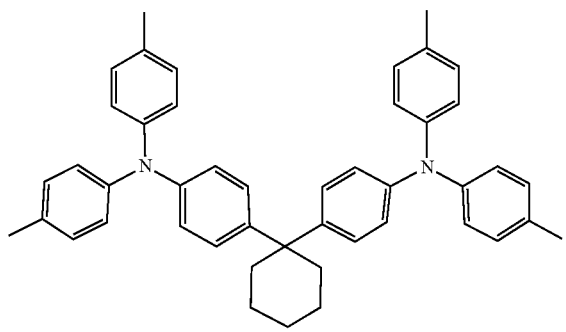

HMTPD

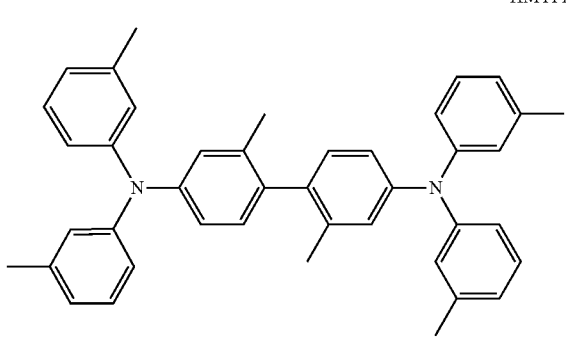

Formula 201

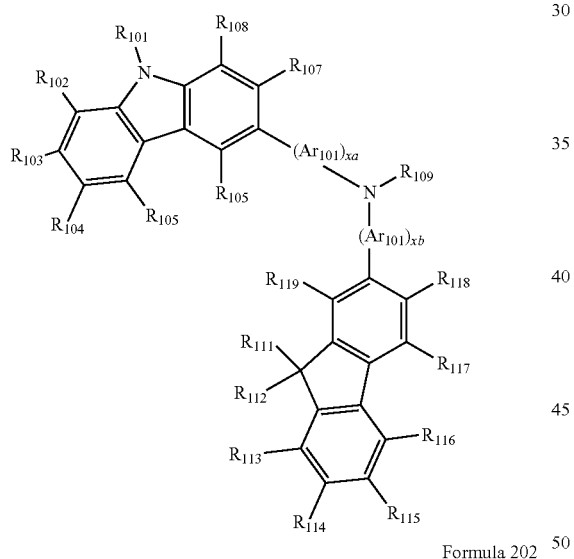

Formula 202

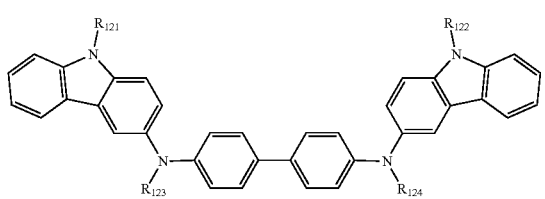

In Formula 201, $Ar_{101}$ and $Ar_{102}$ may each independently be selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer selected from 0 to 5, or may be 0, 1, or 2. For example, xa may be 1, and xb may be 0, but they are not limited thereto.

In Formulae 201 and 202, $R_{101}$ to $R_{108}$, $R_{111}$ to $R_{119}$, and $R_{121}$ to $R_{124}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, or a hexyl group), and a $C_1$-$C_{10}$ alkoxy group (for example, a methoxy group, an ethoxy group, a propoxy group, butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be selected from a phenyl group, a naphthyl group, an anthracenyl group and a pyridinyl group; and a phenyl group, a naphthyl group, an anthracenyl group, and a pyridinyl group, each substituted with at least selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an exemplary embodiment, the compound represented by Formula 201 may be represented by Formula 201A, but it is not limited thereto:

Formula 201A

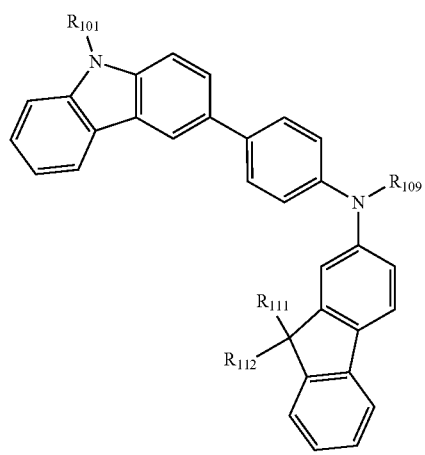

Descriptions for $R_{101}$, $R_{111}$, $R_{112}$, and $R_{109}$ in Formula 201A are the same as described above.

For example, the compound represented by Formula 201 and the compound represented by Formula 202 may include Compounds HT1 to HT20, but they are not limited thereto:

HT1

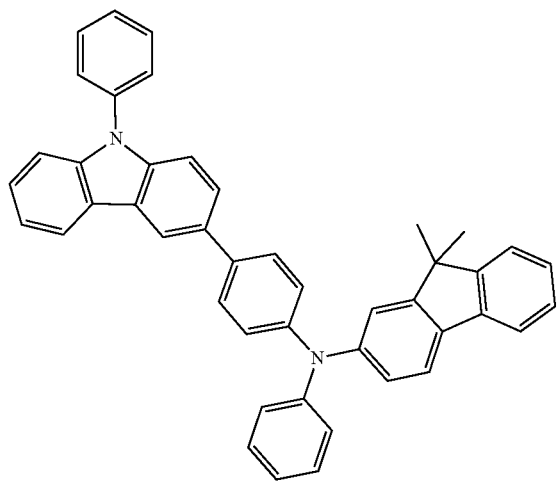

HT2

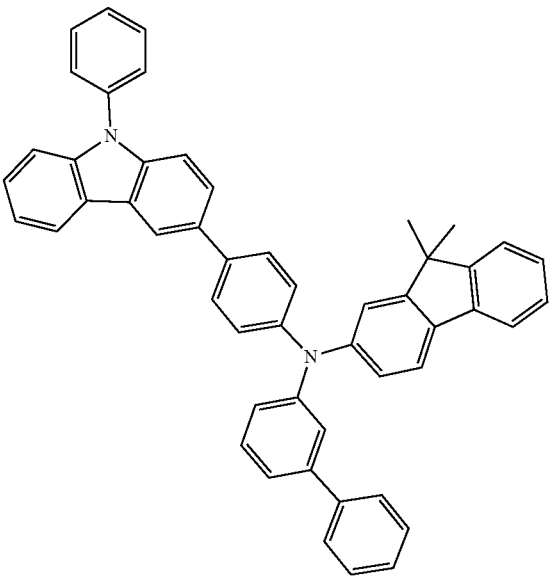

HT3

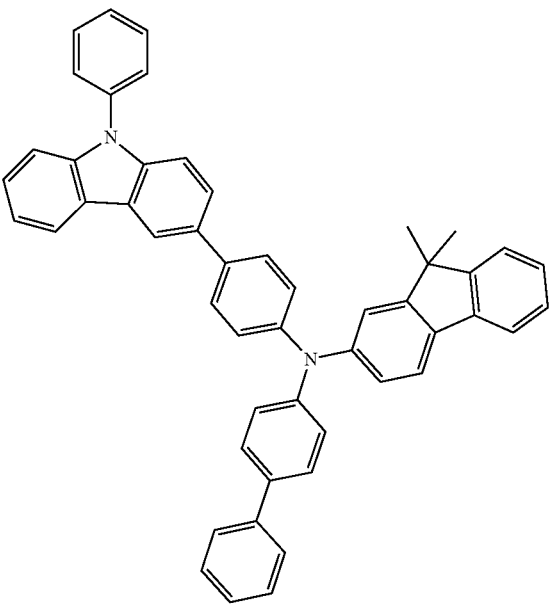

HT4
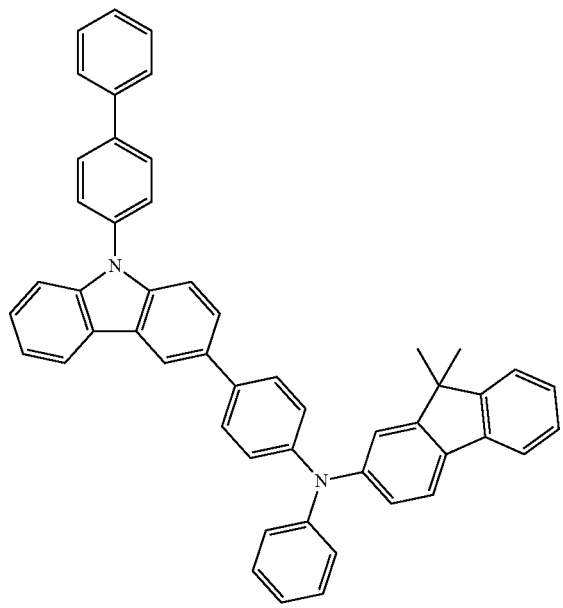
HT6
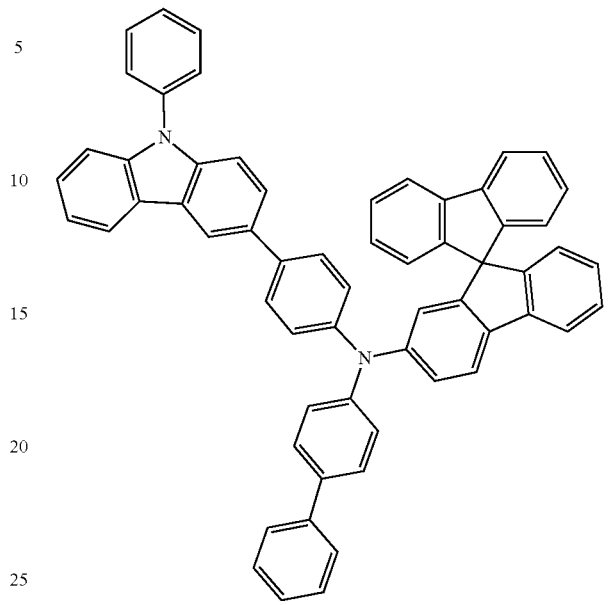
HT5
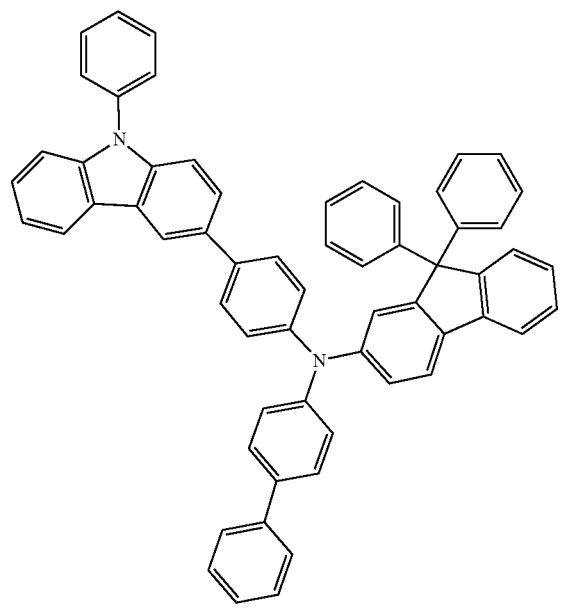
HT7
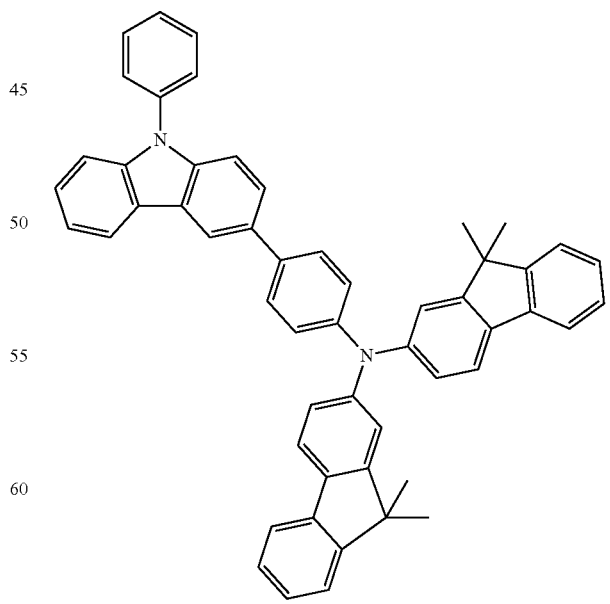

HT8
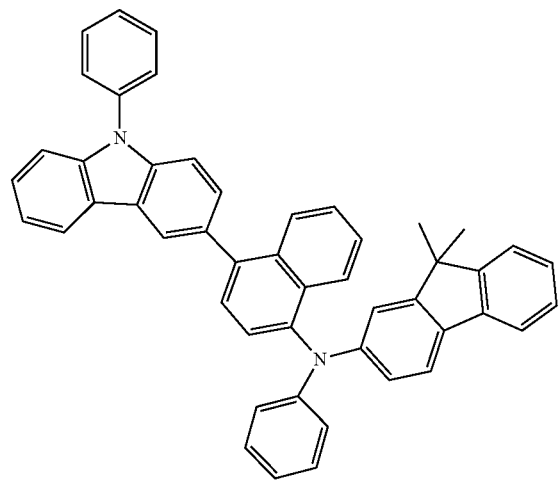
HT9
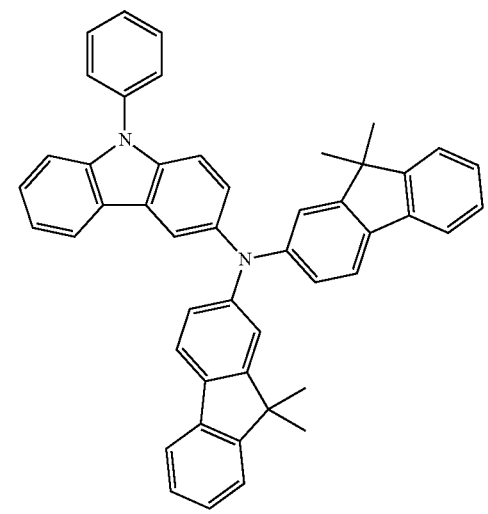
HT10
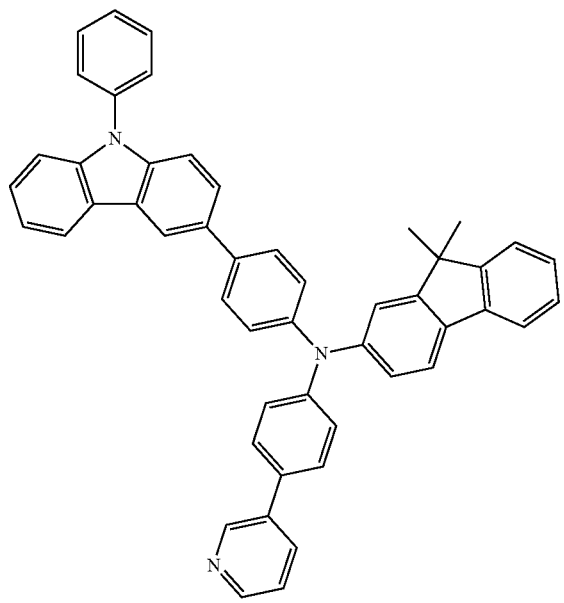
HT11
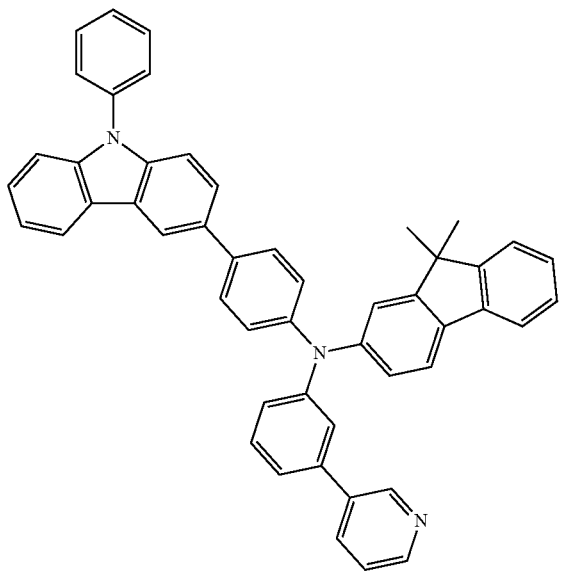
HT12
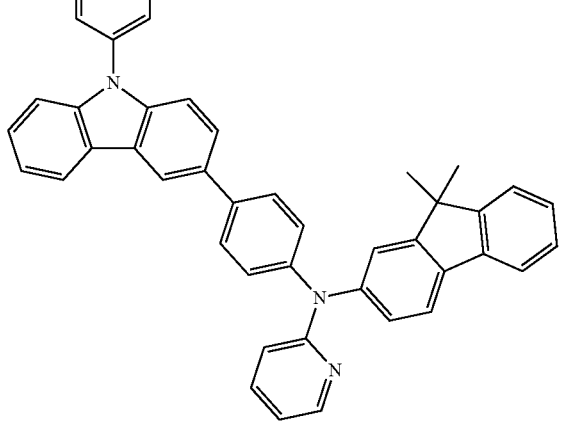
HT13
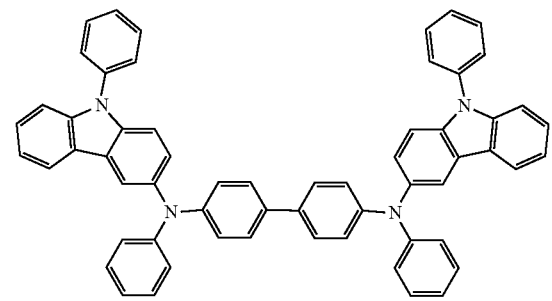

-continued

HT14
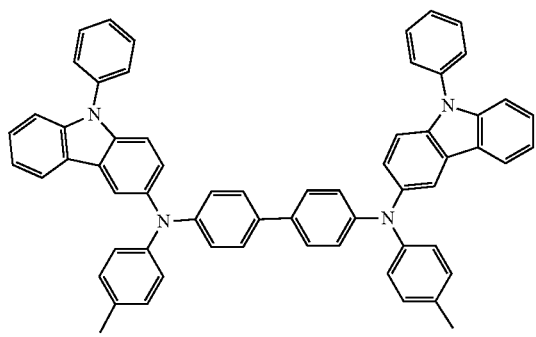

HT15
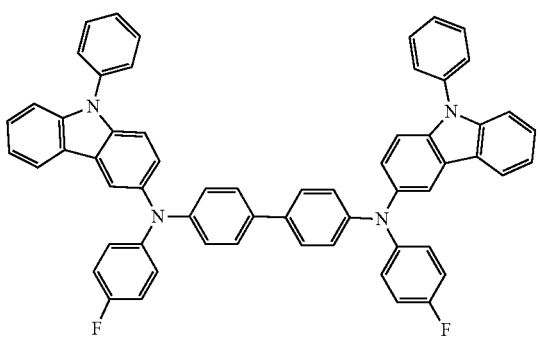

HT16
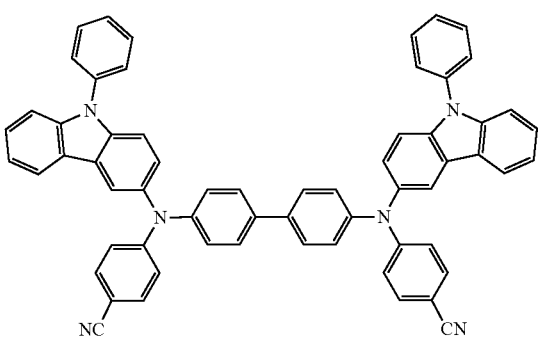

HT17
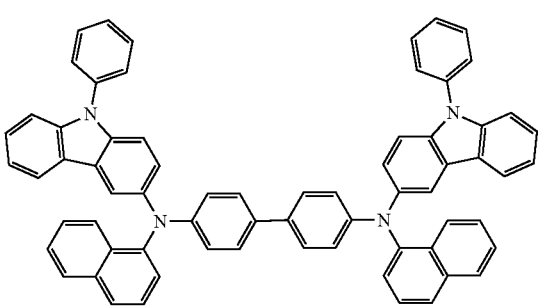

-continued

HT18
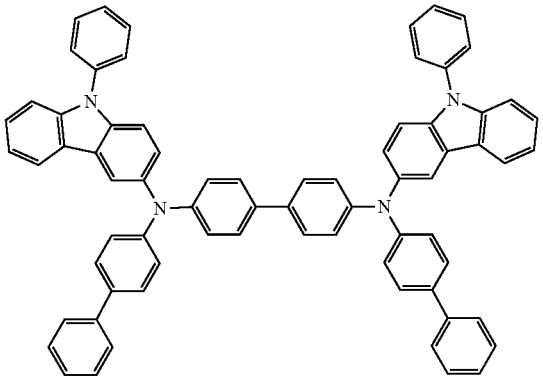

HT19
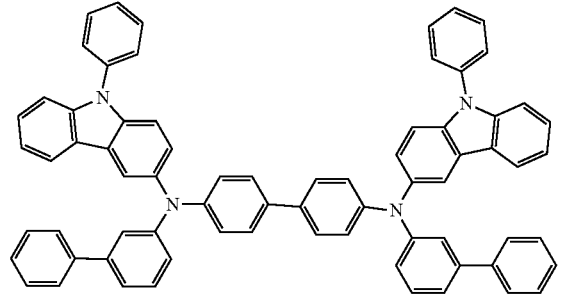

HT20
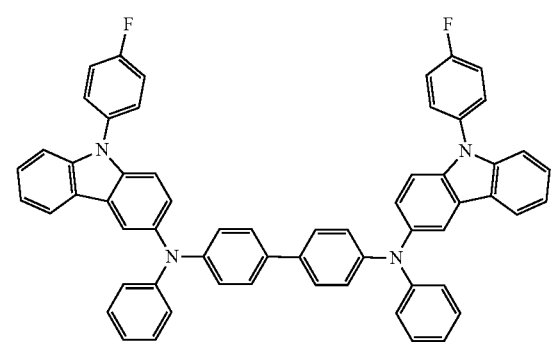

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may further include, in addition to the above-described materials, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but is not limited thereto. For example, non-limiting examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or Compound HP-1 illustrated below, but they are not limited thereto.

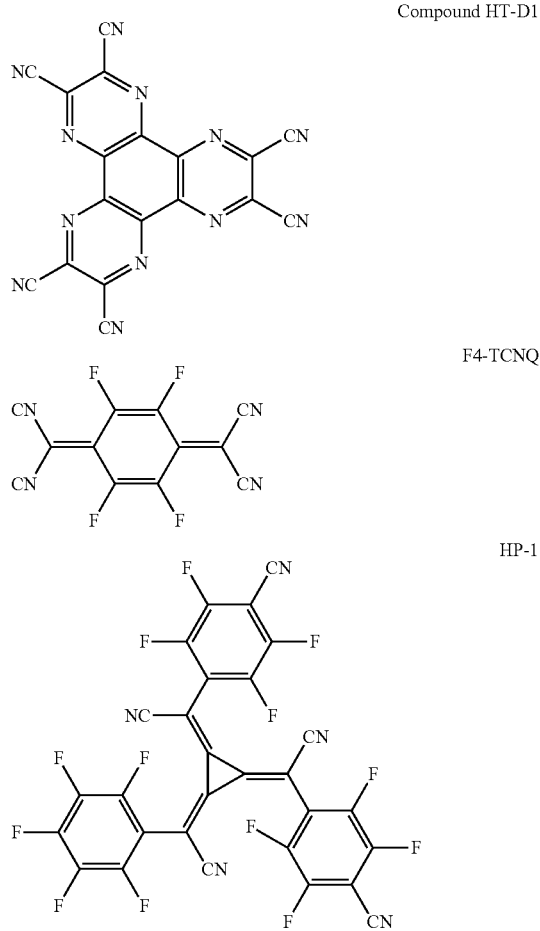

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using various methods, such as vacuum-deposition, spin coating, casting, or an LB method. When the emission layer is formed by vacuum-deposition or spin coating, vacuum-deposition and coating conditions for the emission layer may be generally similar to the conditions for forming a hole injection layer, though the conditions may vary depending on the compound used.

The hole transport region may further include an electron blocking layer. The electron blocking layer may include a well-known material such as mCP, but is not limited thereto.

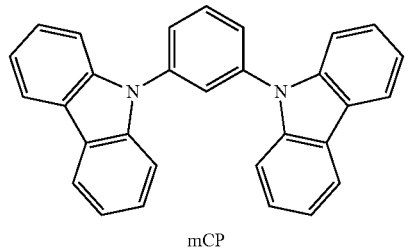 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the condensed cyclic compound represented by Formula 1. The emission layer may further include a dopant. The dopant may include at least one of a phosphorescent dopant and a fluorescent dopant.

Alternatively, the emission layer may include only the condensed cyclic compound represented by Formula 1, and the condensed cyclic compound may be a TADF emitter.

Alternatively, the emission layer may include only the condensed cyclic compound represented by Formula 1, and the condensed cyclic compound may be a TADF emitter, and the emission layer may further include a host.

For example, the host in the emission layer may include the condensed cyclic compound represented by Formula 1.

The dopant in the emission layer may include a fluorescent dopant which emits light according to a fluorescent emission mechanism or a phosphorescent dopant which emits light according to a phosphorescent emission mechanism.

According to an exemplary embodiment, the dopant in the emission layer may be a phosphorescent dopant, and the phosphorescent dopant may include an organometallic compound represented by Formula 81:

$$M(L_{81})_{n81}(L_{82})_{n82}$$ Formula 81

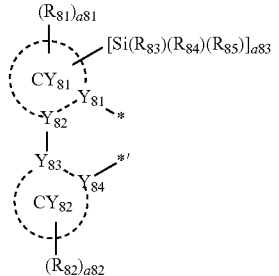

Formula 81A wherein in Formulae 81 and 81A,

M is selected from iridium (Ir), platinum (Pt), osmium (Os), titanium (Ti), zirconium (Zr), hafnium (Hf), europium (Eu), terbium (Tb), thulium (Tm), and rhodium (Rh), $L_{81}$ is a ligand represented by Formula 81A, n81 is an integer selected from 1 to 3, provided that when n81 is 2 or greater, two or more groups $L_{81}$ are identical to or different from each other, $L_{82}$ is an organic ligand, n82 is an integer selected from 0 to 4, provided that when n82 is 2 or greater, two or more groups $L_{82}$ are identical to or different from each other, $Y_{81}$ to $Y_{84}$ are each independently carbon (C) or nitrogen (N), $Y_{81}$ and $Y_{82}$ are connected to each other via a single bond or a double bond, and $Y_{83}$ and $Y_{84}$ are connected to each other via a single bond or a double bond, $CY_{81}$ and $CY_{82}$ are each independently selected from a $C_5$-$C_{30}$ carbocyclic group and a $C_3$-$C_{30}$ heterocarbocyclic group, $CY_{81}$ and $CY_{82}$ may be optionally further linked to each other via an organic linking group, $R_{81}$ to $R_{85}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{81}$)($Q_{82}$)($Q_{83}$), —N($Q_{84}$)($Q_{85}$), —B($Q_{86}$)($Q_{87}$), and —P(=O)($Q_{88}$)($Q_{89}$), a81 to a83 are each independently selected from integers of 0 to 5, provided that when a81 is 2 or greater, two or more groups $R_{81}$ are identical to or different from each other, when a82 is 2 or greater, two or more groups $R_{82}$ are identical to or different from each other, when a81 is 2 or greater, adjacent groups $R_{81}$ may be optionally linked to each other to form a saturated or unsaturated ring, when a82 is 2 or greater, adjacent groups $R_{82}$ may be optionally linked to each other to form a saturated or unsaturated ring,

* and *' in Formula 81A each indicate a binding site to M in Formula 81, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_1$)($Q_{92}$)($Q_{93}$), $Q_{81}$ to $Q_{89}$ and $Q_{91}$ to $Q_{93}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to an exemplary embodiment, in Formula 81A, a83 is 1 or 2, $R_{83}$ to $R_{85}$ may each independently be selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a $C_1$-$C_{10}$ alkyl group, and a phenyl group, but are not limited thereto.

In various embodiments, in Formula 81A, $Y_{81}$ may be nitrogen, $Y_{82}$ and $Y_{83}$ may each be carbon, $Y_{84}$ may be nitrogen or carbon, $CY_{81}$ and $CY_{82}$ may each independently be selected from a cyclopentadiene, a benzene, a heptalene, an indene, a naphthalene, an azulene, an indacene, an acenaphthylene, a fluorene, a spiro-bifluorene, a benzofluorene, a dibenzofluorene, a phenalene, a phenanthrene, an anthracene, a fluoranthene, a triphenylene, a pyrene, a chrysene, a naphthacene, a picene, a perylene, a pentacene, a hexacene, a pentaphene, a rubicene, a coronene, an ovalene, a pyrrole, an isoindole, an indole, an indazole, a pyrazole, an imidazole, a triazole, an oxazole, an isoxazole, an oxadiazole, a thiazole, an isothiazole, a thiadiazole, a purine, a furan, a thiophene, a pyridine, a pyrimidine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzoimidazole, a benzofuran, a benzothiophene, an isobenzothiazole, a benzoxazole, an isobenzoxazole, a benzocarbazole, a dibenzocarbazole, an imidazopyridine, an imidazopyrimidine, a dibenzofuran, a dibenzothiophene, a dibenzothiophene sulfone, a carbazole, a dibenzosilole, and a 2,3-dihydro-1H-imidazole.

According to some embodiments, in Formula 81A, $Y_{81}$ may be nitrogen, $Y_{82}$ to $Y_{84}$ may each be carbon, $CY_8$, may be selected from a 5-membered ring including two nitrogen atoms as ring-forming atoms, and $CY_{82}$ may be selected from a benzene, a naphthalene, a fluorene, a dibenzofuran, and a dibenzothiophene, but they are not limited thereto.

According to some embodiments, in Formula 81A, $Y_{81}$ may be nitrogen, $Y_{82}$ to $Y_{84}$ may each be carbon, $CY_{81}$ may be an imidazole or a 2,3-dihydro-1H-imidazole, and $CY_{82}$ may be selected from a benzene, a naphthalene, a fluorene, a dibenzofuran, and a dibenzothiophene, but they are not limited thereto.

According to some embodiments, in Formula 81A, $Y_{81}$ may be nitrogen, and $Y_{82}$ to $Y_{84}$ may each be carbon,
$CY_{81}$ may be selected from a pyrrole, a pyrazole, an imidazole, a triazole, an oxazole, an isoxazole, an oxadiazole, a thiazole, an isothiazole, a thiadiazole, a pyridine, a pyrimidine, a quinoline, an isoquinoline, a benzoquinoline, a phthalazine, a naphthyridine, a quinoxaline, a quinazoline, a cinnoline, a benzoimidazole, an iso-benzothiazole, a benzoxazole, and an isobenzoxazole, $CY_{82}$ may be selected from a cyclopentediene, a benzene, a naphthalene, a fluorene, a benzofluorene, a dibenzofluorene, a phenanthrene, an anthracene, a triphenylene, a pyrene, a chrysene, a perylene, a benzofuran, a benzothiophene, a benzocarbazole, a dibenzocarbazole, a dibenzofuran, a dibenzothiophene, a dibenzothiophene sulfone, a carbazole, and a dibenzosilole.

According to some embodiments, in Formula 81A, $R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B($Q_{86}$)($Q_{87}$) and —P(=O)($Q_{88}$)($Q_{89}$), wherein
$Q_{86}$ to $Q_{89}$ may each independently be selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group and a naphthyl group, each substituted with at least one selected from deuterium, a $C_1$-$C_{10}$ alkyl group, and a phenyl group.

According to some embodiments, in Formula 81A, $R_{81}$ and $R_{82}$ may each independently be selected from hydrogen, deuterium, —F, a cyano group, a nitro group, —$SF_5$, a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an iso-propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group; and —B($Q_{86}$)($Q_{87}$) and —P(=O)($Q_{88}$)($Q_{89}$),
$Q_{86}$ to $Q_{89}$ may each independently be selected from
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;

an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group and a naphthyl group, each substituted with at least one selected from deuterium, a $C_1$-$C_{10}$ alkyl group, and a phenyl group.

According to some embodiments, in Formula 81A, $R_{81}$ and $R_{82}$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, and groups represented by Formulae 10-1 to 10-30, but are not limited thereto:

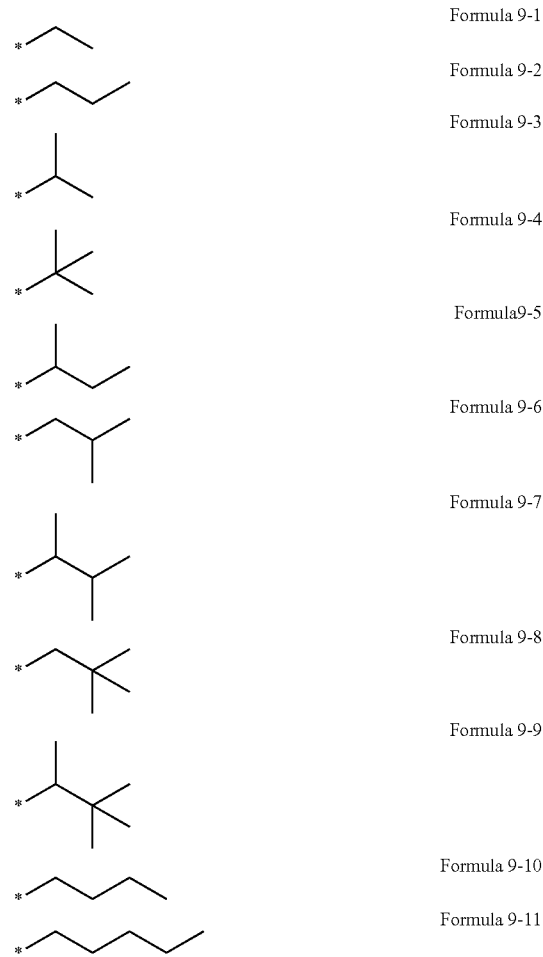

Formula 9-1
Formula 9-2
Formula 9-3
Formula 9-4
Formula 9-5
Formula 9-6
Formula 9-7
Formula 9-8
Formula 9-9
Formula 9-10
Formula 9-11

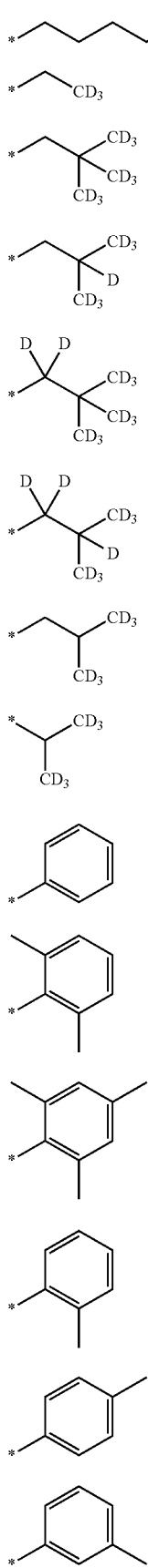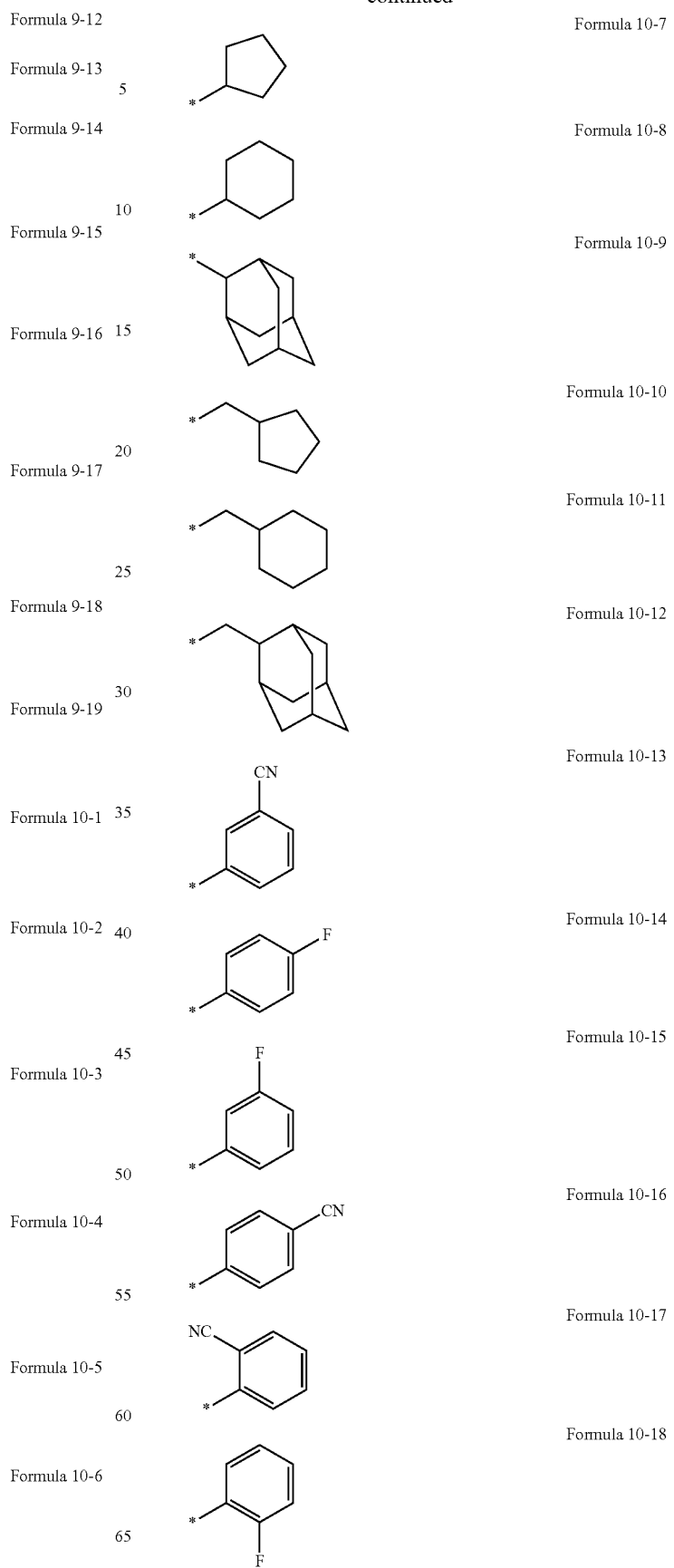

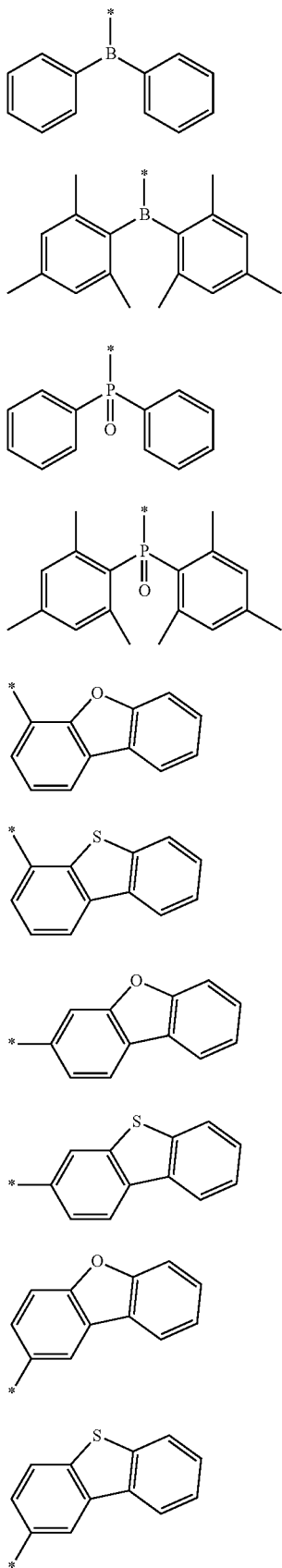

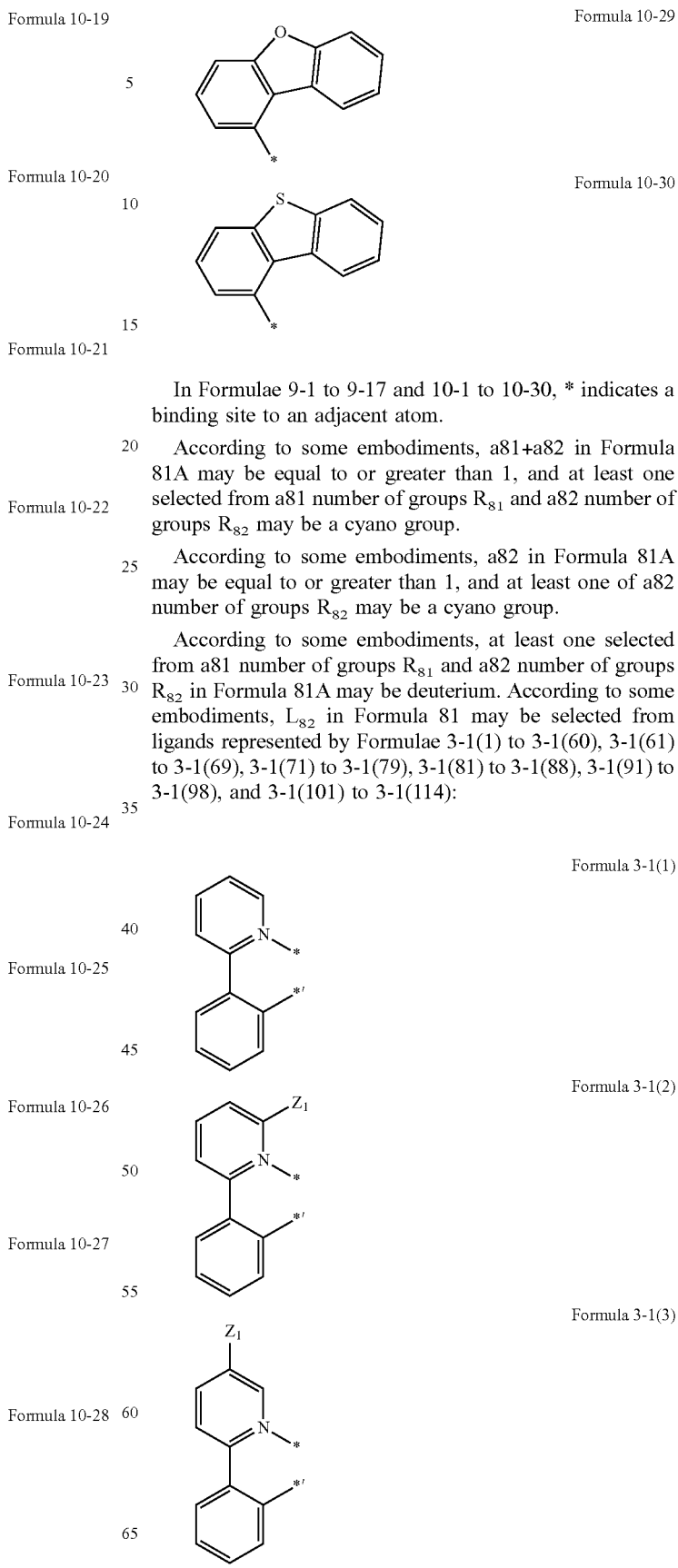

In Formulae 9-1 to 9-17 and 10-1 to 10-30, * indicates a binding site to an adjacent atom.

According to some embodiments, a81+a82 in Formula 81A may be equal to or greater than 1, and at least one selected from a81 number of groups $R_{81}$ and a82 number of groups $R_{82}$ may be a cyano group.

According to some embodiments, a82 in Formula 81A may be equal to or greater than 1, and at least one of a82 number of groups $R_{82}$ may be a cyano group.

According to some embodiments, at least one selected from a81 number of groups $R_{81}$ and a82 number of groups $R_{82}$ in Formula 81A may be deuterium. According to some embodiments, $L_{82}$ in Formula 81 may be selected from ligands represented by Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114):

-continued
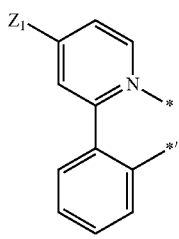
Formula 3-1(4)
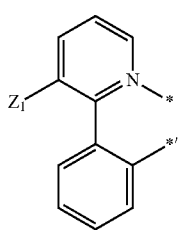
Formula 3-1(5)
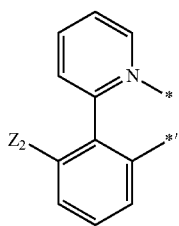
Formula 3-1(6)
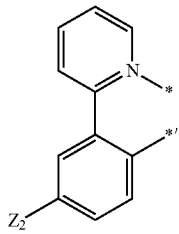
Formula 3-1(7)
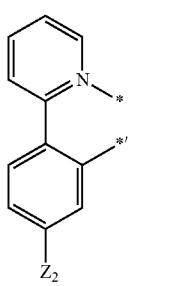
Formula 3-1(8)
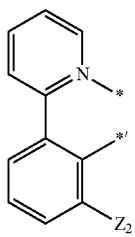
Formula 3-1(9)
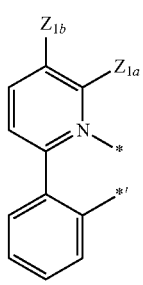
Formula 3-1(10)
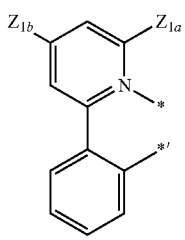
Formula 3-(11)
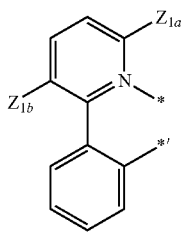
Formula 3-1(12)
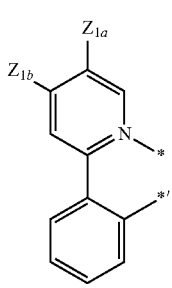
Formula 3-1(13)
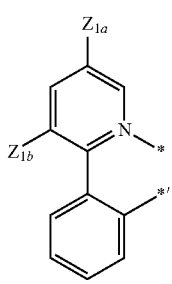
Formula 3-1(14)
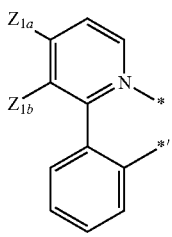
Formula 3-1(15)

Formula 3-1(16)

Formula 3-1(17)

Formula 3-1(18)

Formula 3-1(19)

Formula 3-1(20)

Formula 3-1(21)

Formula 3-1(22)

Formula 3-1(23)

Formula 3-1(24)

Formula 3-1(25)

Formula 3-1(26)

Formula 3-1(27)

-continued
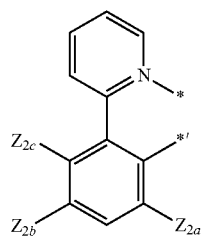
Formula 3-1(28)
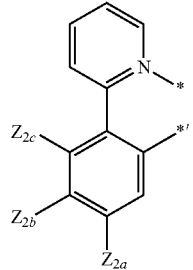
Formula 3-1(29)
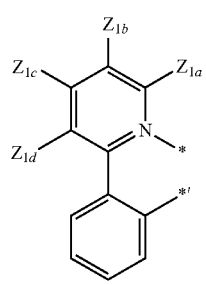
Formula 3-1(30)
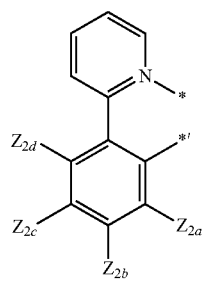
Formula 3-1(31)
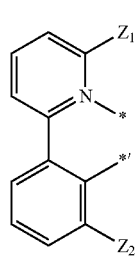
Formula 3-1(32)
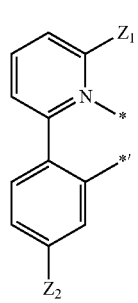
Formula 3-1(33)
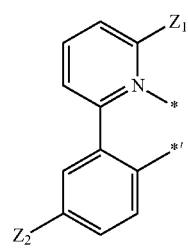
Formula 3-1(34)
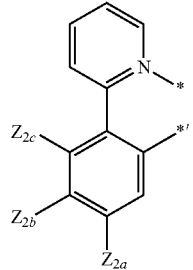
Formula 3-1(35)
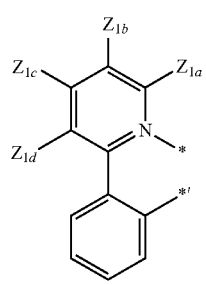
Formula 3-1(36)
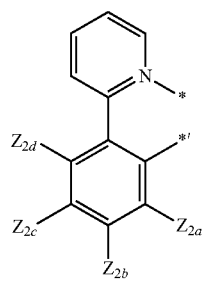
Formula 3-1(37)
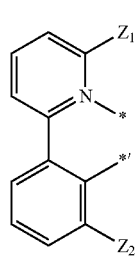
Formula 3-1(38)

Formula 3-1(39)
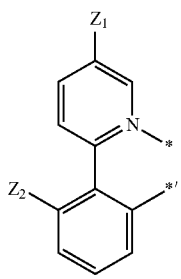
Formula 3-1(40)
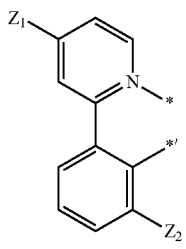
Formula 3-1(41)
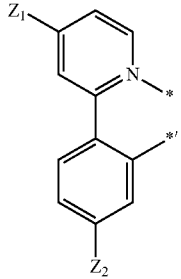
Formula 3-1(42)
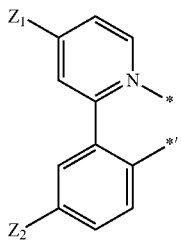
Formula 3-1(43)
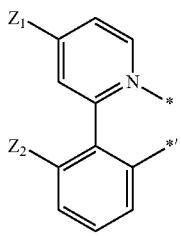
Formula 3-1(44)
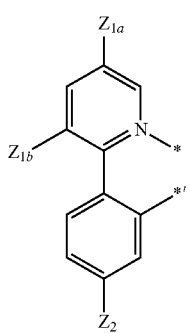
Formula 3-1(45)
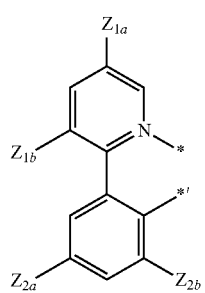
Formula 3-1(46)
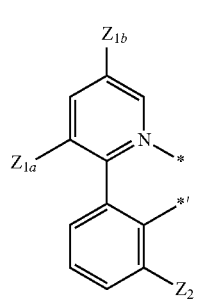
Formula 3-1(47)
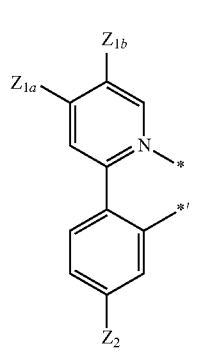
Formula 3-1(48)
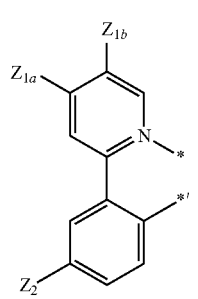
Formula 3-1(49)
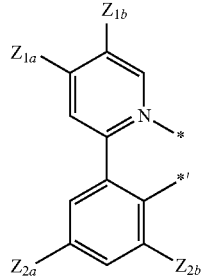

-continued
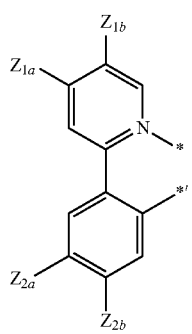
Formula 3-1(50)
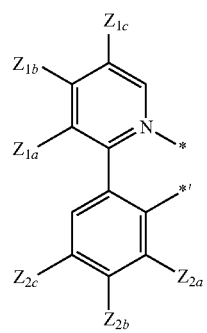
Formula 3-1(55)
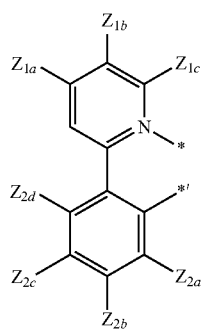
Formula 3-1(51)
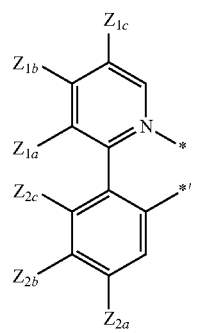
Formula 3-1(56)
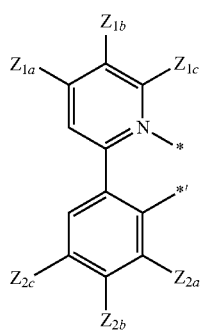
Formula 3-1(52)
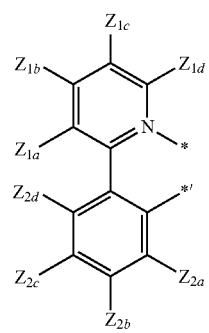
Formula 3-1(57)
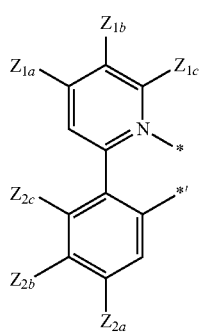
Formula 3-1(53)
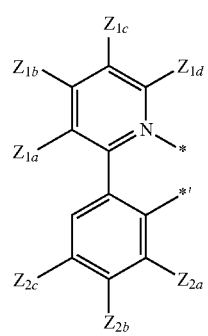
Formula 3-1(58)
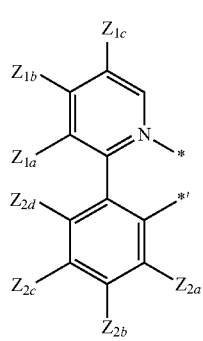
Formula 3-1(54)
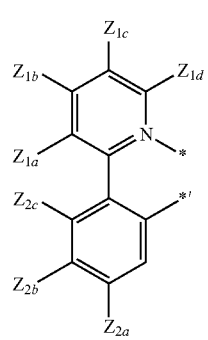
Formula 3-1(59)

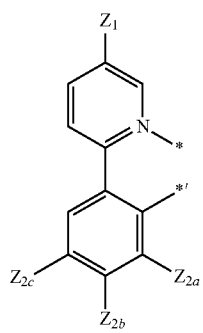
Formula 3-1(60)
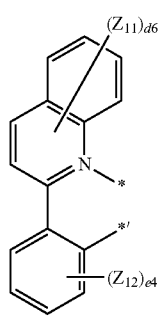
Formula 3-1(61)
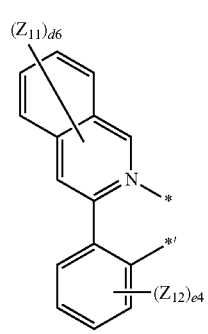
Formula 3-1(62)
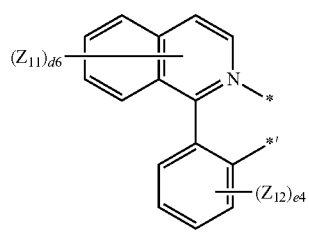
Formula 3-1(63)
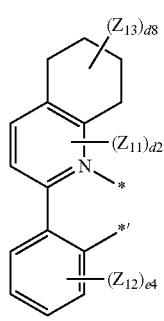
Formula 3-1(64)
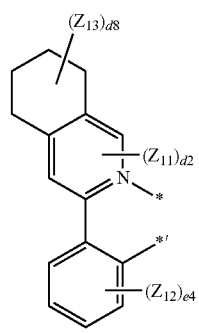
Formula 3-1(65)
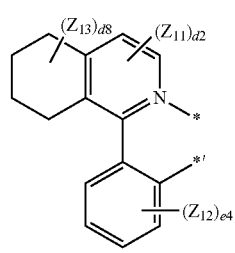
Formula 3-1(66)
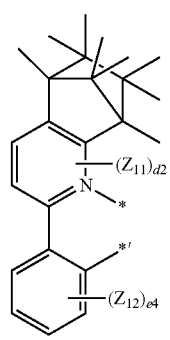
Formula 3-1(67)
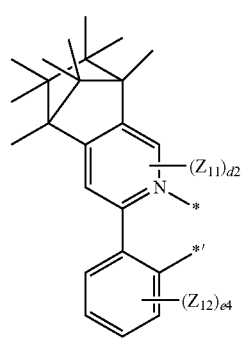
Formula 3-1(68)
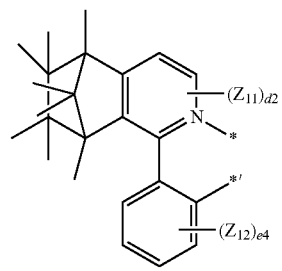
Formula 3-1(69)

Formula 3-1(71)
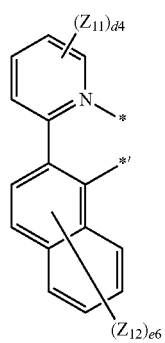
Formula 3-1(72)
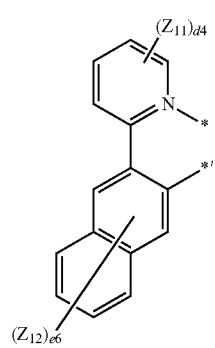
Formula 3-1(73)
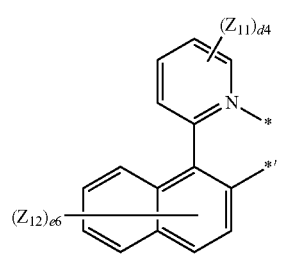
Formula 3-1(74)
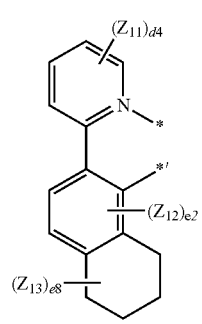
Formula 3-1(75)
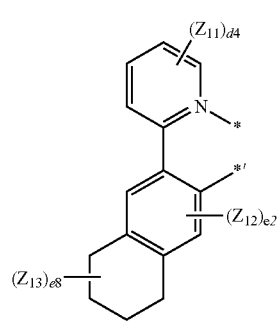
Formula 3-1(76)
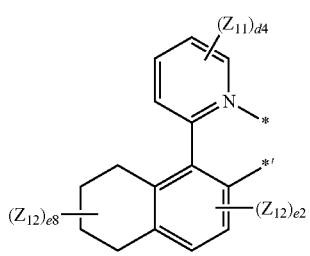
Formula 3-1(77)
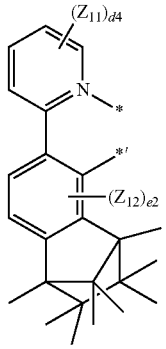
Formula 3-1(78)
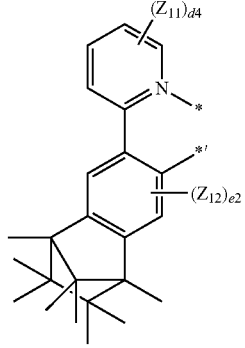
Formula 3-1(79)
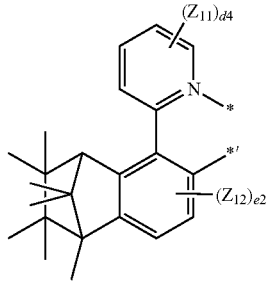
Formula 3-1(81)
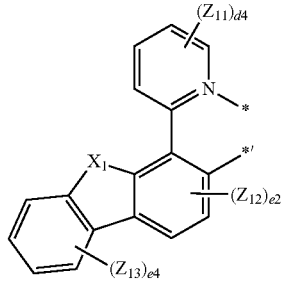

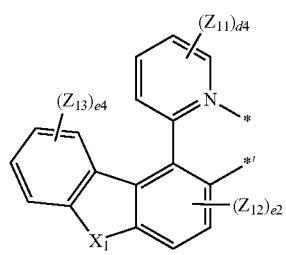
Formula 3-1(82)
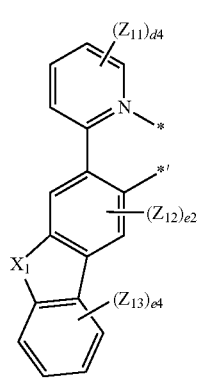
Formula 3-1(83)
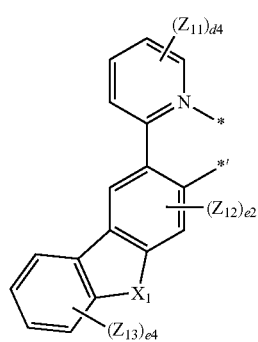
Formula 3-1(84)
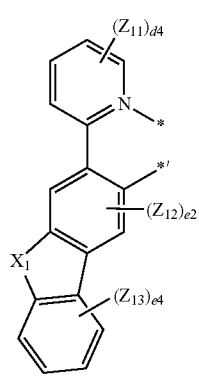
Formula 3-1(85)
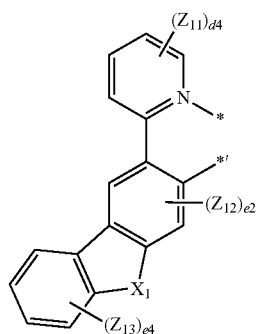
Formula 3-1(86)
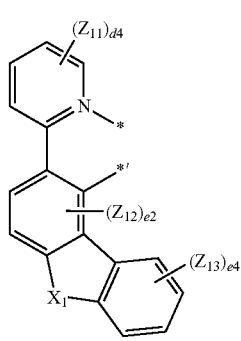
Formula 3-1(87)
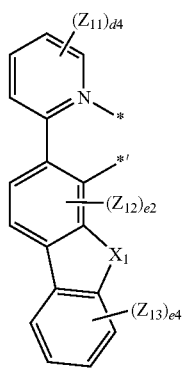
Formula 3-1(88)
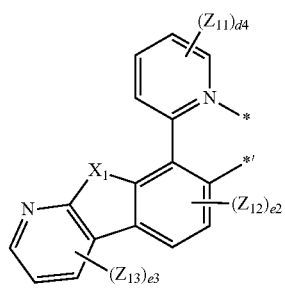
Formula 3-1(91)
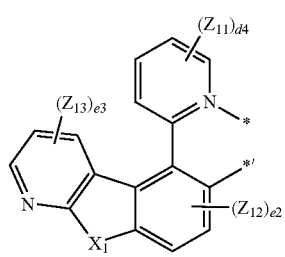
Formula 3-1(92)

-continued
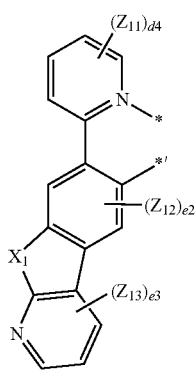
Formula 3-1(93)
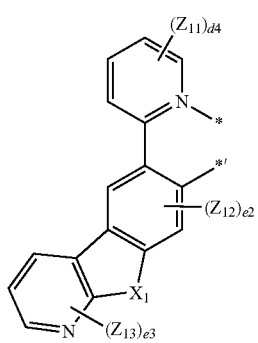
Formula 3-1(94)
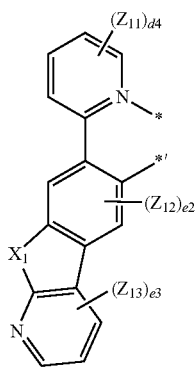
Formula 3-1(95)
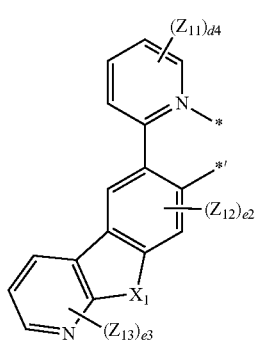
Formula 3-1(96)
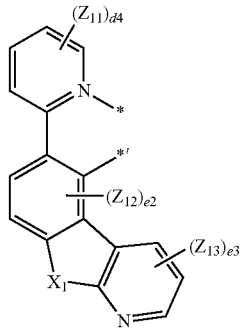
Formula 3-1(97)
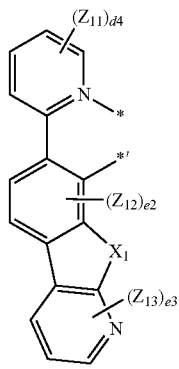
Formula 3-1(98)
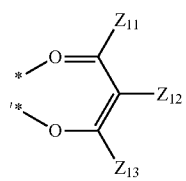
Formula 3-1(101)
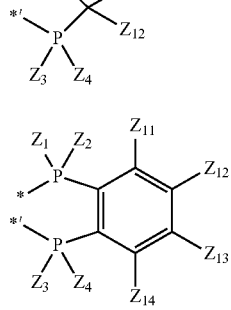
Formula 3-1(102)
Formula 3-1(103)
Formula 3-1(104)
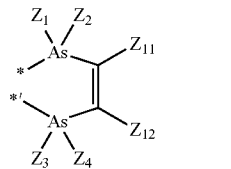
Formula 3-1(105)

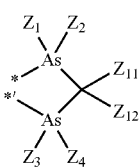
Formula 3-1(106)

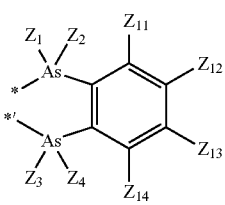
Formula 3-1(107)

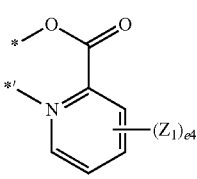
Formula 3-1(108)

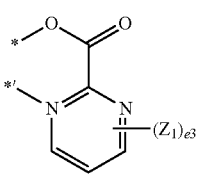
Formula 3-1(109)

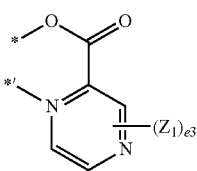
Formula 3-1(110)

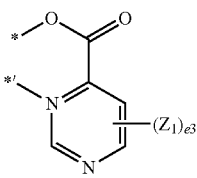
Formula 3-1(111)

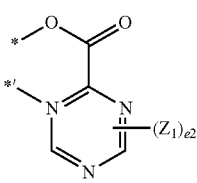
Formula 3-1(112)

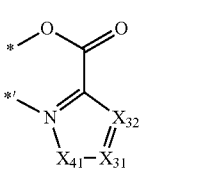
Formula 3-1(113)

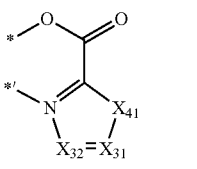
Formula 3-1(114)

In Formulae 3-1(1) to 3-1(60), 3-1(61) to 3-1(69), 3-1(71) to 3-1(79), 3-1(81) to 3-1(88), 3-1(91) to 3-1(98), and 3-1(101) to 3-1(114), $X_1$ is O, S, $C(Z_{21})(Z_{22})$, or $N(Z_{23})$, $X_{31}$ is N or $C(Z_{1a})$, $X_{32}$ is N or $C(Z_{1b})$, $X_{41}$ is O, S, $N(Z_{1a})$, or $C(Z_{1a})(Z_{1b})$, $Z_1$ to $Z_4$, $Z_{1a}$, $Z_{1b}$, $Z_{1c}$, $Z_{1d}$, $Z_{2a}$, $Z_{2b}$, $Z_{2c}$, $Z_{2d}$, $Z_{11}$ to $Z_{14}$, and $Z_{21}$ to $Z_{23}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, C$_1$-C$_{20}$ alkyl group, C$_1$-C$_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_{86}$)(Q$_{87}$) and —P(=O)(Q$_{88}$)(Q$_{89}$), wherein
Q$_{86}$ to Q$_{89}$ may each independently be selected from —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;
an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group; and
an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, and a naphthyl group, each substituted with at least one selected from deuterium, a C$_1$-C$_{10}$ alkyl group, and a phenyl group, d2 and e2 may each independently be 0 or 2,
e3 may be an integer selected from 0 to 3, d4 and e4 may each independently be an integer selected from 0 to 4, d6 and e6 may each independently be an integer selected from 0 to 6, d8 and e8 may each independently be an integer selected from 0 to 8,

* and *' each indicate a binding site to M in Formula 1.

For example, Z$_1$ to Z$_4$, Z$_{1a}$, Z$_{1b}$, Z$_{1c}$, Z$_{1d}$, Z$_{2a}$, Z$_{2b}$, Z$_{2c}$, Z$_{2d}$, Z$_{11}$ to Z$_{14}$, and Z$_{21}$ to Z$_{23}$ may each independently be selected from hydrogen, deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulae 9-1 to 9-19, and groups represented by Formulae 10-1 to 10-30, but are not limited thereto.

According to some embodiments, M in Formula 81 may be Ir, n81+n82 may be 3; or M may be Pt, and n81+n82 may be 2.

According to some embodiments, an organometallic compound represented by Formula 81 may not be a salt consisting of a pair of a cation and an anion, but may be neutral.

The phosphorescent dopant may include at least one selected from Compounds PD1 to PD78 and FIr$_6$ below, but it is not limited thereto:

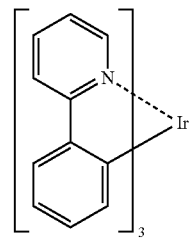

PD1

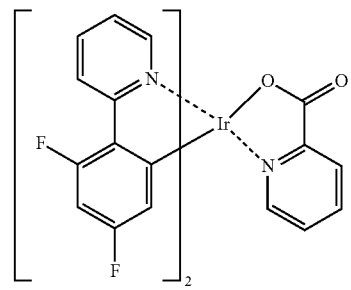

PD2

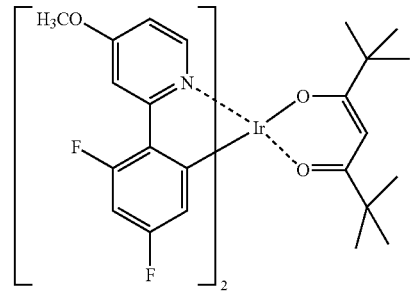

PD3

PD4 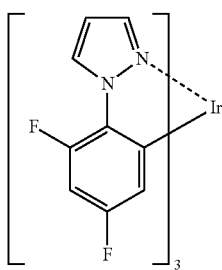
PD5 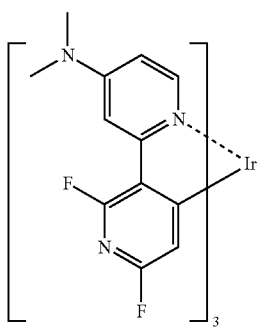
PD6 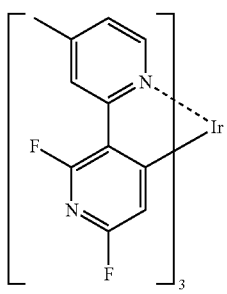
PD7 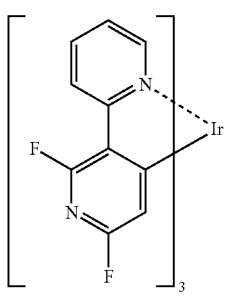
PD8 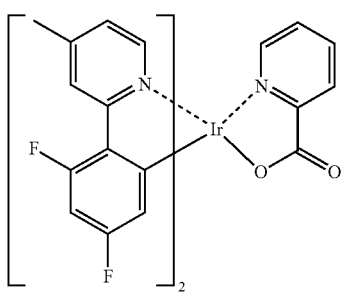
PD9 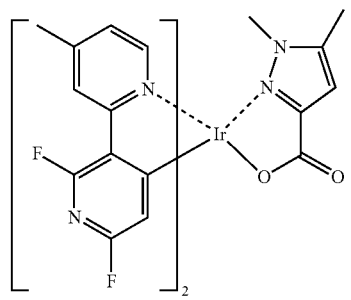
PD10 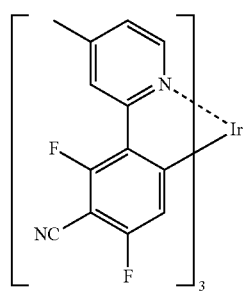
PD11 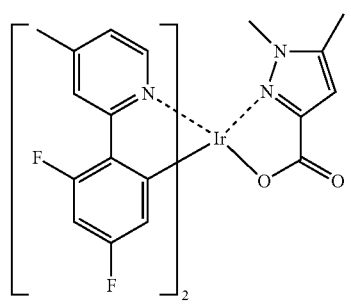
PD12 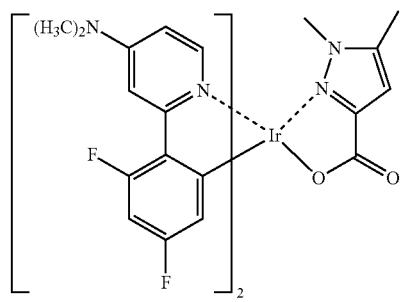
PD13 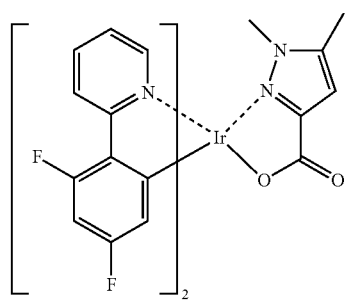

PD14 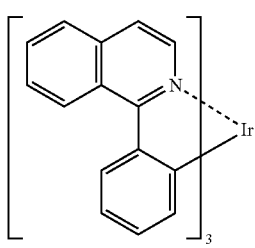
PD15 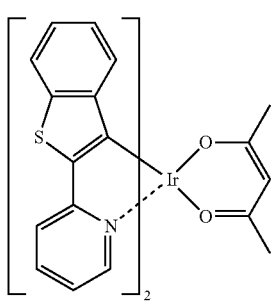
PD16
PD17
PD18
PD19 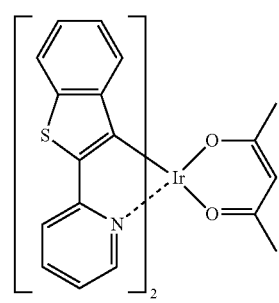
PD20 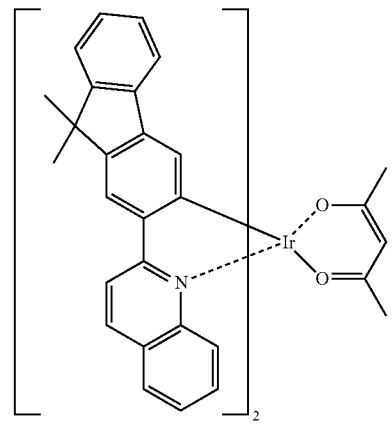
PD21 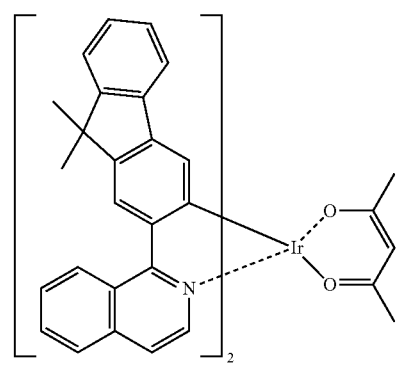
PD22 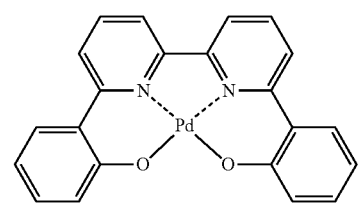
PD23 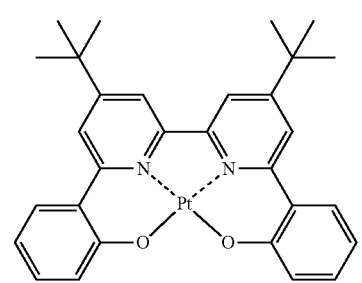

-continued
PD24
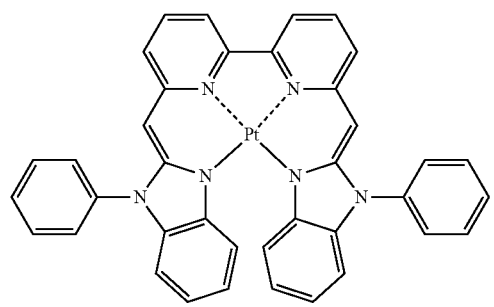
PD25
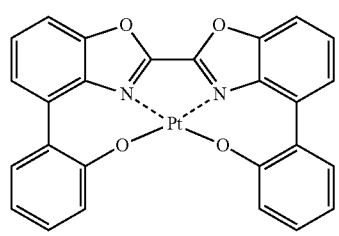
PD26
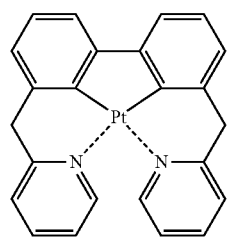
PD27
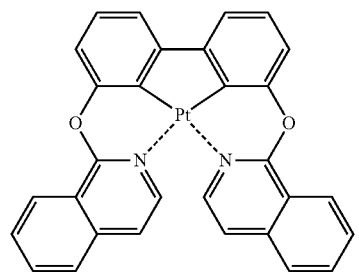
PD28
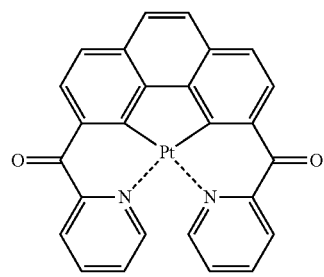
PD29
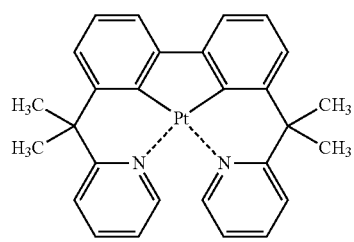
-continued
PD30
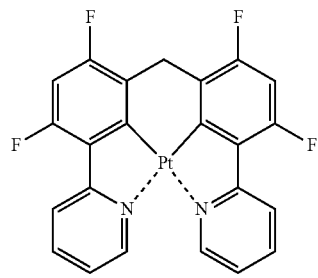
PD31
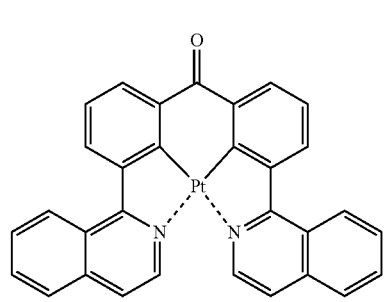
PD32
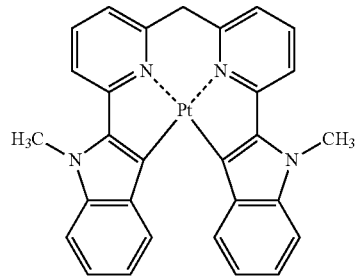
PD33
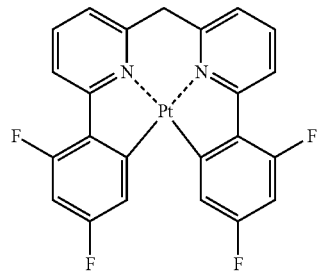
PD34
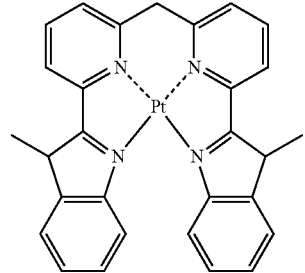

-continued
PD35
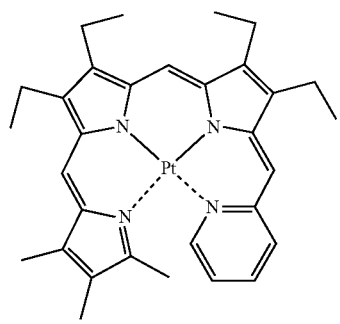
PD36
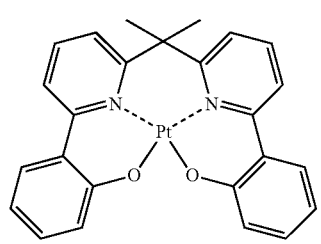
PD37
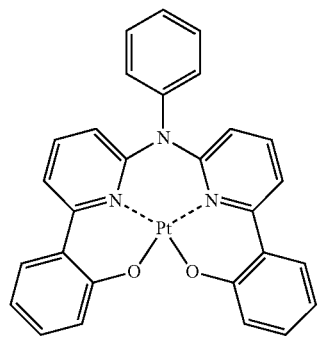
PD38
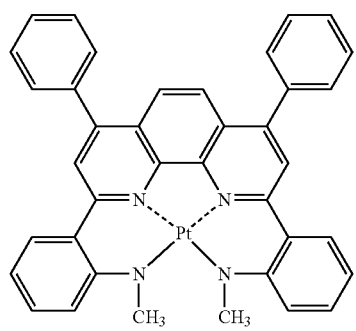
PD39
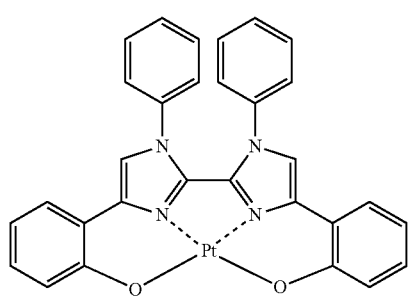
-continued
PD40
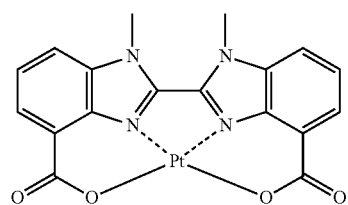
PD41
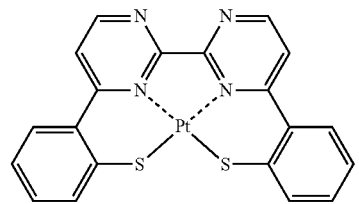
PD42
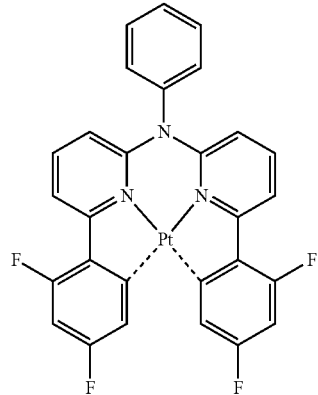
PD43
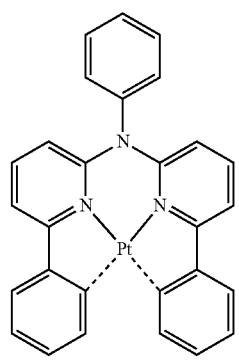
PD44
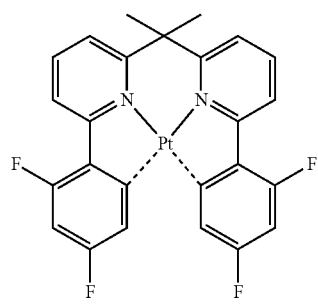

PD45
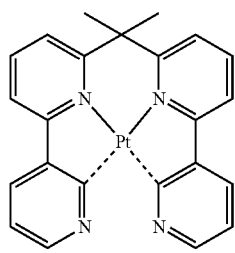
PD46
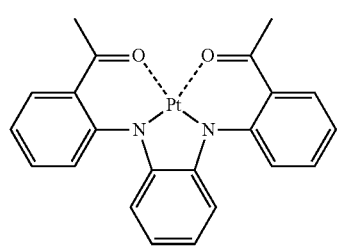
PD47
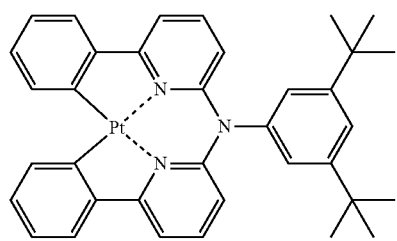
PD48
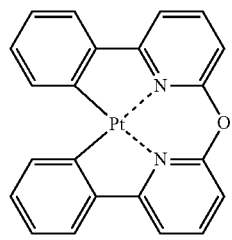
PD49
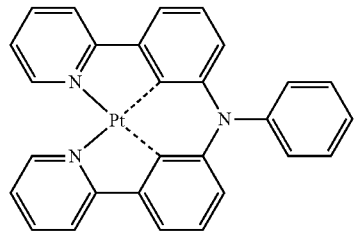
PD50
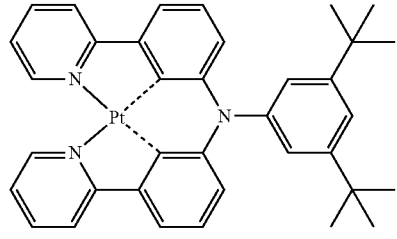
PD51
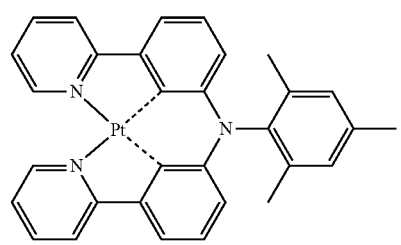
PD52
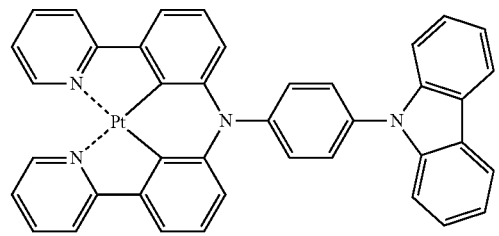
PD53
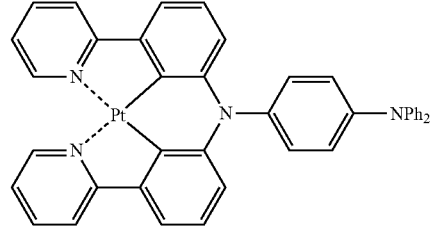
PD54
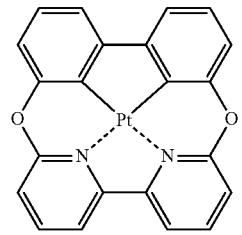
PD55
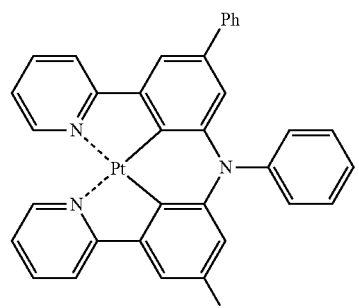
PD56
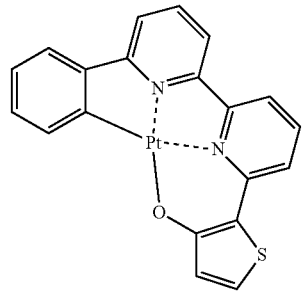

PD57 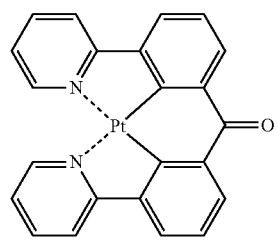
PD58 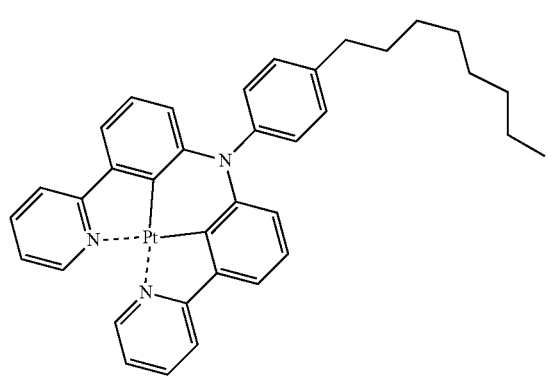
PD59 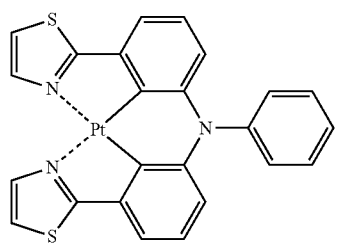
PD60 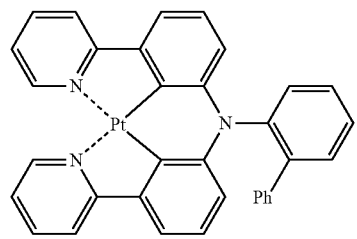
PD61 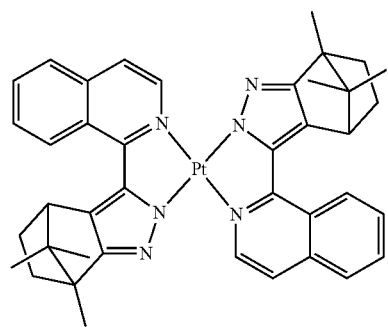
PD62 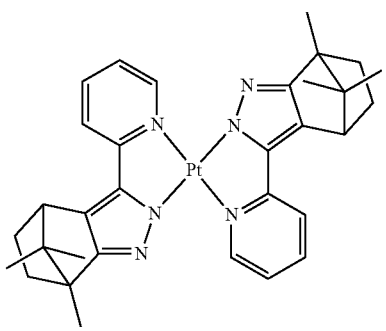
PD63 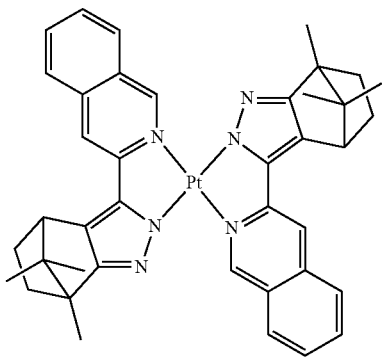
PD64 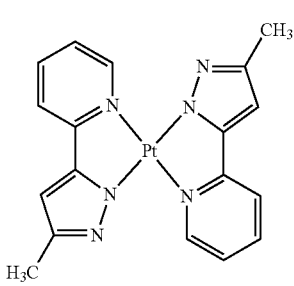
PD65 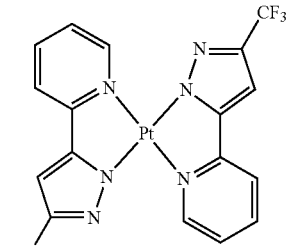
PD66 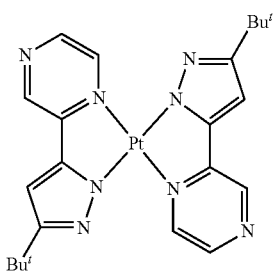

-continued
PD67
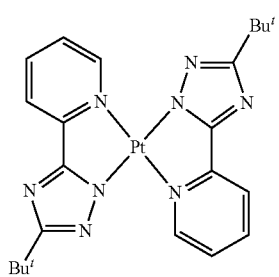
PD68
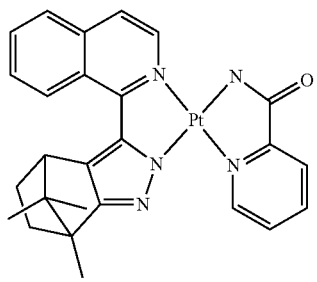
PD69
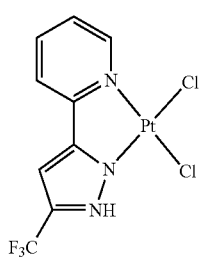
PD70
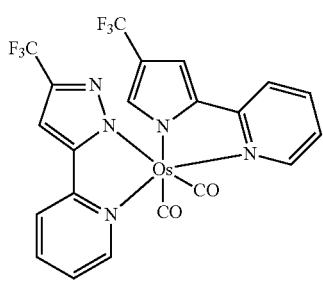
PD71
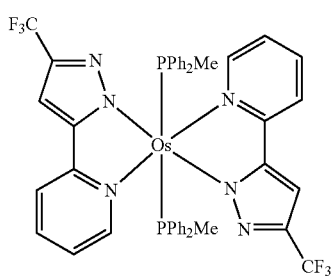
PD72
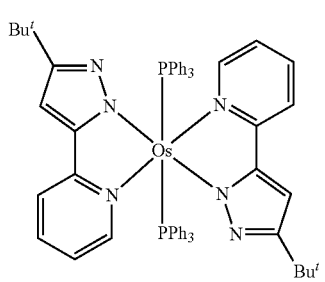
-continued
PD73
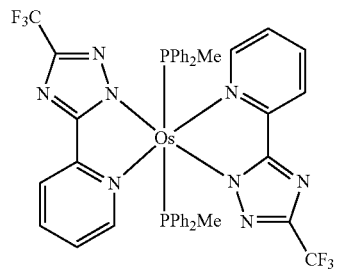
PD74
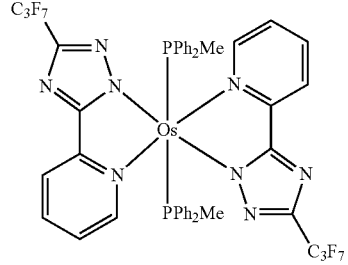
PD75
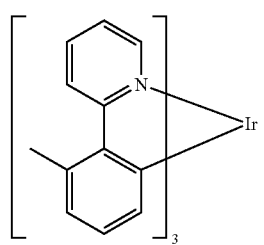
PD76
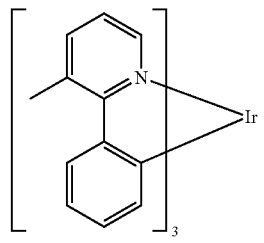
PD77
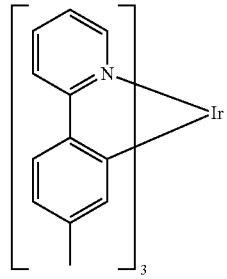
PD78
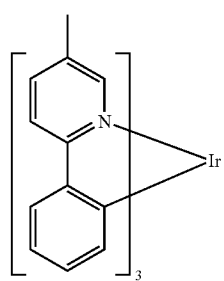

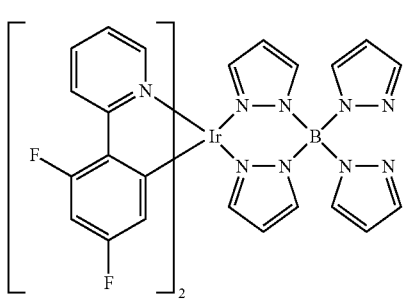

Flr6

Alternatively, the phosphorescent dopant may include PtOEP below:

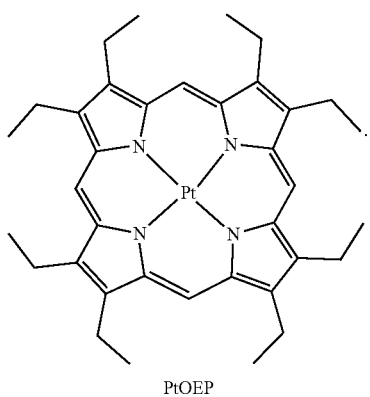

PtOEP

When the emission layer includes the host and the dopant, an amount of the dopant may be selected from in a range of about 0.01 to about 20 parts by weight based on about 100 parts by weight of the host, but the amount is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may include, for example, at least one of BCP and Bphen, but it is not limited thereto.

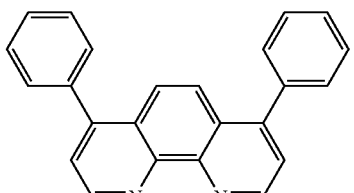

BCP

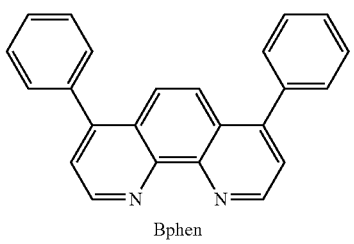

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within this range, excellent hole blocking characteristics may be obtained without a substantial increase in driving voltage.

The electron transport layer may further include at least one selected from BCP, Bphen, Alq$_3$, BAlq, TAZ, and NTAZ.

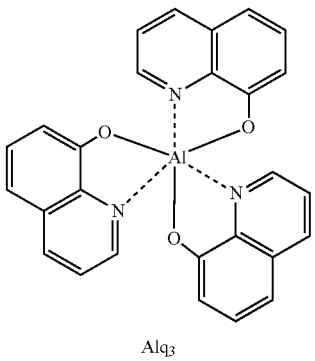

Alq$_3$

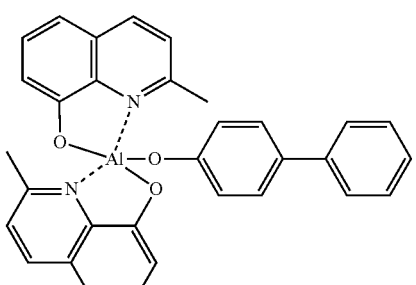

BAlq

-continued

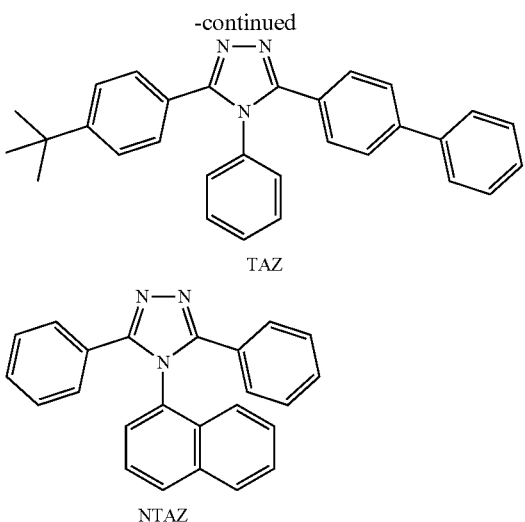

TAZ

NTAZ

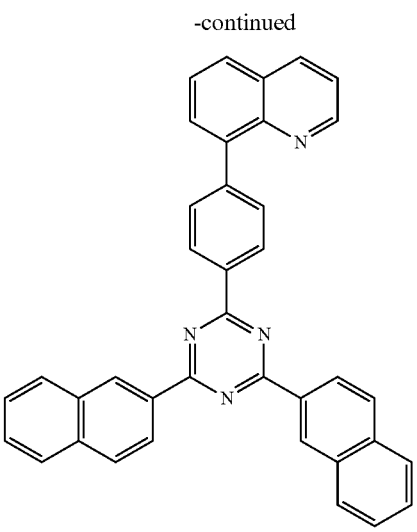

ET3

Alternatively, the electron transport layer may include at least one selected from Compounds ET1, ET2, and ET3, but it is not limited thereto.

A thickness of the electron transport layer may be in a range of about 100 Å to about 1,000 Å, for example, about 150 Å to about 500 Å. While not wishing to be bound by theory, it is understood that when the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET1

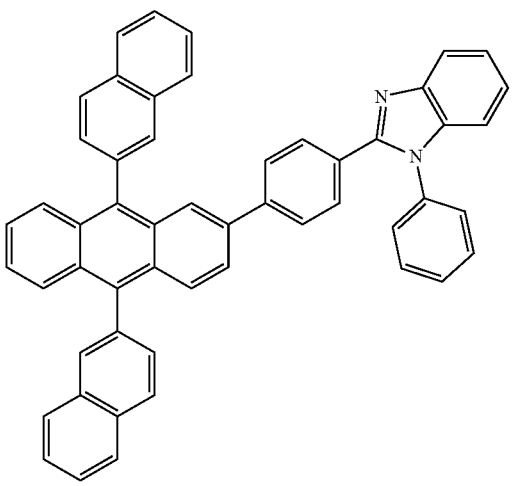

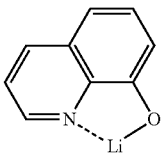

ET-D1

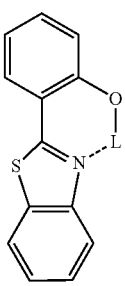

ET-D2

ET2

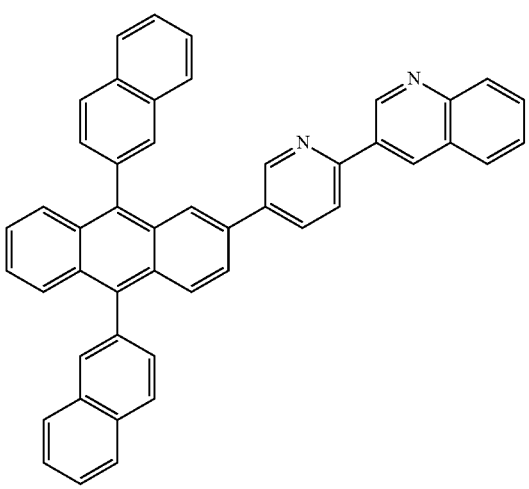

The electron transport region may include an electron injection layer (EIL) that facilitates electron injection from the second electrode 19.

The electron injection layer may include at least one selected from, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to the FIGURE, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_6$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an iso-propyloxy group.

A $C_2$-$C_{60}$ alkenyl group as used herein refers to a group formed by including at least one carbon double bond in the middle or at the terminal of the $C_2$-$C_{60}$ alkyl group Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by including at least one carbon triple bond in the middle or at the terminal of the $C_2$-$C_{60}$ alkyl group. Detailed examples thereof are an ethynyl group and a propynyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P, Si, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group including 3 to 10 carbon atoms and at least one double bond in the ring thereof, which does not have aromaticity. Detailed examples thereof are a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, Si, and S as a ring-forming atom, 1 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other or may be connected to each other by a single bond.

A $C_1$-$C_6$ heteroaryl group as used herein refers to a monovalent group having a carbocyclic aromatic system having at least one hetero atom selected from N, O, P, Si, and S as a ring-forming atom and 1 to 60 carbon atoms. A $C_1$-$C_{60}$ heteroarylene group as used herein refers to a divalent group having a carbocyclic aromatic system having at least one hetero atom selected from N, O, P, Si, and S as a ring-forming atom and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other or may be connected to each other by a single bond.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, and only carbon atoms (for example, the number of carbon atoms may be in a range of 8 to 60) as ring forming atoms, wherein the molecular structure as a whole is non-aromatic. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has two or more rings condensed with each other, and has a hetero atom selected from N, O P, Si, and S, other than carbon atoms (for example, the number of carbon atoms may be in a range of 1 to 60), as ring-forming atoms, wherein the molecular structure as a whole is non-aromatic. Detailed examples of the monovalent non-aromatic condensed heteropolycyclic group include a carbazolyl group. A divalent non-aromatic condensed hetero-polycyclic group used herein refers to a divalent group having the same structure as the monovalent non-aromatic condensed hetero-polycyclic group.

At least one substituent as used herein in the substituted $C_3$-$C_{10}$ cycloalkylene group, substituted $C_1$-$C_{10}$ heterocycloalkylene group, substituted $C_3$-$C_{10}$ cycloalkenylene group, substituted C₁-C₁₀ heterocycloalkenylene group, substituted C₆-C₆₀ arylene group, substituted C₁-C₆₀ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group or substituted monovalent non-aromatic condensed heteropolycyclic group is selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{31}$)($Q_{32}$)($Q_{33}$).

$Q_1$ to $Q_3$, $Q_{11}$ to $Q_{13}$, $Q_{21}$ to $Q_{23}$, and $Q_{31}$ to $Q_{33}$ are each independently selected from hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

A biphenyl group as used herein refers to a monovalent group including two benzenes linked to each other via a single bond.

A terphenyl group as used herein refers to a monovalent group including three benzenes linked to one another via a single bond.

Hereinafter, a compound and an organic light-emitting device according to an exemplary embodiment will be described in detail with reference to Synthesis Examples and Examples. However, the inventive concept is not limited to Synthesis Examples and Examples. The wording "B was used instead of A" used in describing Synthesis Examples means that an amount of B used was identical to an amount of A used based on molar equivalence.

EXAMPLE

Synthesis Example 1: Synthesis of Compound 15

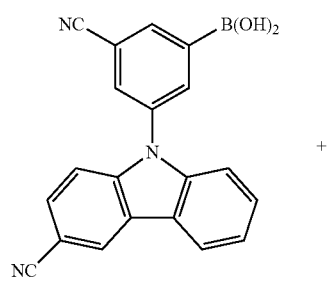

+

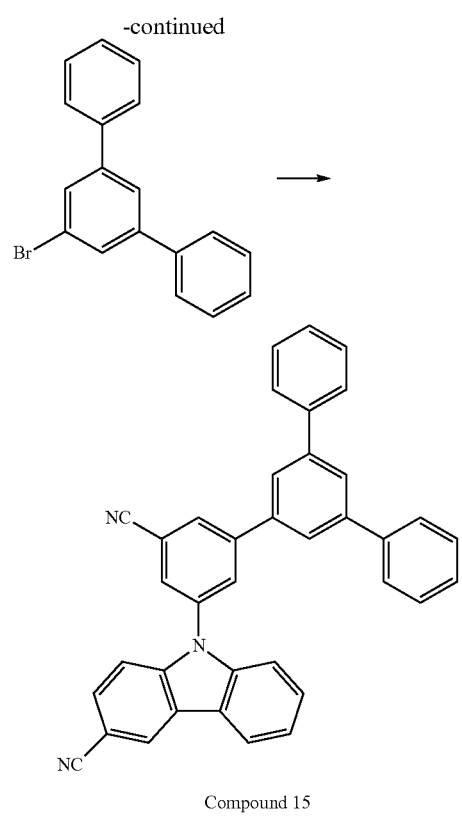

Compound 15

13.084 grams (g) (38.81 millimoles (mmol)) of [3-cyano-5-(3-cyano-9H-fluorene-9-yl)phenyl]boronic acid, 10 g (32.34 mmol) of 1-bromo-3,5-diphenylbenzene, 3.737 g (3.23 mmol) of tetrakis(triphenylphosphine)palladium [Pd(PPh₃)₄], and 8.940 g (64.68 mmol) of potassium carbonate were added to 40 milliliters (mL) of tetrahydrofuran (THF) and 40 mL of distilled water in a round bottom flask, and the reaction mixture was heated under reflux for about 12 hours. Once the reaction was complete, the resultant was cooled to room temperature, and the THF and distilled water were separated. The separated THF was added dropwise to 100 mL of methanol for crystallization. The obtained solid therefrom was separated by filtering, and was subsequently washed with water and methanol. The resulting solid was dried in a vacuum oven to obtain 11.4 g of Compound 15 (yield: 68%).

MS (m/z, [M+H]⁺): 521.62

Synthesis Example 2: Synthesis of Compound 14

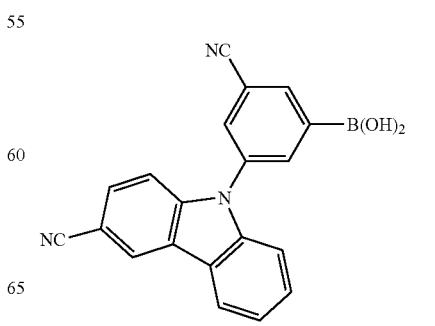

+

-continued

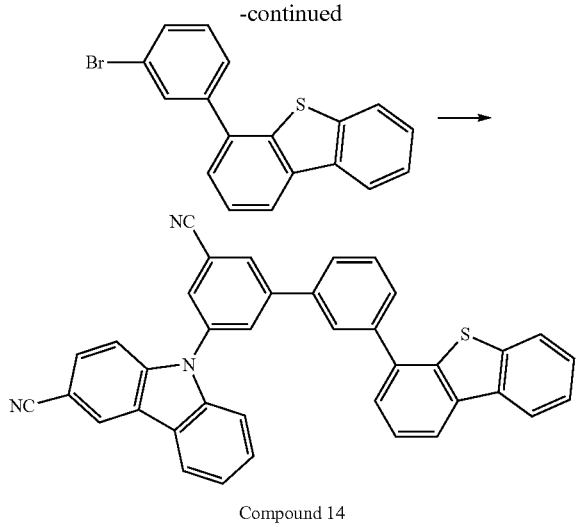

Compound 14

9.838 g (29.18 mmol) of [3-cyano-5-(3-cyano-9H-fluoren-9-yl)phenyl]boronic acid, 8.25 g (24.32 mmol) of 3-bromophenyl-4-dibenzothiophene, 2.810 g (2.43 mmol) of tetrakis(triphenylphosphine)palladium [Pd(PPh$_3$)$_4$], and 6.722 g (48.64 mmol) of potassium carbonate were added to 20 mL of THF and 20 mL of distilled water in a round bottom flask, and the reaction mixture was heated under reflux for about 12 hours. Once the reaction was complete, the resultant was cooled to room temperature, and the THF and distilled water were separated. The separated THF was added dropwise to 60 mL of methanol for crystallization. The obtained solid therefrom was separated by filtering, and was subsequently washed with water and methanol. The resulting solid was dried in a vacuum oven to obtain 8.24 g of Compound 14 (yield: 61%).

MS (m/z, [M+H]$^+$): 551.67

Evaluation Example 1: Evaluation on HOMO, LUMO, T$_1$, and S$_1$ Energy Levels

HOMO, LUMO, T$_1$, and S$_1$ energy levels of Compounds 15 and 14 were evaluated using the method of Table 2. The results thereof are shown in Table 3.

TABLE 3

| Compound No. | HOMO (eV) (found) | LUMO (eV) (found) | T$_1$ (eV) | S$_1$ (eV) |
|---|---|---|---|---|
| 15 | −5.99 | −2.25 | 2.95 | 3.57 |
| 14 | −5.95 | −2.38 | 2.93 | 3.27 |

Referring to Table 3, it was found that Compounds 15 and 14 had electric characteristics that are suitable as a material for forming an organic light-emitting device.

Evaluation Example 2: Thermal Characteristics Evaluation

Thermal analysis (N$_2$ atmosphere, temperature range: from room temperature to 80000 (10° C./min)-TGA, from room temperature to 400° C.-DSC, Pan Type: Pt Pan in disposable Al Pan (TGA) and disposable Al pan (DSC)) was performed on Compounds 15, 14, and A by using thermogravimetric analysis (TGA) and differential scanning calorimetry (DSC). The evaluation results are shown in Table 4. Referring to Table 4, it was found that Compounds 15 and 14 had excellent thermal stability, as compared with Compound A.

TABLE 4

| Compound No. | Tg (° C.) |
|---|---|
| 15 | 124 |
| 14 | 133 |
| Compound A | 72 |

TABLE 2

| | |
|---|---|
| HOMO energy level evaluation method | A potential (Volts, V) versus current (Amperes, A) graph of each compound was obtained by using cyclic voltammetry (CV) (electrolyte: 0.1molar (M) Bu$_4$NClO$_4$/ solvent: CH$_2$Cl$_2$/electrode: 3-electrode system (working electrode: GC, reference electrode: Ag/AgCl, auxiliary electrode: Pt)). Subsequently, from oxidation onset of the graph, a HOMO energy level of the compound was calculated. |
| LUMO energy level evaluation method | Each compound was diluted at a concentration of 1 × 10$^{-5}$ M in CHCl$_3$, and an UV absorption spectrum thereof was measured at room temperature by using a Shimadzu UV-350 spectrometer. A LUMO energy level thereof was calculated by using an optical band gap (Eg) from an edge of the absorption spectrum and a HOMO energy level. |
| T$_1$ energy level evaluation method | A mixture (each compound was dissolved in an amount of 1 milligram (mg) in 3 cubic centimeters (cc) of 2-MeTHF) of 2-MeTHF and each compound was loaded into a quartz cell. Subsequently, the resultant quartz cell was loaded into liquid nitrogen (77 Kelvins (K)), and a photoluminescence spectrum thereof was measured by using a device for measuring photoluminescence. T$_1$ energy level was calculated from the start wavelength of the short-wavelength side of the photoluminescence spectrum. |
| S$_1$ energy level evaluation method | A mixture (each compound was dissolved at a concentration of 10$^{-4}$ [M] in 2-MeTHF) of 2-MeTHF and each compound was loaded into a quartz cell. A fluorescence spectrum was measured at room temperature by using a device for measuring photoluminescence (F7000, available from Hitachi). S$_1$ energy level was calculated from the start wavelength of the short-wavelength side. |

TABLE 4-continued

| Compound No. | Tg (° C.) |
| --- | --- |

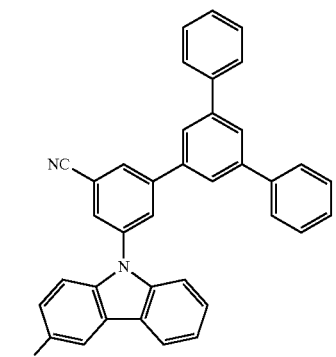

15

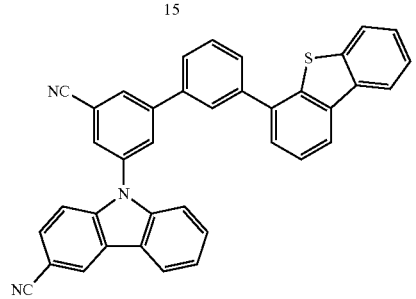

14

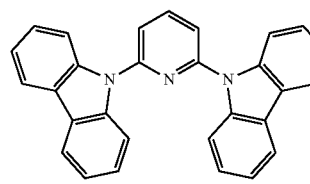

A

Example 1

A glass substrate with an ITO electrode (first electrode, anode) having a thickness of 1,500 Å formed thereon was washed with distilled water in the presence of ultrasound waves. Once the washing with distilled water was complete, ultrasound wave washing was performed on the substrate by using a solvent, such as isopropyl alcohol, acetone, or methanol. Subsequently, the substrate was dried, transferred to a plasma washer, washed for 5 minutes using oxygen plasma, and mounted in a vacuum depositor.

Compound HT3 and Compound HP-1 were co-deposited on the ITO electrode of the glass substrate to form a hole injection layer having a thickness of about 100 Å. Subsequently, Compound HT3 was deposited on the hole injection layer to form a hole transport layer having a thickness of about 1,300 Å. mCP was next deposited on the hole transport layer to form an electron blocking layer having a thickness of about 150 Å, thereby forming a hole transport region.

Subsequently, Compound 15 (host) and FIr6 (dopant, 10 percent by weight (wt %)) were co-deposited on the hole transport region to form an emission layer having a thickness of about 300 Å.

BCP was vacuum deposited on the emission layer to form a hole blocking layer having a thickness of about 100 Å. Compound ET3 and Liq were then co-deposited on the hole blocking layer to form an electron transport layer having a thickness of about 250 Å. Next, Liq was deposited on the electron transport layer to form an electron injection layer having a thickness of about 5 Å, and then, aluminum (Al) second electrode (a cathode) having a thickness of 1,000 Å was formed on the electron injection layer, thereby completing the manufacture of an organic light-emitting device.

Example 2 and Comparative Examples 1 and 2

Organic light-emitting devices were manufactured in the same manner as in Example 1, except that the compounds shown in Table 5 were used instead of Compound 15 as a host in the formation of an emission layer.

Evaluation Example 3: Evaluation of Characteristics of Organic Light-Emitting Device The driving voltage, current density, efficiency, power efficiency, quantum efficiency, and lifespan of the organic light-emitting devices manufactured in Examples 1 and 2 and Comparative Examples 1 and 2 were measured by using a current voltmeter (Keithley 2400) and a luminance meter (Minolta Cs-1000 Å). The evaluation results are shown in Table 5. In Table 5, $T_{95}$ is lifespan data evaluating a period taken for the luminance (at 500 candelas per square meter (cd/m$^2$)) to reach 95% with respect to 100% of the initial luminance.

TABLE 5

| | Host | Driving voltage (V) | Efficiency (cd/A) | Power (lm/W) | Quantum efficiency (%) | $T_{95}$ (hours) |
| --- | --- | --- | --- | --- | --- | --- |
| Example 1 | Compound 15 | 3.49 | 18.56 | 16.73 | 13 | 3.2 |
| Example 2 | Compound 14 | 3.62 | 20.22 | 17.55 | 12 | 4.55 |
| Comparative Example 1 | Compound A | 6.71 | 14.80 | 6.95 | 8.1 | 0.47 |
| Comparative Example 2 | mCP | 5.85 | 19.4 | 13.73 | 16.3 | 0.18 |

TABLE 5-continued

| Host | Driving voltage (V) | Efficiency (cd/A) | Power (lm/W) | Quantum efficiency (%) | T95 (hours) |
|---|---|---|---|---|---|

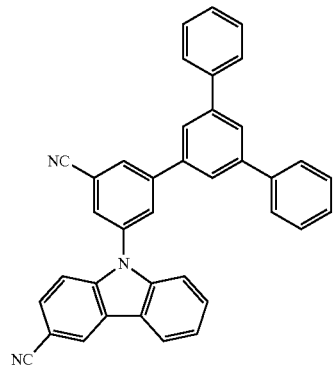

15

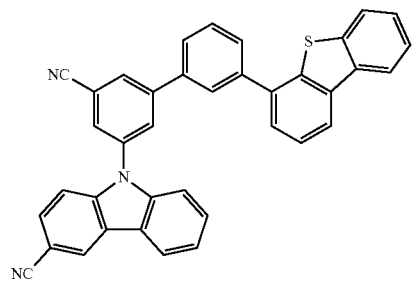

14

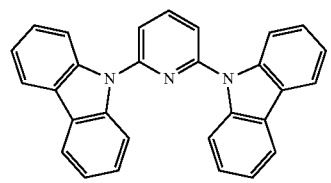

A

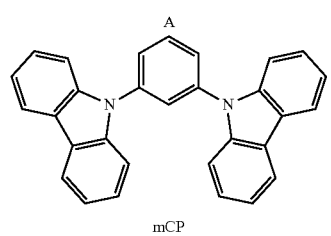

mCP

Referring to Table 5, the organic light-emitting device manufactured in Examples 1 and 2 had a low driving voltage, high efficiency, high power, high quantum emission efficiency, and long lifespan, as compared with the organic light-emitting devices manufactured in Comparative Examples 1 and 2.

As described above, according to the one or more of the above exemplary embodiments, the condensed cyclic compound according has excellent electric characteristics and thermal stability. Accordingly, an organic light-emitting device including the condensed cyclic compound may have a low driving voltage, high efficiency, high power characteristics, high quantum light-emitting efficiency, and a long lifespan.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:
1. A condensed cyclic compound represented by Formula 1:

Formula 1

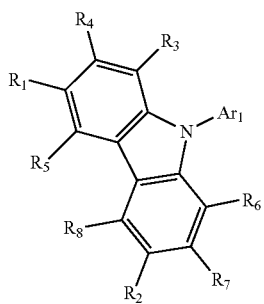

wherein Ar₁ in Formula 1 is selected from groups represented by Formulae 2A-1 to 2A-3

Formula 2A-1

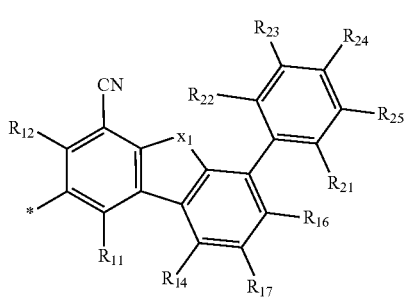

Formula 2A-2

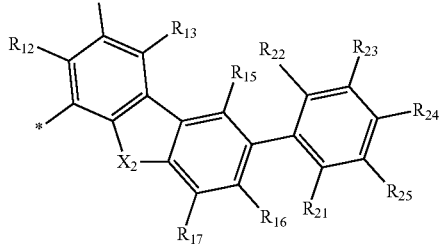

Formula 2A-3

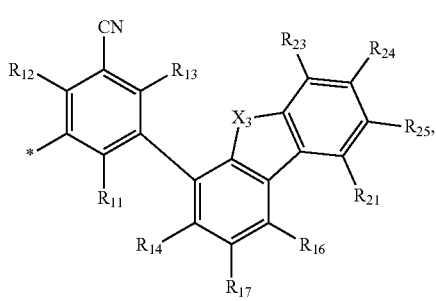

wherein, in Formulae 2A-1 to 2A-3,
X₁ is C(R₃₁)(R₃₂), or Si(R₃₁)(R₃₂),
X₂ is C(R₃₃)(R₃₄), or Si(R₃₃)(R₃₄),
X₃ is C(R₃₅)(R₃₆), or Si(R₃₅)(R₃₆),
wherein
R₁ to R₈, R₁₁ to R₁₇, R₂₁ to R₂₅, and R₃₁ to R₃₆ are each independently selected from hydrogen, deuterium, a cyano group, and groups represented by Formulae 4-1 to 4-29:

Formula 4-1

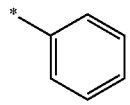

Formula 4-2

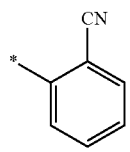

Formula 4-3

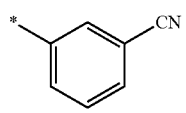

Formula 4-4

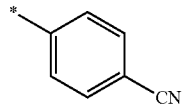

Formula 4-5

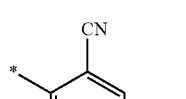

Formula 4-6

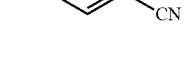

Formula 4-7

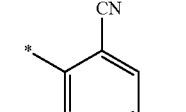

Formula 4-8

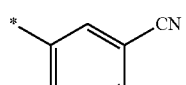

Formula 4-9

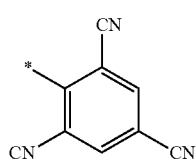

Formula 4-10

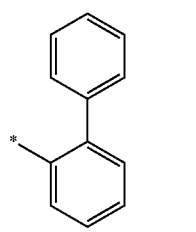

Formula 4-11
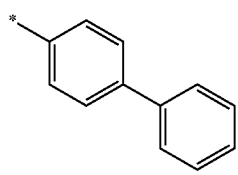
Formula 4-12
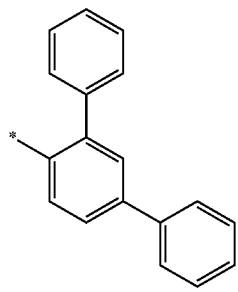
Formula 4-13
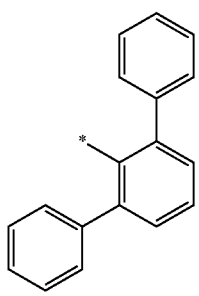
Formula 4-14
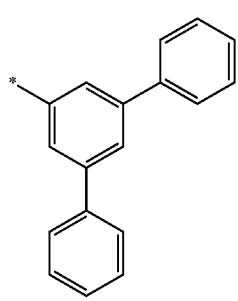
Formula 4-15
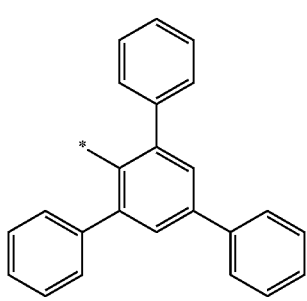
Formula 4-16
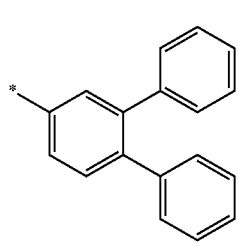
Formula 4-17
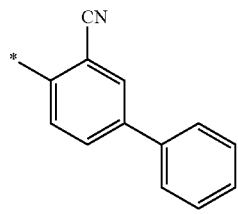
Formula 4-18
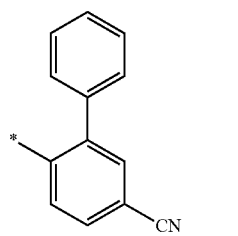
Formula 4-19
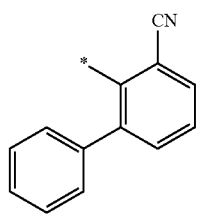
Formula 4-20
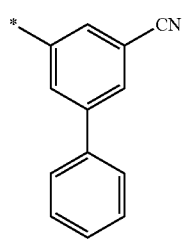
Formula 4-21
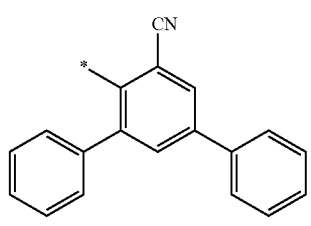
Formula 4-22
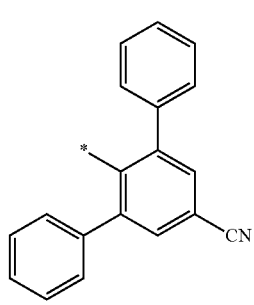
Formula 4-23
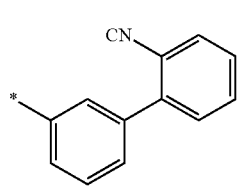

-continued

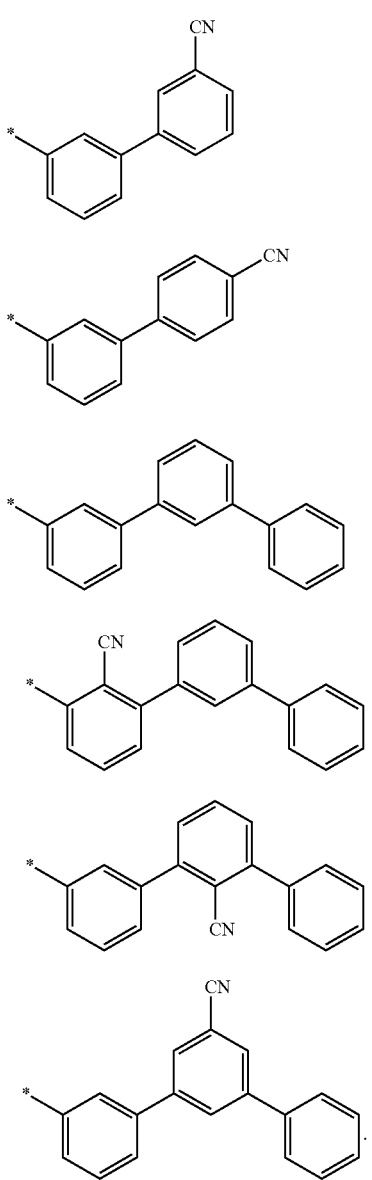

Formula 4-24

Formula 4-25

Formula 4-26

Formula 4-27

Formula 4-28

Formula 4-29 wherein at least one of $R_1$ and $R_2$ in Formula 1 is a cyano group,
wherein the number of cyano groups in each of Formulae 2A-1 to 2A-3 is 2, 3, or 4, and
* indicates a binding site to an adjacent atom.

2. The condensed cyclic compound of claim 1, wherein $R_1$ to $R_8$, $R_{11}$ to $R_{17}$, $R_{21}$ to $R_{25}$, and $R_{31}$ to $R_{36}$ are each independently selected from
hydrogen, deuterium, a cyano group, a $C_1$-$C_{20}$ alkyl group, a phenyl group, a biphenyl group, a terphenyl group, a fluorenyl group, and a dibenzosilolyl group;
a $C_1$-$C_{20}$ alkyl group substituted with at least one of deuterium and a cyano group; and
a phenyl group, a biphenyl group, a terphenyl group, a fluorenyl group, and a dibenzosilolyl group, each substituted with at least one selected from deuterium, a cyano group, a $C_1$-$C_{20}$ alkyl group, a phenyl group, a biphenyl group, a terphenyl group, a fluorenyl group, and a dibenzosilolyl group.

3. The condensed cyclic compound of claim 1, wherein
i) at least one of $R_{17}$ and $R_{25}$ in Formula 2A-1,
ii) at least one of $R_{17}$ and $R_{25}$ in Formula 2A-2, and
iii) $R_{17}$ in Formula 2A-3 are each independently selected from a cyano group and groups represented by Formulae 4-1 to 4-29:

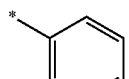

Formula 4-1

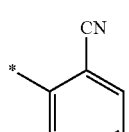

Formula 4-2

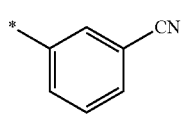

Formula 4-3

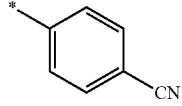

Formula 4-4

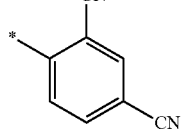

Formula 4-5

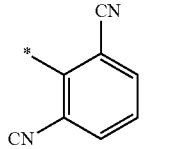

Formula 4-6

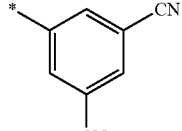

Formula 4-7

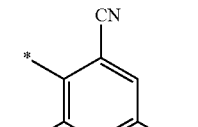

Formula 4-8

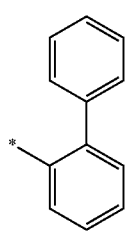

Formula 4-9

-continued
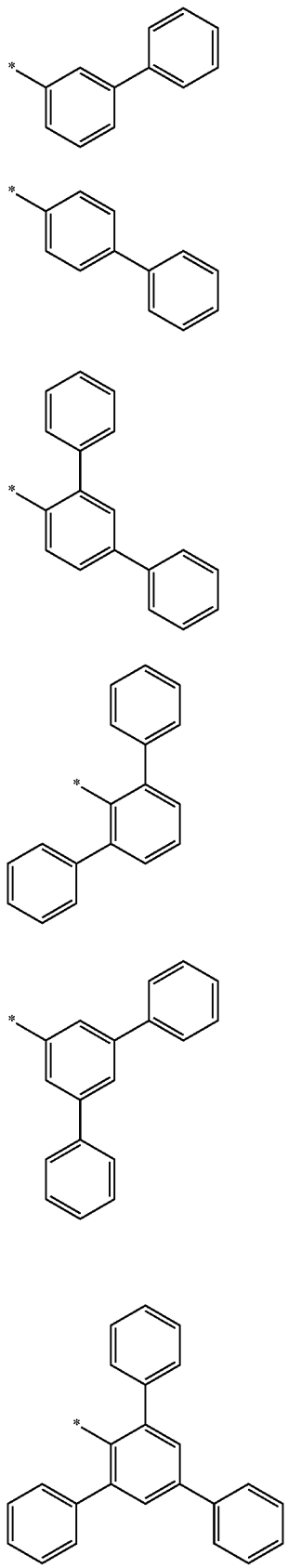
Formula 4-10
Formula 4-11
Formula 4-12
Formula 4-13
Formula 4-14
Formula 4-15
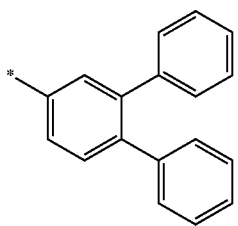
Formula 4-16
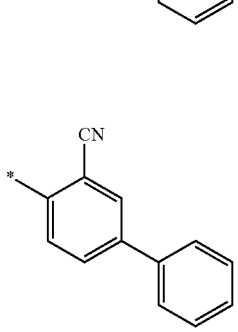
Formula 4-17
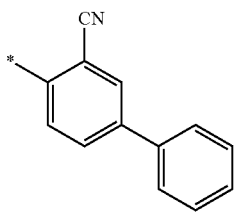
Formula 4-18
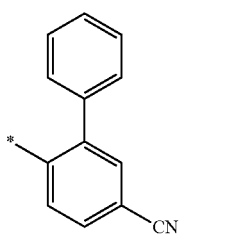
Formula 4-19
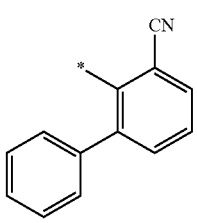
Formula 4-20
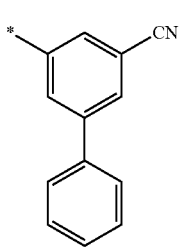
Formula 4-21

-continued

Formula 4-22

Formula 4-23

Formula 4-24

Formula 4-25

Formula 4-26

Formula 4-27

Formula 4-28

Formula 4-29

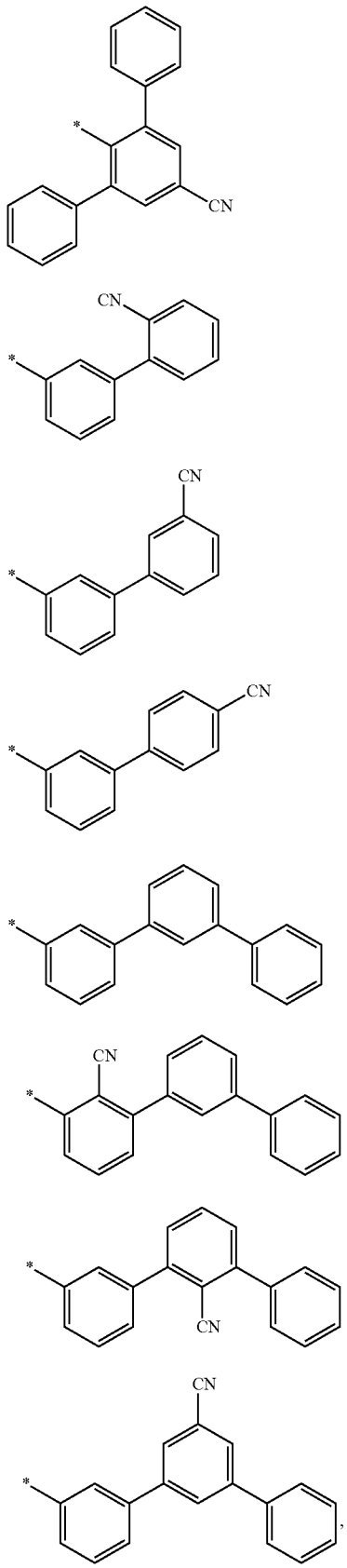

wherein, in Formula 4-1 to 4-29, * indicates a binding site to an adjacent atom.

4. The condensed cyclic compound of claim 1, wherein the number of cyano groups in each of Formulae 2A-1 to 2A-3 is 4.

5. The condensed cyclic compound of claim 1, wherein each of the condensed cyclic compounds has a difference between a triplet ($T_1$) energy level and a singlet ($S_1$) energy level in a range from about 0.1 electron Volts to about 0.6 electron Volts.

6. The condensed cyclic compound of claim 1, wherein each of the condensed cyclic compounds has a triplet ($T_1$) energy level in a range from about 2.9 electron Volts to about 3.1 electron Volts.

7. An organic light-emitting device comprising:
a first electrode;
a second electrode; and
an organic layer disposed between the first electrode and the second electrode, wherein the organic layer comprises an emission layer and at least one condensed cyclic compound represented by Formula 1 of claim 1.

8. The organic light-emitting device of claim 7, wherein
the first electrode is an anode,
the second electrode is a cathode, and
the organic layer comprises
a hole transport region disposed between the first electrode and the emission layer, wherein the hole transport region comprises a hole injection layer, a hole transport layer, an electron blocking layer, or any combination thereof, and
an electron transport region disposed between the emission layer and the second electrode, wherein the electron transport region comprises a hole blocking layer, an electron transport layer, an electron injection layer, or any combination thereof.

9. The organic light-emitting device of claim 7, wherein the emission layer comprises the at least one condensed cyclic compound represented by Formula 1.

10. The organic light-emitting device of claim 9, wherein the emission layer further comprises a phosphorescent dopant comprising an organometallic compound represented by Formula 81:

$$M(L_{81})_{n81}(L_{82})_{n82} \qquad \text{Formula 81}$$

wherein, in Formula 81,
M is selected from Ir, Pt, Os, Ti, Zr, Hf, Eu, Tb, Tm, and Rh,
$L_{81}$ is a ligand represented by Formula 81A,
n81 is an integer selected from 1 to 3, provided that when n81 is 2 or greater, two or more groups $L_{81}$ are identical to or different from each other,
$L_{82}$ is an organic ligand,
n82 is an integer selected from 0 to 4, provided that when n82 is 2 or greater, two or more groups $L_{82}$ are identical to or different from each other,

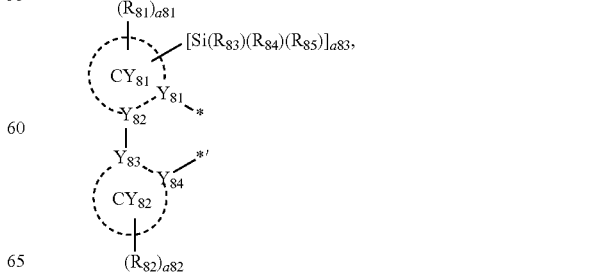

Formula 81A wherein, in Formula 81A, $Y_{81}$ to $Y_{84}$ are each independently C or N, $Y_{81}$ and $Y_{82}$ are linked to each other via a single bond or a double bond, and $Y_{83}$ and $Y_{84}$ are linked to each other via a single bond or a double bond, $CY_{81}$ and $CY_{82}$ are each independently selected from a $C_5$-$C_{30}$ carbocyclic group and a $C_3$-$C_{30}$ hetero carbocyclic group, $CY_{81}$ and $CY_{82}$ are optionally further linked to each other via an organic linking group, $R_{81}$ to $R_{85}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{81}$)($Q_{82}$)($Q_{83}$), —N($Q_{84}$)($Q_{85}$), —B($Q_{86}$)($Q_{87}$), and —P(═O)($Q_{88}$)($Q_{89}$), a81 to a83 are each independently an integer selected from 0 to 5, provided that when a81 is 2 or greater, two or more groups $R_{81}$ are identical to or different from each other, when a82 is 2 or greater, two or more groups $R_{82}$ are identical to or different from each other, when a81 is 2 or greater, adjacent groups $R_{81}$ are optionally linked to each other to form a saturated or unsaturated ring, when a82 is 2 or greater, adjacent groups $R_{82}$ are optionally linked to each other to form a saturated or unsaturated ring, wherein in Formula 81A, * and *' each indicate a binding site to M in Formula 81, wherein at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{91}$)($Q_{92}$)($Q_{93}$), wherein $Q_{81}$ to $Q_{89}$ and $Q_{91}$ to $Q_{93}$ are each independently selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

11. The organic light-emitting device of claim 10, wherein $Y_{81}$ is N, $Y_{82}$ and $Y_{83}$ are each C, and $Y_{84}$ is N or C, wherein $CY_{81}$ and $CY_{82}$ are each independently selected from a cyclopentadiene, a benzene, a heptalene, an indene, a naphthalene, an azulene, an indacene, an acenaphthylene, a fluorene, a spiro-bifluorene, a benzofluorene, a dibenzofluorene, a phenalene, a phenanthrene, an anthracene, a fluoranthene, a triphenylene, a pyrene, a chrysene, a naphthacene, a picene, a perylene, a pentacene, a hexacene, a pentaphene, a rubicene, a coronene, an ovalene, a pyrrole, an isoindole, an indole, an indazole, a pyrazole, an imidazole, a triazole, an oxazole, an isoxazole, an oxadiazole, a thiazole, an isothiazole, a thiadiazole, a purine, a furan, a thiophene, a pyridine, a pyrimidine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzoimidazole, a benzofuran, a benzothiophene, an isobenzothiazole, a benzoxazole, an isobenzoxazole, a benzocarbazole, a dibenzocarbazole, an imidazopyridine, an imidazopyrimidine, a dibenzofuran, a dibenzothiophene, a dibenzothiophene sulfone, a carbazole, a dibenzosilole, and a 2,3-dihydro-1H-imidazole.

12. The organic light-emitting device of claim 10, wherein in Formula 81A, at least one selected from a81 number of groups $R_{81}$ and a82 number of groups $R_{82}$ is a cyano group or deuterium.

13. The organic light-emitting device of claim 9, wherein the emission layer emits blue light.

* * * * *